United States Patent [19]

Nishi et al.

[11] 4,435,404
[45] Mar. 6, 1984

[54] CARBOSTYRIL DERIVATIVES

[75] Inventors: Takao Nishi; Tatsuyoshi Tanaka; Kazuyuki Nakagawa, all of Tokushima, Japan

[73] Assignee: Otsuka Pharmaceutical Co., Ltd., Tokyo, Japan

[21] Appl. No.: 261,177

[22] PCT Filed: Jun. 4, 1980

[86] PCT No.: PCT/JP80/00122
§ 371 Date: Apr. 30, 1981
§ 102(e) Date: Apr. 30, 1981

[87] PCT Pub. No.: WO81/02421
PCT Pub. Date: Sep. 3, 1981

[30] Foreign Application Priority Data

Feb. 29, 1980 [JP] Japan ................................. 55-25658

[51] Int. Cl.³ .................... A61K 31/47; C07D 215/22
[52] U.S. Cl. ..................................... 424/258; 546/157; 546/158; 546/155
[58] Field of Search ................ 424/258, 250; 546/155, 546/157, 158; 544/363

[56] References Cited

U.S. PATENT DOCUMENTS

| | | | |
|---|---|---|---|
| 4,070,470 | 1/1978 | Makagawa et al. | 424/258 |
| 4,216,220 | 8/1980 | Nakagawa et al. | 424/274 |
| 4,298,739 | 11/1981 | Nishi et al. | 546/158 |
| 4,313,947 | 2/1982 | Nakagawa et al. | 424/248.54 |

FOREIGN PATENT DOCUMENTS

| | | |
|---|---|---|
| 54-163825 | 12/1979 | Japan . |
| 55-76864 | 6/1980 | Japan ................................. 424/258 |
| 55-79370 | 6/1980 | Japan ................................. 424/258 |
| 55-79371 | 6/1980 | Japan ................................. 424/258 |
| 55-79372 | 6/1980 | Japan ................................. 424/258 |

OTHER PUBLICATIONS

Nishi et al., Chemical Abstracts, vol. 90, 203,891x, (1979).
Nishi et al., Chemical Abstracts, vol. 93, 26,291r, (1980).
Nishi et al., Chemical Abstracts, vol. 93, 46,4397y, (1980).
Otsuka Pharm. Co., Ltd., Chemical Abstracts, vol. 95, 97,609c, (1981).
Otsuka Pharm. Co., Ltd., Chemical Abstracts, vol. 96, 181,163f, (1982).
Balazs, Proc. Europ. Soc. Study Drug Tox., vol. 15, pp. 71-79, (1974).

Primary Examiner—Diana G. Rivers
Attorney, Agent, or Firm—Finnegan, Henderson, Farabow, Garrett & Dunner

[57] ABSTRACT

Novel carbostyril derivative and its salt represented by the general formula (1),

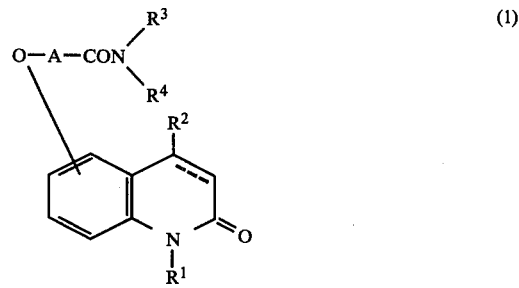

wherein $R^1$ is a hydrogen atom, a lower alkyl group, a lower alkenyl group or a phenyl-lower alkyl group; $R^2$ is a hydrogen atom, a lower alkyl group or a group of the formula

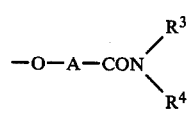

wherein A is a lower alkylene group; $R^3$ is a lower alkyl group, a hydroxy lower alkyl group, a lower alkoxy-lower alkyl group, a lower alkanoyloxy-lower alkyl group or a benzoyloxy-lower alkyl group; and $R^4$ is a $C_{3-10}$-cycloalkyl group which may have at least one hydroxyl group as the substituent(s) in the cycloalkyl ring, a $C_{3-10}$-cycloalkyl-lower alkyl group, a phenyl group, a phenyl-lower alkyl group which may have at least one lower alkoxy group as the substituent(s) in the phenyl ring, a lower alkyl group which may have at least one hydroxyl group as the substituent(s), a heterocyclic ring residue or a lower alkyl group having one heterocyclic ring residue as the substituent; further, $R^3$, $R^4$ and the adjacent nitrogen atom, as well as with or without another nitrogen atom, may form a group of the formula

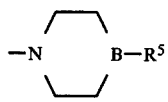

(wherein $R^5$ is a phenyl group, a $C_{3-10}$-cycloalkyl group or a phenyl-lower alkyl group; and B is a methine group or a nitrogen atom); the carbon-carbon bond between the 3- and 4-positions in the carbostyril skeleton is a single or double bond; the substituted position of the group of the formula

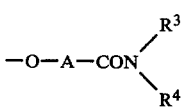

is any one of 5-, 6-, 7- or 8-position in the carbostyril skeleton; when the group of the formula

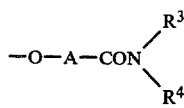

is substituted at 5-, 6-, 7- or 8-position in the carbostyril skeleton, then $R^2$ is a hydrogen atom or a lower alkyl group; alternatively, when $R^2$ is a group of the formula

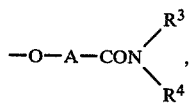

then 5-, 6-, 7- and 8-positions in the carbostyril skeleton are hydrogen atoms and are not substituted with groups of the formula

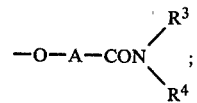

and when $R^3$ is a lower alkyl group, then $R^4$ should be neither of a $C_{3-10}$-cycloalkyl group, a $C_{3-10}$-cycloalkyl-lower alkyl group nor a lower alkyl group, having effects for preventing and treating thrombosis and embolism.

27 Claims, No Drawings

CARBOSTYRIL DERIVATIVES

THECHNICAL FIELD

The present invention relates to novel carbostyril derivatives and process for producing the same and to a treating agent for preventing thrombosis and embolism containing said carbostyril derivative as the active ingredient.

BACKGROUND ART

There have been known certain numbers of carbostyril derivatives which exhibit useful pharmacological activities. For example, U.S. Pat. No. 4,070,470 and German Pat. (Laid-open) No. 2,527,937 teach carboxyalkoxy substituted carbostyril derivatives having blood platelet aggregation inhibitory effect; German Pat. (Laid-open) No. 2,825,048 teaches aminocarbonylalkoxycarbostyril derivatives having platelet aggregation inhibitory effect, phosphodiesterase inhibitory, effect, antiinflammatory effect, antiulcer effect and vasodilation effect. Further, U.S. Pat. No. 3,682,920 teaches 1-substituted derivatives of 3,4-dihydrocarbostyril which are useful as analgesic agents.

However, these carbostyril derivatives known in the prior art have some side effects, and which will cause some troubles in medical use.

DISCLOSURE OF INVENTION

In consideration of these facts, the present inventors have made extensive studies on carbostyril derivatives for the purpose of to obtain novel carbostyril derivatives having less side effects, particularly less side effects to heart and succeeded the present invention.

Thus the novel carbostyril derivative of the present invention has excellent blood platelet aggregation inhibitory effect, phosphodiesterase inhibitory effect, myocardium contraction increasing effect (positive inotropic effect), anti-ulcer effect, anti-inflammatory effect, hypotensive effect, cerebral blood flow increasing effect, blood platelet clot dissociation effect and thromboxan $A_2$ antagonism, and therefore it is useful as prophylaxis and treating agent for thrombosis and embolism, such as cerebral apoplexy, cerebral infarction, myocardinal infarction; cerebral blood flow improver, anti-inflammatory agent, anti-asthmatic agent, cardiac stimulant, hypotensive agent and phosphodiesterase inhibitor. Further, the carbostyril derivative represented by the general formula (1) of the present invention has low toxicity and particularly side effects to heart such as increasing of heart rate, cardiovascular hypertrophy, myocardium disorder or the like are very weak, while it can be absorbed into blood well and quickly and can be kept relatively higher concentration in blood and the useful pharmacological effect as mentioned above can be retained for relatively longer period of time.

According to the present invention, there is provided novel carbostyril derivative and its salt represented by the general formula (1),

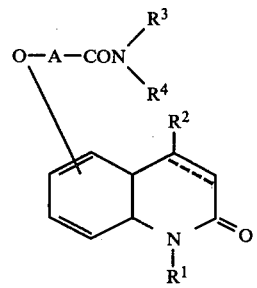

wherein $R^1$ is a hydrogen atom, a lower alkyl group, a lower alkenyl group or a phenyl-lower alkyl group; $R^2$ is a hydrogen atom, a lower alkyl group or a group of the formula

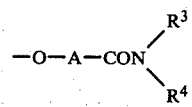

[wherein A is a lower alkylene group; $R^3$ is a lower alkyl group, a hydroxy-lower alkyl group, a lower alkoxy-lower alkyl group, a lower alkanoyloxy-lower alkyl group or a benzoyloxy-lower alkyl group; and $R^4$ is a $C_{3\text{-}10}$-cycloalkyl group which may have at least one hydroxyl group as the substituent(s) in the cycloalkyl ring, a $C_{3\text{-}10}$-cycloalkyl-lower alkyl group, a phenyl group, a phenyl-lower alkyl group which may have at least one lower alkoxy group as the substituent(s) in the phenyl ring, a lower alkyl group which may have at least one hydroxyl group as the substituent(s), a heterocyclic ring residue or a lower alkyl group having one heterocyclic ring residue as the substituent; further, $R^3$, $R^4$ and the adjacent nitrogen atom, as well as with or without another nitrogen atom, may form a group of the formula

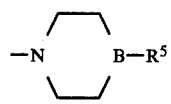

(wherein $R^5$ is a phenyl group, a $C_{3\text{-}10}$-cycloalkyl group or a phenyl-lower alkyl group; and B is a methyne group or a nitrogen atom)]; the carbon-carbon bond between the 3- and 4-positions in the carbostyril skeleton is a single or double bond; the substituted position of the group of the formula

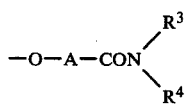

is any one of 5-, 6-, 7- or 8-position in the carbostyril skeleton; when the group of the formula

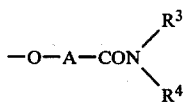

is substituted at 5-, 6-, 7- or 8-position in the carbostyril skeleton, then $R^2$ is a hydrogen atom or a lower alkyl group; alternatively, when $R^2$ is a group of the formula

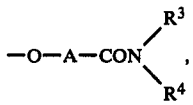

then 5-, 6-, 7- and 8-positions in the carbostyril skeleton are hydrogen atoms and are not substituted with groups of the formula

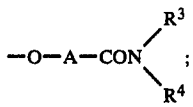

and when $R^3$ is a lower alkyl group, then $R^4$ should be neither of a $C_{3-10}$-cycloalkyl group, a $C_{3-10}$-cycloalkyl-lower alkyl group nor a lower alkyl group; and a treating agent for preventing thrombosis and embolism containing said carbostyril derivative as the active ingredient.

BEST MODE FOR CARRYING OUT THE INVENTION

In the present specification, the term "a lower alkylene group" means an alkylene group having straight or branched form having 1 to 6 carbon atoms and the examples including methylene group, ethylene group, methylmethylene group, trimethylene group, 2-methyltrimethylene group, 2,2-dimethyltrimethylene group, tetramethylene group, pentamethylene group, hexamethylene group, 2-ethyltrimethylene group, 1-methyltrimethylene group and the like. The term "a lower alkyl group" means an alkyl group having straight or branched form having 1 to 6 carbon atoms, and the examples including methyl group, ethyl group, propyl group, isopropyl group, butyl group, tert-butyl group, pentyl group, hexyl group and the like. The term "a hydroxy-lower alkyl group" means a hydroxyalkyl group having a straight or branched form of alkyl group having 1 to 6 carbon atoms in which 1, 2 or 3 hydroxyl groups are substituted as the substituents and the examples including hydroxymethyl group, 2-hydroxyethyl group, 3-hydroxypropyl group, 4-hydroxybutyl group, 2-hydroxybutyl group, 3-hydroxybutyl group, 5-hydroxypentyl group, 2-hydroxypentyl group, 3-hydroxypentyl group, 4-hydroxypentyl group, 6-hydroxyhexyl group, 2-hydroxyhexyl group, 3-hydroxyhexyl group, 4-hydroxyhexyl group, 1-methyl-2-hydroxyethyl group, 2-hydroxypropyl group, 1,1-dimethyl-2-hydroxyethyl group, 1,2-dihydroxyethyl group, 2,2-dihydroxyethyl group, 1,3-dihydroxypropyl group, 2,3-dihydroxypropyl group, 1,2,3-trihydroxypropyl group, 1,4-dihydroxybutyl group, 2,4-dihydroxybutyl group, 3,4-dihydroxybutyl group, 1,2-dihydroxybutyl group, 2,3-dihydroxybutyl group, 1,3-dihydroxybutyl group, 2,2-dihydroxybutyl group, 1,2,3-trihydroxybutyl group, 2,3,4-trihydroxybutyl group, 2,3-dihydroxypentyl group, 3,4-dihydroxypentyl group, 3,5-dihydroxypentyl group, 2,3,4-trihydroxypentyl group, 3,4,5-trihydroxypentyl group, 2,4,5-trihydroxypentyl group, 2,3-dihydroxyhexyl group, 2,5-dihydroxyhexyl group, 2,6-dihydroxyhexyl group, 3,4-dihydroxyhexyl group, 4,5-dihydroxhexl group, 4,6-dihydroxyhexyl group, 5,6-dihydroxyhexyl group, 2,3,4-trihydroxyhexyl group, 3,4,5-trihydroxyhexyl group, 4,5,6-trihydroxyhexyl group. The term "a heterocyclic residual group" means a 5- or 6-membered heterocyclic group having a nitrogen atom, oxygen atoms or sulfur atoms as the hetero atoms and the examples including pyridyl, furyl, tetrahydrofuryl, 2H-pyranyl, 4H-pyranyl, 3,4-dihydro-2H-pyranyl, tetrahydropyranyl, thienyl, tetrahydrothienyl, tetrahydrothiopyranyl, pyrroyl, pyrrolidinyl, piperidinyl or the like. The term "a lower alkyl group having one heterocyclic ring residue as the substituent" means an alkyl group having a straight or branched form having 1 to 6 carbon atoms in which the above-mentioned heterocyclic residual group(s) are substituted as the substituent(s), and the examples including 3-pyridylmethyl, 2-pyridylmethyl, 4-pyridylmethyl, 2-(3-pyridyl)ethyl, 3-(3-pyridyl)propyl, 4-(3-pyridyl)butyl, 2,2-dimethyl-2-(2-pyridyl)ethyl, 5-(4-pyridyl)pentyl, 6-(4-pyridyl)hexyl, 1,1-dimethyl-2-(3-pyridyl)ethyl, 2-furylmethyl, 3-furylmethyl, 2-(3-furyl)ethyl, 4-(2-furyl)butyl, 2-tetrahydrofurylmethyl, 3-tetrahydrofurylmethyl, 2-(3-tetrahydrofuryl)ethyl, 5-(2-tetrahydrofuryl)pentyl, 2-2H-pyranylmethyl, 3-2H-pyranylmethyl, 2-(3-2H-pyranyl)ethyl, 6-(2-2H-pyranyl)hexyl, 2-4H-pyranylmethyl, 2-(4H-pyranyl)ethyl, 2-3,4-dihydro-2H-pyranylmethyl, 4-3,4-dihydro-2H-pyranylmethyl, 2-(3-3,4-dihydro-2H-pyranyl)ethyl, 4-(4-3,4-dihydro-2H-pyranyl)butyl, 2-tetrahydropyranylmethyl, 2-(2-tetrahydropyranyl)ethyl, 3-(4-tetrahydropyranyl)propyl, 5-(3-tetrahydropyranyl)pentyl, 2-thienylmethyl, 2-(2-thienyl)ethyl, 3-thienylmethyl, 4-(3-thienyl)butyl, 2-tetrahydrothienylmethyl, 3-tetrahydrothioenylmethyl, 2-(2-tetrahydrothienyl)ethyl, 5-(3-tetrahydrothienyl)pentyl, 2-tetrahydrothiopyranylmethyl, 3-tetrahydrothiopyranylmethyl, 4-tetrahydrothiopyranylmethyl, 2-(2-tetrahydrothiopyranyl)ethyl, 4-(3-tetrahydrothiopyranyl)butyl, 2-pyrroylmethyl, 3-pyrroylmethyl, 2-(2-pyrroyl)ethyl, 5-(2-pyrroyl)pentyl, 2-pyrrolidinylmethyl, 3-pyrrolidinylmethyl, 2-(2-pyrrolidinyl)ethyl, 6-(3-pyrrolidinyl)hexyl, 2-piperidinylmethyl, 3-piperidinylmethyl, 4-piperidinylmethyl, 2-(2-piperidinyl)ethyl, 4-(4-piperidinyl)butyl or the like. The term "a lower alkenyl group" means a straight or branched form alkenyl group havin 2 to 6 carbon atoms, and the examples including vinyl, allyl, 2-butenyl, 3-butenyl, 1-methylallyl, 2-pentenyl, 2-hexenyl or the like. The term "a phenyl-lower alkyl group" means a phenyl-alkyl group in which a straight or branched form alkyl group having 1 to 6 carbon atoms having a phenyl groups as the substituent and the examples including benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, or the like. The term "a lower alkoxy-lower alkyl group" means a alkoxyalkyl group in which a straight or branched form alkyl group having 1 to 6 carbon atoms having a straight or branched form alkoxy group having 1 to 6 carbon atoms as the substituent and the examples including methoxymethyl, 2-methoxyethyl, 3-methoxypropyl, 4-methoxybutyl, 5-methoxypentyl, 6-methoxyhexyl, 1-methyl-2-methoxyethyl, 2-methoxypropyl, 1,1-dimethyl-2-methoxyethyl, ethoxymethyl, 2-ethoxyethyl, 3-ethoxypropyl, 4-ethoxybutyl, 5-ethoxypentyl, 6-ethoxyhexyl, 1-methyl-2-ethoxyethyl, 2-ethoxypropyl, 1,1-dimethyl-2-ethoxyethyl, propoxymethyl, 2-propoxyethyl, 3-propoxypropyl, 4-propoxybutyl, 6-propoxyhexyl, 2- propoxypropyl, 2-isopropoxyethyl, 2-butoxyethyl, 3-butoxypropyl, 4-butoxybutyl, 6-butoxyhexyl, 2-tert-butoxyethyl, 2-pentyloxyethyl, 5-pentyloxypentyl, 2-hexyloxyethyl, 6-hexyloxyhexyl or the like. The term "a lower alkanoyloxy-lower alkyl group" means an alkanoyloxy-alkyl group in which a straight or branched form alkyl group having 1 to 6 carbon atoms having a straight or branched form alkanoyloxy group having 1 to 6 carbon atoms as the substituent and the examples including 2-formyloxyethyl, 3-formyloxypropyl, 4-formyloxybutyl, 2-formyloxypropyl, acetyloxymethyl, 2-acetyloxyethyl, 3-acetyloxypropyl, 4-acetyloxybutyl, 5-acetyloxypentyl, 6-acetyloxyhexyl, 1-methyl-2-acetyloxyethyl, 2-acetyloxypropyl, 1,1-dimethyl-2-acetyloxyethyl, 2-propionyloxyethyl, 3-propionyloxypropyl, 4-propionyloxybutyl, 5-propionyloxypentyl, 6-propionyloxyhexyl, 2-propionyloxypropyl, 2-butyryloxyethyl, 3-butyryloxypropyl, 4-butyryloxybutyl, 2-butyryloxypropyl, 2-isobutyryloxyethyl, 4-isobutyryloxybutyl, 2-pentanoyloxyethyl, 5-pentanoyloxypentyl, 2-tert-butylcarbonyloxyethyl, 2-hexanoyloxyethyl, 6-hexanoyloxyhexyl or the like. The term "a benzoyloxy-lower alkyl group" means a benzoyloxyalkyl group in which a straight or branched form alkyl group having 1 to 6 carbon atoms having a benzoyloxy group as the substituent, and the examples including benzoyloxymethyl, 2-benzoyloxyethyl, 3-benzoyloxypropyl, 4-benzoyloxybutyl, 5-benzoyloxypentyl, 6-benzoyloxyhexy, 1-methyl-2-benzoyloxyethyl, 2-benzoyloxypropyl, 1,1-dimethyl-2-benzoyloxyethyl or the like. The term "a C$_{3-10}$-cycloalkyl group which may have at least one hydroxy group as the substituent(s)" means a cycloalkyl group having 3 to 10 carbon atoms having one, two or three hydroxyl groups as the substituents in the cycloalkyl ring, and the examples including cyclopropyl, cyclobutyl, 2-hydroxycyclobutyl, 3-hydroxycyclobutyl, cyclopentyl, 2-hydroxycyclopentyl, 3-hydroxycyclopentyl, cyclohexyl, 2-hydroxycyclohexyl, 3-hydroxycyclohexyl, 4-hydroxycyclohexyl, 3,4-dihydroxycyclohexyl, 3,4,5-trihydroxycyclohexyl, cycloheptyl, 2-hydroxycycloheptyl, 3-hydroxycycloheptyl, 4-hydroxycycloheptyl, cyclooctyl, 2-hydroxycyclooctyl, 3-hydroxycyclooctyl, 4-hydroxycyclooctyl, 5-hydroxycyclooctyl, cyclononanyl, 2-hydroxycyclononanyl, 3-hydroxycyclononanyl, 4-hydroxycyclononanyl, cyclodecanyl, 2-hydroxycyclodecanyl, 4-hydroxycyclodecanyl or the like. The term "a C$_{3-10}$-cycloalkyl-lower alkyl group" means a cycloalkylalkyl group in which a straight or branched alkyl group having 1 to 6 carbon atoms having a cycloalkyl group having 3 to 10 carbon atoms as the substituent and the examples including cyclopropylmethyl, 4-cyclohexylbutyl, 2-cyclopentylethyl, cyclohexylmethyl, 2-cyclopentylpropyl, 3-cyclohexylpropyl, cyclopentylmethyl, 2-cyclohexylethyl, 2-cyclohexylpropyl, 2-cycloheptylethyl, 3-cyclobutylpropyl, 1,1-dimethyl-2-cyclohexylethyl, 1-methyl-2-cyclopentylethyl, 2-cyclooctylethyl, cyclononanylmethyl, 2-cyclodecanylethyl, 5-cyclohexyl, 6-cyclohexylhexyl or the like. The term "a phenyl-lower alkyl group which may have at least one lower alkoxy group as the substituents on the phenyl ring" means an alkyl group having 1 to 6 carbon atoms having a phenyl group as the substituent thereof and further said phenyl group may have one, two or three alkoxy groups having 1 to 6 carbon atoms as the substituents thereto, the examples of said alkoxy groups are methoxy, ethoxy, propoxy, isopropoxy, butoxy, tertbutoxy, pentyloxy, hexyloxy or the like. The examples of said phenyl-lower alkyl groups including benzyl, 2-phenylethyl, 1-phenyethyl, 3-phenylpropyl, 4-phenylbutyl, 1,1-dimethyl-2-phenylethyl, 2-methyl-3-phenylpropyl, 5-phenylpentyl, 6-phenylhexyl, 2-methoxybenzyl, 3-methoxybenzyl, 4-methoxybenzyl, 3,4-dimethoxybenzyl, 3,4,5-trimethoxybenzyl, 2-(2-methoxyphenyl)ethyl, 2-(3-methoxyphenyl)ethyl, 2-(4-methoxyphenyl)ethyl, 2-(3,4-dimethoxyphenyl)ethyl, 2-(3,4-diethoxyphenyl)ethyl, 2-(3,4-diisopropoxyphenyl)ethyl, 2-(3,4-dibutoxyphenyl)ethyl, 1-(3,4-dimethoxyphenyl)ethyl, 2-(3,4,5-trimethoxyphenyl)ethyl, 3-(3,4-dimethoxyphenyl)propyl, 4-(3,4-dimethoxyphenyl)butyl, 6-(3,4-dimethoxyphenyl)hexyl, 1,1-dimethyl-2-(3,4-dimethoxyphenyl)ethyl, 2-(2,5-dimethoxyphenyl)ethyl or the like.

Among the compound provided according to the present invention, the specific examples of the compounds are listed below.

6-{3-[N-(2-Hydroxyethyl)-N-cyclohexylaminocarbonyl]propoxy}-3,4-dihydrocarbostyril and 6-{3-[N-(2-hydroxyethyl)-N-cyclohexylaminocarbonyl]propoxy}-carbostyril (hereinafter such compounds will be referred to as "6-{3-[N-(2-hydroxyethyl)-N-cyclohexylaminocarbonyl]propoxy}-3,4-dihydrocarbostyril and its 3,4-dehydro compound".)

6-{3-[N-(4-Hydroxybutyl)-N-cyclohexylaminocarbonyl]propoxy}-3,4-dihydrocarbostyril and its 3,4-dehydro compound 6-{3-[N-(6-Hydroxyhexyl)-N-cyclohexylaminocarbonyl]propoxy}-3,4-dihydrocarbostyril and its 3,4-dehydro compound 6-{3-[N-(2-Hydroxyethyl)-N-cyclooctylaminocarbonyl]propoxy}-3,4-dihydrocarbostyril and its 3,4-dehydro compound 5-{3-[N-(2-Hydroxyethyl)-N-cyclopropylaminocarbonyl]propoxy}-3,4-dihydrocarbostyril and its 3,4-dehydro compound 6-{3-[N-(2-Hydroxypropyl)-N-cyclohexylaminocarbonyl]propoxy}-3,4-dihydrocarbostyril and its 3,4-dehydro compound 5-{3-[N-(2-Hydroxyethyl)-N-cyclohexylaminocarbonyl]propoxy}-3,4-dihyrocarbostyril and its 3,4-dehydro compound 7-{3-[N-(2-Hydroxyethyl)-N-cyclohexylaminocarbonyl]propoxy}-3,4-dihydrocarbostyril and its 3,4-dehydro compound 8-{3-[N-(2-Hydroxyethyl)-N-cyclohexylaminocarbonyl]propoxy}-3,4-dihydrocarbostyril and its 3,4-dehydro compound 5-{3-[N-(4-Hydroxybutyl)-N-cyclooctylaminocarbonyl]propoxy}-3,4-dihydrocarbostyril and its 3,4-dehydro compound 6-{3-[N-(4-Hydroxybutyl)-N-cyclooctylaminocarbonyl]propoxy}-3,4-dihydrocarbostyril and its 3,4-dehydro compound 6-{2-N-[2-Hydroxyethyl)-N-cyclohexymainocarbonyl]ethoxy}-3,4-dihydrocarbostyril and its 3,4-dehydro compound 6-{3-[N-(2-Hydroxyethyl)-N-cyclodecanylaminocarbonyl]propoxy}-3,4-dihydrocarbostyril and its 3,4-dehydro compound 5-{3-[N-(2-Hydroxyethyl)-N-cyclodecanylaminocarbonyl]propoxy}-3,4-dihydrocarbostyril and its 3,4-dehydro compound 6-{4-[N-(2-Hydroxyethyl)-N-cyclohexylaminocarbonyl]butoxy}-3,4-dihydrocarbostyril and its 3,4-dehydro compound 6-{6-[N-(2-Hydroxyethyl)-N-cyclohexylaminocarbonyl]hexyloxy}-3,4-dihydrocarbostyril and its 3,4-dehydro compound 6-{2-Methyl-3-[N-(2-hydroxyethyl)-N-cyclohexylaminocarbonyl]propoxy}-3,4-dihydrocarbostyril and its 3,4-dehydro compound 6-{2,2-Dimethyl-3-[N-(2-hydroxyethyl)-N-cyclohexylaminocarbonyl]propoxy}-3,4-dihydrocarbostyril and its 3,4-dehydro compound 5-[N-(2-Hydroxyethyl)-N-cyclohexylaminocarbonylmethoxy]-3,4-dihydrocarbostyril and its 3,4-dehydro compound 6-{3-[N-(2-Hydroxyethyl)-N-(3-pyridyl)aminocarbonyl]propoxy}-3,4-dihydrocarbostyril and its 3,4-dehydro compound 6-{3-[N-Ethyl-N-(3-pyridyl)aminocarbonyl]propoxy}-3,4-dihydrocarbostyril and its 3,4-dehydro compound 5-{3-[N-Methyl-N-(2-pyridyl)aminocarbonyl]propoxy}-3,4-dihydrocarbostyril and its 3,4-dehydro compound 7-{3-[N-Methyl-N-(4-pyridyl)aminocarbonyl]propoxy}-3,4-dihydrocarbostyril and its 3,4-dehydro compound 6-{3-[N-Butyl-N-(3-pyridyl)aminocarbonyl]propoxy}-3,4-dihydrocarbostyril and its 3,4-dehydro compound 6-{3-[N-Methyl-N-(2-furyl)aminocarbonyl]propoxy}-3,4-dihydrocarbostyril and its 3,4-dehydro compound 5-{3-[N-Ethyl-N-(3-furyl)aminocarbonyl]propoxy}-3,4-dihydrocarbostyril and its 3,4-dehydro compound 8-{2-Methyl-[N-hexyl-N-(2-furyl)aminocarbonyl]propoxy}-3,4-dihydrocarbostyril and its 3,4-dehydro compound 6-{3-[N-Methyyl-N-(2-tetrahydrofuryl)aminocarbonyl]propoxy}-3,4-dihydrocarbostyril and its 3,4-dehydro compound 6-{3-[N-(2-Hydroxyethyl)-N-(2-furyl)aminocarbonyl]propoxy}-3,4-dihydrocarbostyril and its 3,4-dehydro compound 6-{3-[N-(2-Hydroxyethyl)-N-(2-tetrahydrofuryl)aminocarbonyl]propoxy}-3,4-dihydrocarbostyril and its 3,4-dehydro compound 5-{2-Methyl-3-[N-ethyl-N-(3-tetrahydrofuryl)aminocarbonyl]propoxy}-3,4-dihydrocarbostyril and its 3,4-dehydro compound 7-{3-[N-Methyl-N-(2-tetrahydrofuryl)aminocarbonyl]propoxy}-3,4-dihydrocarbostyril and its 3,4-dehydro compound 6-{3-[N-Ethyl-N-(2-2H-pyranyl)aminocarbonyl]propoxy}-3,4-dihydrocarbostyril and its 3,4-dehydro compound 5-{3-[N-Butyl-N-(4-2H-pyranyl)aminocarbonyl]propoxy}-3,4-dihydrocarbostyril and its 3,4-dehydro compound 8-{4-[N-Methyl-N-(3-2H-pyranyl)aminocarbonyl]butoxy}-3,4-dihydrocarbostyril and its 3,4-dehydro compound 6-{3-[N-Methyl-N-(2-4H-pyranyl)aminocarbonyl]propoxy}-3,4-dihydrocarbostyril and its 3,4-dehydro compound 5-{4-[N-Ethyl-N-(4-4H-pyranyl)aminocarbonyl]butoxy}-3,4-dihydrocarbostyril and its 3,4-dehydro compound 6-{3-[N-Methyl-(2-3,4-dihydro-2H-pyranyl)aminocarbonyl]butoxy}-3,4-dihydrocarbostyril and its 3,4-dehydro compound 6-{3-[N-(2-Hydroxyethyl)-N-(2-tetrahydrofuryl)aminocarbonyl]propoxy}-3,4-dihydrocarbostyril and its 3,4-dehydro compound 5-{3-[N-Ethyl-(3-3,4-dihydro-2H-pyranyl)aminocarbonyl]propoxy}-3,4-dihydrocarbostyril and its 3,4-dehydro compound 7-{2-[N-Methyl-(4-3,4-dihydro-2H-pyranyl)aminocarbonyl]ethoxy}-3,4-dihydrocarbostyril and its 3,4-dehydro compound 6-{3-[N-Methyl-N-(2-tetrahydropyranyl)aminocarbonyl]propoxy}-3,4-dihydrocarbostyril and its 3,4-dehydro compound 5-{6-[N-Methyl-N-(3-tetrahydropyranyl)aminocarbonyl]hexyloxy}-3,4-dihydrocarbostyril and its 3,4-dehydro compound 8-{3-[N-Ethyl-N-(4-tetrahydropyranyl)aminocarbonyl]propoxy}-3,4-dihydrocarbostyril and its 3,4-dehydro compound 6-{3-N-Ethyl-N-(2-pyrrolyl)aminocarbonyl]propoxy}-3,4-dihydrocarbostyril and its 3,4-dehydro compound 5-{3-[N-Methyl-N-(3-pyrrolyl)aminocarbonyl]propoxy}-3,4-dihydrocarbostyril and its 3,4-dehydro compound 7-{4-[N-Methyl-N-(2-pyrrolyl)aminocarbonyl]butoxy}-3,4-dihydrocarbostyril and its 3,4-dehydro compound 6-{4-[N-Methyl-N-(2-pyrrolidinyl)aminocarbonyl]butoxy}-3,4-dihydrocarbostyril and its 3,4-dehydro compound 6-{3-[N-Ethyl-N-(3-pyrrolidinyl)aminocarbonyl]propoxy}-3,4-dihydrocarbostyril and its 3,4-dehydro compound 8-{3-[N-Ethyl-N-(2-pyrrolidinyl)aminocarbonyl]propoxy}-3,4-dihydrocarbostyril and 3,4-dehydro compound 6-{3-[N-Methyl-N-(2-piperidinyl)aminocarbonyl]propoxy}-3,4-dihydrocarbostyril and 3,4-dehydro compound 5-{3-[N-Ethyl-N-(4-piperidinyl)aminocarbonyl]propoxy}-3,4-dihydrocarbostyril and 3,4-dehydro compound 7-{3-[N-Methyl-N-(3-piperidinyl)aminocarbonyl]propoxy}-3,4-dihydrocarbostyril and 3,4-dehydro compound 6-{3-[N-(2-Hydroxyethyl)-N-(2-pyridylmethyl)aminocarbonyl]propoxy}-3,4-dihydrocarbostyril and 3,4-dehydro compound 6-{3-[N-Methyl-N-(3-pyridylmethyl)aminocarbonyl]propoxy}-3,4-dihydrocarbostyril and its 3,4-dehydro compound 5-{3-[N-Ethyl-N-(2-pyridylmethyl)aminocarbonyl]propoxy}-3,4-dihydrocarbostyril and its 3,4-dehydro compound 8-{3-[N-Butyl-N-(4-pyridylmethyl)aminocarbonyl]propoxy}-3,4-dihydrocarbostyril and its 3,4-dehydro compound 6-[3-{N-Methyl-N-[4-(3-pyridyl)butyl]aminocarbonyl}propoxy]-3,4-dihydrocarbostyril and its 3,4-dehydro compound 6-{3-[N-Methyl-N-(2-furylmethyl)aminocarbonyl]propoxy}-3,4-dihydrocarbostyril and its 3,4-dehydro compound 5-[3-{N-Ethyl-N-[2-(3-furyl)ethyl]aminocarbonyl}propoxy]-3,4-dihydrocarbostyril and its 3,4-dehydro compound 7-[3-{N-Methyl-N-[4-(2-furyl)butyl]aminocarbonyl}-propoxy]-3,4-dihydrocarbostyril and its 3,4-dehydro compound 6-{3-[N-Methyl-N-(2-tetrahydrofurylmethyl)aminocarbonyl]propoxy}-3,4-dihydrocarbostyril and its 3,4-dehydro compound 6-{3-[N-(2-Hydroxyethyl)-N-(2-furylmethyl)aminocarbonyl]propoxy}-3,4-dihydrocarbostyril and its 3,4-dehydro compound 6-{3-[N-(2-Hydroxyethyl)-N-(2-tetrahydrofurylmethyl)aminocarbonyl]propoxy}-3,4-dihydrocarbostyril and its 3,4-dehydro compound 5-{2-Methyl-3-[N-methyl-(3-tetrahydrofurylmethyl)aminocarbonyl]propoxy}-3,4-dihydrocarbostyril and its 3,4-dehydro compound 8-{4-[N-Ethyl-N-(2-tetrahydrofurylmethyl)aminocarbonyl]butoxy}-3,4-dihydrocarbostyril and its 3,4-dehydro compound 6-[3-{N-Methyl-N-[5-(2-tetrahydrofuryl)pentyloxy]aminocarbonyl}propoxy]-3,4-dihydrocarbostyril and its 3,4-dehydro compound 6-{3-[N-Methyl-N-(2-2H-pyranylmethyl)aminocarbonyl]propoxy}-3,4-dihydrocarbostyril and its 3,4-dehydro compound 5-{3-[N-Ethyl-N-(3-2H-pyranylmethyl)aminocarbonyl]propoxy}-3,4-dihydrocarbostyril and its 3,4-dehydro compound 6-{3-[N-Ethyl-N-(2-4H-pyranylmethyl)aminocarbonyl]propoxy}-3,4-dihydrocarbostyril and its 3,4-dehydro compound 6-{3-[N-Methyl-N-(2-3,4-dihydro-2H-pyranylmethyl)aminocarbonyl]propoxy}-3,4-dihydrocarbostyril and its 3,4-dehydro compound 6-{3-[N-(2-Hydroxyethyl)-N-(2-3,4-dihydro-2H-pyranylmethyl)aminocarbonyl]propoxy}-3,4-dihydrocarbostyril and its 3,4-dehydro compound 6-{3-[N-(2-Hydroxyethyl)-N-(2-tetrahydropyranylmethyl)aminocarbonyl]propoxy}-3,4-dihydrocarbostyril and its 3,4-dehydro compound 5-[3-{N-Methyl-N-[2-(3-3,4-dihydro-2H-pyranyl)ethyl]aminocarbonyl}propoxy]-3,4-dihydrocarbostyril and its 3,4-dehydro compound 7-{3-[N-Methyl-N-(4-3,4-dihydro-2H-pyranylmethyl)aminocarbonyl]propoxy}-3,4-dihydrocarbostyril and its 3,4-dehydro compound 6-{3-[N-Methyl-N-(2-tetrahydropyranylmethyl)aminocarbonyl]propoxy}-3,4-dihydrocarbostyril and its 3,4-dehydro compound 5-{3-[N-Ethyl-N-(4-tetrahydropyranylmethyl)aminocarbonyl]propoxy}-3,4-dihydrocarbostyril and its 3,4-dehydro compound 8-{3-[N-Methyl-N-(3-tetrahydropyranylmethyl)aminocarbonyl]propoxy}-3,4-dihydrocarbostyril and its 3,4-dehydro compound 6-[3-{N-Methyl-N-[3-(4-tetrahydropyranyl)propyl]aminocarbonyl}propoxy]-3,4-dihydrocarbostyril and its 3,4-dehydro compound 6-{3-[N-Methyl-N-(2-thienylmethyl)aminocarbonyl]propoxy}-3,4-dihydrocarbostyril and its 3,4-dehydro compound 5-{3-[N-Ethyl-N-(3-thienylmethyl)aminocarbonyl]propoxy}-3,4-dihydrocarbostyril and its 3,4-dehydro compound 6-{3-[N-(2-Hydroxyethyl)-N-(2-thienylmethyl)aminocarbonyl]propoxy}-3,4-dihydrocarbostyril and its 3,4-dehydro compound 6-{3-[N-Methyl-N-(2-tetrahydrothienyl)aminocarbonyl]propoxy}-3,4-dihydrocarbostyril and its 3,4-dehydro compound 5-{4-[N-Methyl-N-(3-tetrahydrothienyl)aminocarbonyl]propoxy}-3,4-dihydrocarbostyril and its 3,4-dehydro compound 6-{3-[N-Methyl-N-(2-tetrahydrothiopyranylmethyl)aminocarbonyl]propoxy}-3,4-dihydrocarbostyril and its 3,4-dehydro compound 7-{2-Methyl-3-[N-methyl-N-(3-tetrahydrothiopyranylmethyl)aminocarbonyl]propoxy}-3,4-dihydrocarbostyril and its 3,4-dehydro compound 6-{3-[N-Methyl-N-(2-pyrrolylmethyl)aminocarbonyl]propoxy}-3,4-dehydrocarbostyril and its 3,4-dehydro compound 8-{3-[N-Ethyl-N-(3-pyrrolylmethyl)aminocarbonyl]propoxy}-3,4-dihydrocarbostyril and its 3,4-dehydro compound 6-{3-[N-Methyl-N-(2-pyrrolidinylmethyl)aminocarbonyl]propoxy}-3,4-dihydrocarbostyril and its 3,4-dehydro compound 6-{3-[N-(2-Hydroxyethyl)-N-(2-pyrrolidinylmethyl)aminocarbonyl]propoxy}-3,4-dihydrocarbostyril and its 3,4-dehydro compound 5-{3-[N-Ethyl-N-(3-pyrrolidinylmethyl)aminocarbonyl]propoxy}-3,4-dihydrocarbostyril and its 3,4-dehydro compound 7-[3-{N-Methyl-N-[6-(3-pyrrolidinyl)hexyl]aminocarbonyl}propoxy]-3,4-dihydrocarbostyril and its 3,4-dehydro compound 6-{3-[N-Methyl-N-(2-piperidinylmethyl)aminocarbonyl]propoxy}-3,4-dihydrocarbostyril and its 3,4-dehydro compound 5-{3-[N-Ethyl-N-(4-piperidinylmethyl)aminocarbonyl]propoxy}-3,4-dihydrocarbostyril and its 3,4-dehydro compound 8-{2-[N-Methyl-N-(3-piperidinylmethyl)aminocarbonyl]ethoxy}-3,4-dihydrocarbostyril and its 3,4-dehydro compound 6-[3-{N-Methyl-N-[4-(4-piperidinyl)butyl]aminocarbonyl}propoxy]-3,4-dihydrocarbostyril and its 3,4-dehydro compound 6-{3-[N-(2-Hydroxyethyl)-N-(4-piperidinylmethyl)aminocarbonyl]propoxy}-3,4-dihydrocarbostyril and its 3,4-dehydro compound 6-{3-[N-(2-Hydroxyethyl)-N-(2-pyrrolylmethyl)aminocarbonyl]propoxy}-3,4-dihydrocarbostyril and its 3,4-dehydro compound 6-{4-[N-(2,3-Dihydroxypropyl)-N-cyclohexylaminocarbonyl]butoxy}-3,4-dihydrocarbostyril and its 3,4-dehydro compound 5-{4-[N-(2,3-Dihydroxypropyl)-N-cyclohexylaminocarbonyl]butoxy}-3,4-dihydrocarbostyril and its 3,4-dehydro compound 6-{4-[N-(2,3-Dihydroxypropyl)-N-cyclohexylmethylaminocarbonyl]butoxy}-3,4-dihydrocarbostyril and its 3,4-dehydro compound 5-{4-N-(2-Hydroxyethyl)-N-cyclohexylaminocarbonyl]butoxy}-3,4-dihydrocarbostyril and its 3,4-dehydro compound 8-{3-[N-(2,3-Dihydroxypropyl)-N-cyclohexylaminocarbonyl]propoxy}-3,4-dihydrocarbostyril and its 3,4-dehydro compound 7-{3-[N-(2,3-Dihydroxypropyl)-N-cyclohexylaminocarbonyl]propoxy}-3,4-dihydrocarbostyril and its 3,4-dehydro compound 6-{3-[N-(2,3-Dihydroxypropyl)-N-cyclohexylaminocarbonyl]propoxy}-3,4-dihydrocarbostyril and its 3,4-dehydro compound 6-{3-[N-(2,3-Dihydroxypropyl)-N-cyclohexylmethylaminocarbonyl]propoxy}-3,4-dihydrocarbostyril and its 3,4-dehydro compound 6-{3-[N-(3,4-Dihydroxybutyl)-N-cyclohexylaminocarbonyl]propoxy}-3,4-dihydrocarbostyril and its 3,4-dehydro compound 6-{3-[N-(2,3,4-Trihydroxybutyl)-N-cyclohexylaminocarbonyl]propoxy}-3,4-dihydrocarbostyril and its 3,4-dehydro compound 5-{3-[N-(2,3-Dihydroxypropyl)-N-cyclohexylaminocarbonyl]propoxy}-3,4-dihydrocarbostyril and its 3,4-dehydro compound 6-{3-[N-(2,4-Dihydroxybutyl)-N-cyclooctylaminocarbonyl]propoxy}-3,4-dihydrocarbostyril and its 3,4-dehydro compound 6-{3-[N-(2-Hydroxyethyl)-N-(3,4-dimethoxybenzyl)aminocarbonyl]propoxy}-3,4-dihydrocarbostyril and its 3,4-dehydro compound 6-{4-[N-(2-Hydroxyethyl)-N-benzylaminocarbonyl]butoxy}-3,4-dihydrocarbostyril and its 3,4-dehydro compound 6-{4-[N-(2-Hydroxyethyl)-N-(β-3,4-dimethoxyphenethyl)aminocarbonyl]butoxy}-3,4-dihydrocarbostyril and its 3,4-dehydro compound 6-{3-[N-(4-Hydroxybutyl)-N-(β-3,4-dimethoxyphenethyl)aminocarbonyl]propoxy}-3,4-dihydrocarbostyril and its 3,4-dehydro compound 6-{3-[N-(2-Hydroxyethyl)-N-benzylaminocarbonyl]propoxy}-3,4-dihydrocarbostyril and its 3,4-dehydro compound 6-{3-[N-(2-Hydroxyethyl)-N-(β-phenethyl)aminocarbonyl]propoxy}-3,4-dihydrocarbostyril and its 3,4-dehydro compound 6-[4-{N-(2-Hydroxyethyl)-N-[4-(3,4-dimethoxyphenyl)butyl]aminocarbonyl}butoxy]-3,4-dihydrocarbostyril and its 3,4-dehydro compound 5-{3-[N-(2-Hydroxyethyl)-N-(β-phenethyl)aminocarbonyl]propoxy}-3,4-dihydrocarbostyril and its 3,4-dehydro compound 7-{3-[N-(2-Hydroxyethyl)-N-(β-3,4-dimethoxyphenethyl)aminocarbonyl]propoxy}-3,4-dihydrocarbostyril and its 3,4-dehydro compound 8-{3-[N-(2-Hydroxyethyl)-N-(β-3,4-dimethoxyphenethyl)aminocarbonyl]propoxy}-3,4-dihydrocarbostyril and its 3,4-dehydro compound 5-{3-[N-(4-Hydroxybutyl)-N-6-phenylhexylaminocarbonyl]butoxy}-3,4-dihydrocarbostyril and its 3,4-dehydro compound 6-{3-[N-(2,3-Dihydroxypropyl)-N-(β-3,4-dimethoxyphenethyl)aminocarbonyl]propoxy}-3,4-dihydrocarbostyril and its 3,4-dehydro compound 6-{3-[N-(3,4-Dihydroxybutyl)-N-(α-phenethyl)aminocarbonyl]propoxy}-3,4-dihydrocarbostyril and its 3,4-dehydro compound 6-{3-[N-(2-Hydroxyethyl)-N-phenylaminocarbonyl]propoxy}-3,4-dihydrocarbostyril and its 3,4-dehydro compound 6-{3-[N-(3-Hydroxypropyl)-N-phenylaminocarbonyl]propoxy}-3,4-dihydrocarbostyril and its 3,4-dehydro compound 6-{3-[N-(2,3-Dihydroxypropyl)-N-phenylaminocarbonyl]propoxy}-3,4-dihydrocarbostyril and its 3,4-dehydro compound 6-{4-[N-(2-Hydroxypropyl)-N-phenylaminocarbonyl]butoxy}-3,4-dihydrocarbostyril and its 3,4-dehydro compound 5-{4-[N-(2-Hydroxypropyl)-N-phenylaminocarbonyl]butoxy}-3,4-dihydrocarbostyril and its 3,4-dehydro compound 5-{3-[N-(4-Hydroxybutyl)-N-phenylaminocarbonyl]propoxy}-3,4-dihydrocarbostyril and its 3,4-dehydro compound 6-{4-[N-(4-Hydroxybutyl)-N-cyclohexymethylaminocarbonyl]butoxy}-3,4-dihydrocarbostyril and its 3,4-dehydro compound 6-{4-[N-(2-Hydroxyethyl)-N-cyclohexylmethylaminocarbonyl]butoxy}-3,4-dihydrocarbostyril and its 3,4-dehydro compound 7-{3-[N-(2-Hydroxyethyl)-N-phenylaminocarbonyl]butoxy}-3,4-dihydrocarbostyril and its 3,4-dehydro compound 8-{3-[N-(2-Hydroxyethyl)-N-phenylaminocarbonyl]propoxy}-3,4-dihydrocarbostyril and its 3,4-dehydro compound 6-{3-[N-(2-Hydroxypropyl)-N-cyclohexylmethylaminocarbonyl]propoxy}-3,4-dihydrocarbostyril and its 3,4-dehydro compound 6-{4-[N-(2-Hydroxypropyl)-N-(4-cyclohexylbutyl)aminocarbonyl]butoxy}-3,4-dihydrocarbostyril and its 3,4-dehydro compound 5-{3-[N-(2-Hydroxypropyl)-N-(3-cyclohexylpropyl)aminocarbonyl]propoxy}-3,4-dihydrocarbostyril and its 3,4-dehydro compound 6-[3-(N-Methoxymethyl-N-cyclohexylaminocarbonyl)propoxy}-3,4-dihydrocarbostyril and its 3,4-dehydro compound 6-{3-[N-(2-Ethoxyethyl)-N-cyclohexylaminocarbonyl]propoxy}-3,4-dihydrocarbostyril and its 3,4-dehydro compound 6-{3-[N-(2-Methoxyethyl)-N-cyclohexylaminocarbonyl]propoxy}-3,4-dihydrocarbostyril and its 3,4-dehydro compound 6-{3-[N-(4-Butoxybutyl)-N-cyclohexylaminocarbonyl]propoxy}-3,4-dihydrocarbostyril and its 3,4-dehydro compound 6-{3-[N-(2-Methoxyethyl)-N-cyclooctylaminocarbonyl]propoxy}-3,4-dihydrocarbostyril and its 3,4-dehydro compound 6-{3-[N-(2-Methoxyethyl)-N-cyclopropylaminocarbonyl]propoxy}-3,4-dihydrocarbostyril and its 3,4-dehydro compound 6-{3-[N-(2-Methoxyethyl)-N-(β-3,4-dimethoxyphenethylaminocarbonyl]propoxy}-3,4-dihydrocarbostyril and its 3,4-dehydro compound 5-{3-[N-(2-Methoxyethyl)-N-cyclohexylaminocarbonyl]propoxy}-3,4-dihydrocarbostyril and its 3,4-dehydro compound 5-{4-[N-(2-Methoxyethyl)-N-cyclohexylaminocarbonyl]butoxy}-3,4-dihydrocarbostyril and its 3,4-dehydro compound 8-{3-[N-(2-Methoxyethyl)-N-cyclohexylaminocarbonyl]propoxy}-3,4-dihydrocarbostyril and its 3,4-dehydro compound 6-{4-[N-(3-Acetyloxypropyl)-N-cyclohexylaminocarbonyl]butoxy}-3,4-dihydrocarbostyril and its 3,4-dehydro compound 5-{3-[N-(2-Methoxyethyl)-N-(β-3,4-dimethoxyphenethyl)aminocarbonyl]propoxy}-3,4-dihydrocarbostyril and its 3,4-dehydro compound 6-{3-[N-(2-Benzoyloxyethyl)-N-cyclohexylaminocarbonyl]propoxy}-3,4-dihydrocarbostyril and its 3,4-dehydro compound
6-{3-[N-(6-Benzoyloxyhexyl)-N-cyclohexylaminocarbonyl]propoxy}-3,4-dihydrocarbostyril and its 3,4-dehydro compound
6-{4-[N-(2-Benzoyloxyethyl)-N-cyclohexylaminocarbonyl]butoxy}-3,4-dihydrocarbostyril and its 3,4-dehydro compound
6-{4-[N-(5-Propionyloxyheptyl)-N-cyclohexylmethylaminocarbonyl]butoxy}-3,4-dihydrocarbostyril and its 3,4-dehydro compound
6-{4-[N-(3-Acetyloxypropyl)-N-(2-tetrahydropyranylmethyl)aminocarbonyl]butoxy}-3,4-dihydrocarbostyril and its 3,4-dehydro compound
6-{3-[N-(6-Hexyloxyphenyl)-N-cyclohexylaminocarbonyl]propoxy}-3,4-dihydrocarbostyril and its 3,4-dehydro compound
6-{3-[N-(5-Propionyloxyheptyl)-N-cyclohexylmethylaminocarbonyl]propoxy}-3,4-dihydrocarbostyril and its 3,4-dehydro compound
7-{3-[N-(2-Benzoyloxyethyl)-N-cyclohexylaminocarbonyl]propoxy}-3,4-dihydrocarbostyril and its 3,4-dehydro compound
5-{3-[N-(2-Benzoyloxyethyl)-N-cyclohexylaminocarbonyl]propoxy}-3,4-dihydrocarbostyril and its 3,4-dehydro compound
6-{3-[N-(2-Hydroxyethyl)-N-(3-hydroxycyclohexyl)aminocarbonyl]propoxy}-3,4-dihydrocarbostyril and its 3,4-dehydro compound
6-{3-[N-(6-Hydroxyhexyl)-N-(3-hydroxycyclohexyl)aminocarbonyl]propoxy}-3,4-dihydrocarbostyril and its 3,4-dehydro compound
6-{3-[N-(2-Hydroxyethyl)-N-(2-hydroxycyclohexyl)aminocarbonyl]propoxy}-3,4-dihydrocarbostyril and its 3,4-dehydro compound
6-{3-[N-(2-Hydroxyethyl)-N-(4-hydroxycyclohexyl)aminocarbonyl]propoxy}-3,4-dihydrocarbostyril and its 3,4-dehydro compound
6-{3-[N-(2-Hydroxyethyl)-N-(3-hydroxycyclohexyl)aminocarbonyl]propoxy}-3,4-dihydrocarbostyril and its 3,4-dehydro compound
5-{3-[N-(2-Hydroxyethyl)-N-(3-hydroxycyclohexyl)aminocarbonyl}propoxy}-3,4-dihydrocarbostyril and its 3,4-dehydro compound
5-{3-[N-(2-Hydroxyethyl)-N-(3-hydroxycyclohexyl)aminocarbonyl]propoxy}-3,4-dihydrocarbostyril and its 3,4-dehydro compound
6-[3-(4-Phenyl-1-piperazinylcarbonyl)propoxy]-3,4-dihydrocarbostyril and its 3,4-dehydro compound
6-[3-(4-Phenyl-1-piperidinylcarbonyl)propoxyl]-3,4-dihydrocarbostyril and its 3,4-dehydro compound
6-[3-(4-Cyclohexyl-1-piperazinylcarbonyl)propoxy]-3,4-dihydrocarbostyril and its 3,4-dehydro compound
6-[3-(4-Benzyl-1-piperidinylcarbonyl)propoxy]-3,4-dihydrocarbostyril and its 3,4-dehydro compound
6-[3-(4-Benzyl-1-piperazinylcarbonyl)propoxy]-3,4-dihydrocarbostyril and its 3,4-dehydro compound
5-[3-(4-Phenyl-1-piperazinylcarbonyl)propoxy]-3,4-dihydrocarbostyril and its 3,4-dehydro compound
7-[3-(4-Phenyl-1-piperazinylcarbonyl)propoxy]-3,4-dihydrocarbostyril and its 3,4-dehydro compound
8-[3-(4-Phenyl-1-piperazinylcarboxyl)propoxy]-3,4-dihydrocarbostyril and its 3,4-dehydro compound
1-Methyl-6-{3-[N-(2-hydroxyethyl)-N-cyclohexylaminocarbonyl]propoxy}-3,4-dihydrocarbostyril and its 3,4-dehydro compound
1-Hexyl-6-{3-[N-(2-hydroxyethyl)-N-cyclohexylaminocarbonyl]propoxy}-3,4-dihydrocarbostyril and its 3,4-dehydro compound
1-Allyl-6-{3-[N-(2-hydroxyethyl)-N-cyclohexylaminocarbonyl]propoxy}-3,4-dihydrocarbostyril and its 3,4-dehydro compound
1-(2-Hexenyl)-6-{3-[N-(2-hydroxyethyl)-N-cyclohexylaminocarbonyl]propoxy}-3,4-dihydrocarbostyril and its 3,4-dehydro compound
1-Benzyl-6-{3-[N-(2-hydroxyethyl)-N-cyclohexylaminocarbonyl]propoxy}-3,4-dihydrocarbostyril and its 3,4-dehydro compound
1-(6-Phenylhexyl)-6-{3-[N-(2-hydroxyethyl)-N-cyclohexylaminocarbonyl]propoxy}-3,4-dihydrocarbostyril and its 3,4-dehydro compound
1-Methyl-5-{3-[N-(2-hydroxyethyl)-N-cyclohexylaminocarbonyl]propoxy}-3,4-dihydrocarbostyril and its 3,4-dehydro compound
1-Benzyl-5-{3-[N-(2-hydroxyethyl)-N-cyclohexylaminocarbonyl]propoxy}-3,4-dihydrocarbostyril and its 3,4-dehydro compound
1-Methyl-7-{3-[N-(2-hydroxyethyl)-N-cyclohexylaminocarbonyl]propoxy}-3,4-dihydrocarbostyril and its 3,4-dehydro compound
1-Methyl-8-{3-[N-(2-hydroxyethyl)-N-cyclohexylaminocarbonyl]propoxy}-3,4-dihydrocarbostyril and its 3,4-dehydro compound
1-Methyl-6-{3-[N-methyl-N-(4-pyridyl)aminocarbonyl]propoxy}-3,4-dihydrocarbostyril and its 3,4-dehydro compound
1-Methyl-6-{3-[N-methyl-N-(2-furyl)aminocarbonyl]propoxy}-3,4-dihydrocarbostyril and its 3,4-dehydro compound
1-Methyl-5-{2-methyl-[N-(2-tetrahydrofuryl)aminocarbonyl]propoxy}-3,4-dihydrocarbostyril and its 3,4-dehydro compound
1-Methyl-7-{3-[N-methyl-N-(2-2H-pyranyl)aminocarbonyl]propoxy}-3,4-dihydrocarbostyril and its 3,4-dehydro compound
1-Methyl-6-[3-(4-phenyl-1-piperazinylcarbonyl)propoxy]-3,4-dihydrocarbostyril and its 3,4-dehydro compound
1-Benzyl-5-[3-(4-phenyl-1-piperidylcarbonyl)propoxy]-3,4-dihydrocarbostyril and its 3,4-dehydro compound
4-Methyl-6-{3-[N-(2-hydroxyethyl)-N-cyclohexylaminocarbonyl]propoxy}-3,4-dihydrocarbostyril and its 3,4-dehydro compound
4-Ethyl-6-{3-[N-(2-hydroxyethyl)-N-cyclohexylaminocarbonyl]propoxy}-3,4-dihydrocarbostyril and its 3,4-dehydro compound
4-Hexyl-6-{3-[N-(2-hydroxyethyl)-N-cyclohexylaminocarbonyl]propoxy}-3,4-dihydrocarbostyril and its 3,4-dehydro compound
1,4-Dimethyl-6-{3-[N-(2-hydroxyethyl)-N-cyclohexylaminocarbonyl]propoxy}-3,4-dihydrocarbostyril and its 3,4-dehydro compound
1-Hexyl-4-methyl-7-{3-[N-(2-hydroxyethyl)-N-cyclohexylaminocarbonyl]propoxy}-3,4-dihydrocarbostyril and its 3,4-dehydro compound
1-Benzyl-4-methyl-8-{3-[N-(2-hydroxyethyl)-N-cyclohexylaminocarbonyl]propoxy}-3,4-dihydrocarbostyril and its 3,4-dehydro compound
6-{3-[N-(2-Hydroxyethyl)-N-ethylaminocarbonyl]propoxy}-3,4-dihydrocarbostyril and its 3,4-dehydro compound 6-{3-[N,N-Di-(2-hydroxyethyl)aminocarbonyl]-propoxy}-3,4-dihydrocarbostyril and its 3,4-dehydro compound 5-{3-[N-(2-Hydroxyethyl)-N-cyclohexylmethylaminocarbonyl]propoxy}-3,4-dihydrocarbostyril and its 3,4-dehyo compound 5-{4-[N-(2-hydroxyethyl)-N-cyclohexylmethylaminocarbonyl]butoxy}-3,4-dihydrocarbostyril and its 3,4-dehydro compound 6-{4-[N-(2-Methoxyethyl)-N-cyclohexylaminocarbonyl]butoxy}-3,4-dihydrocarbostyril and its 3,4-dehydro compound 6-{3-[N-(2-Methoxyethyl)-N-cyclohexylmethylaminocarbonyl]propoxy}-3,4-dihydrocarbostyril and its 3,4-dehydro compound 6-{4-[N-(2-Ethoxyethyl)-N-cyclohexylaminocarbonyl]butoxy}-3,4-dihydrocarbostyril and its 3,4-dehydro compound 6-{3-[N-(2-Methoxyethyl)-N-phenylaminocarbonyl]propoxy}-3,4-dihydrocarbostyril and its 3,4-dehydro compound 6-{4-[N-(2-Ethoxyethyl)-N-(2-hydroxyethyl)aminocarbonyl]butoxy}-3,4-dihydrocarbostyril and its 3,4-dehydro compound 6-{3-[N-(2-Methoxyethyl)-N-ethylaminocarbonyl]propoxy}-3,4-dihydrocarbostyril and its 3,4-dehydro compound 6-{4-[N-(2-Methoxyethyl)-N-(β-phenethyl)aminocarbonyl]butoxy}-3,4-dihydrocarbostyril and its 3,4-dehydro compound 6-{3-[N-(2-Hydroxyethyl)-N-(β-3,4-dimethoxyphenethyl)aminocarbonyl]propoxy}-3,4-dihydrocarbostyril and its 3,4-dehydro compound 5-{3-[N-(2-Hydroxyethyl)-N-(β-3,4-dimethoxyphenethyl)aminocarbonyl]propoxy}-3,4-dihydrocarbostyril and its 3,4-dehydro compound 6-{4-[N-(2-Hydroxyethyl)-N-(β-3,4-diethoxyphenethyl)aminocarbonyl]butoxy}-3,4-dihydrocarbostyril and its 3,4-dehydro compound 6-{3-[N-(2-Hydroxyethyl)-N-(β-3,4,5-trimethoxyphenethyl)aminocarbonyl]propoxy}-3,4-dihydrocarbostyril and its 3,4-dehydro compound 6-{5-[N-(2-Hydroxyethyl)-N-benzylaminocarbonyl]pentyloxy}-3,4-dihydrocarbostyril and its 3,4-dehydro compound 6-{3-[N-(2-Hydroxyethyl)-N-(β-4-methoxyphenethyl)aminocarbonyl]propoxy}-3,4-dihydrocarbostyril and its 3,4-dehydro compound 6-{3-[N-(2-Hydroxyethyl)-N-cyclohexylmethylaminocarbonyl]propoxy}-3,4-dihydrocarbostyril and its 3,4-dehydro compound 6-{3-[N-(2-Hydroxyethyl)-N-cycloctylmethylaminocarbonyl]propoxy}-3,4-dihydrocarbostyril and its 3,4-dehydro compound 6-{4-[N-(2-hydroxyethyl)-N-cyclodecanylmethylaminocarbonyl]propoxy}-3,4-dihydrocarbostyril and its 3,4-dehydro compound 6-{3-[N-(2-Benzoyloxyethyl)-N-cyclohexylmethylaminocarbonyl]propoxy}-3,4-dihydrocarbostyril and its 3,4-dehydro compound 6-{4-[N-(2-Benzoyloxyethyl)-N-phenylaminocarbonyl]butoxy}-3,4-dihydrocarbostyril and its 3,4-dehydro compound 6-{3-[N-(2-Benzoyloxyethyl)-N-(β-3,4-dimethoxyphenethyl)aminocarbonyl]propoxy}-3,4-dihydrocarbostyril and its 3,4-dehydro compound 6-{4-[N-(2-Benzoyloxyethyl)-N-(2-hydroxyethyl)aminocarbonyl]butoxy}-3,4-dihydrocarbostyril and its 3,4-dehydro compound 6-{3-[N-(2-Acetyloxyethyl)-N-cyclohexylaminocarbonyl]propoxy}-3,4-dihydrocarbostyril and its 3,4-dehydro compound 6-{4-[N-(2-Acetyloxyethyl)-N-cyclohexylaminocarbonyl]butoxy}-3,4-dihydrocarbostyril and its 3,4-dehydro compound 6-{3-[N-(2-Propionyloxyethyl)-N-cyclohexylaminocarbonyl]propoxy}-3,4-dihydrocarbostyril and its 3,4-dehydro compound 5-{4-[4-(2-Acetyloxyethyl)-N-cyclohexylaminocarbonyl]butoxy}-3,4-dihydrocarbostyril and its 3,4-dehydro compound 6-{4-(N-(2-Acetyloxyethyl)-N-cyclohexymethylaminocarbonyl]butoxy}-3,4-dihydrocarbostyril and its 3,4-dehydro compound 6-{3-[N-(2-Acetyloxyethyl)-N-(β-3,4-dimethoxyphenethyl)aminocarbonyl]propoxy}-3,4-dihydrocarbostyril and its 3,4-dehydro compound 6-{4-[N-(2-Acetyloxyethyl)-N-phenylaminocarbonyl]butoxy}-3,4-dihydrocarbostyril and its 3,4-dehydro compound 6-{4-[N-(2-Acetyloxyethyl)-N-(2-tetrahydropyranylmethyl)aminocarbonyl]butoxy}-3,4-dihydrocarbostyril and its 3,4-dehydro compound 6-{3-[N-(2-Methoxyethyl)-N-(2-tetrahydropyranylmethyl)aminocarbonyl]propoxy}-3,4-dehydrocarbostyril and its 3,4-dehydro compound 6-{3-[N-(2-Benzoyloxyethyl)-N-(2-tetrahydropyranylmethyl)aminocarbonyl]propoxy}-3,4-dihydrocarbostyril and its 3,4-dehydro compound 6-{4-[N-(2-hydroxyethyl)-N-(2-tetrahydropyranylmethyl)aminocarbonyl]butoxy}-3,4-dihydrocarbostyril and its 3,4-dehydro compound 6-{3-[N-(3-Hydroxypropyl)-N-(2-tetrahydropyranylmethyl)aminocarbonyl]propoxy}-3,4-dihydrocarbostyril and its 3,4-dehydro compound 6-{4-[N-(2-Hydroxyethyl)-N-(2-tetrahydropyranyl)aminocarbonyl]butoxy}-3,4-dihydrocarbostyril and its 3,4-dehydro compound 6-{3-[N-(2-Methoxyethyl)-N-(2-tetrahydropyranyl)aminocarbonyl]propoxy}-3,4-dihydrocarbostyril and its 3,4-dehydro compound 6-{3-[N-(2-Acetyloxyethyl)-N-(2-tetrahydropyranyl)aminocarbonyl]propoxy}-3,4-dihydrocarbostyril and its 3,4-dehydro compound 6-{3-[N-(2,3-Dihydroxypropyl)-N-(2-tetrahydropyranylmethyl)aminocarbonyl]propoxy}-3,4-dihydrocarbostyril and its 3,4-dehydro compound 6-{4-[N-(2-Hydroxyethyl)-N-(3-hydroxycyclohexyl)aminocarbonyl]butoxy}-3,4-dihydrocarbostyril and its 3,4-dehydro compound 6-{4-[N-(2-Hydroxyethyl)-N-(4-hydroxycyclohexyl)aminocarbonyl]butoxy}-3,4-dihydrocarbostyril and its 3,4-dehydro compound 6-{4-[N-(2-Hydroxyethyl)-N-(2-hydroxycyclohexyl)aminocarbonyl]butoxy}-3,4-dihydrocarbostyril and its 3,4-dehydro compound 6-{3-[N-(2,3-Dihydroxypropyl)-N-(3-hydroxycyclohexyl)aminocarbonyl]propoxy}-3,4-dihydrocarbostyril and its 3,4-dehydro compound 6-{4-[N-(2,3-Dihydroxypropyl)-N-(3-hydroxycyclohexyl)aminocarbonyl]butoxy}-3,4-dihydrocarbostyril and its 3,4-dehydro compound 6-{3-[N-(2-Methoxyethyl)-N-(3-hydroxycyclohexyl)aminocarbonyl]propoxy}-3,4-dihydrocarbostyril and its 3,4-dehydro compound 6-{4-[N-(2-Acetyloxyethyl)-N-(3-hydroxycyclohexyl)aminocarbonyl]butoxy}-3,4-dihydrocarbostyril and its 3,4-dehydro compound 6-{3-[N-(2-Benzoyloxyethyl)-N-(3-hydroxycyclohexyl)aminocarbonyl]propoxy}-3,4-dihydrocarbostyril and its 3,4-dehydro compound 6-{3-[N-(2-Hydroxyethyl)-N-(3,4-dihydrocyclohexyl)aminocarbonyl]propoxy}-3,4-dihydrocarbostyril and its 3,4-dehydro compound 6-{3-[N-(2-Hydroxyethyl)-N-(3,4,5-trihydroxycyclohexyl)aminocarbonyl]propoxy}-3,4-dihydrocarbostyril and its 3,4-dehydro compound 6-{4-[N-(2-Hydroxyethyl)-N-(4-hydroxycyclooctyl)aminocarbonyl]butoxy}-3,4-dihydrocarbostyril and its 3,4-dehydro compound 6-[3-(4-Cyclooctyl-1-piperazinylcarbonyl)propoxy]-3,4-dihydrocarbostyril and its 3,4-dehydro compound 6-[4-(4-Phenyl-1-piperazinylcarbonyl)butoxy]-3,4-dihydrocarbostyril and its 3,4-dehydro compound 6-[4-(4-Cyclohexyl-1-piperazinylcarbonyl)butoxy]-3,4-dihydrocarbostyril and its 3,4-dehydro compound 6-[4-(4-β-Phenethyl-1-piperazinylcarbonyl)butoxy]-3,4-dihydrocarbostyril and its 3,4-dehydro compound 5-[4-(4-Phenyl-1-piperazinylcarbonyl)butoxy]-3,4-dihydrocarbostyril and its 3,4-dehydro compound 6-[3-(4-Phenyl-1-piperidylcarbonyl)propoxy]-3,4-dihydrocarbostyril and its 3,4-dehydro compound 6-[4-(4-Phenyl-1-piperidylcarbonyl)butoxy]-3,4-dihydrocarbostyril and its 3,4-dehydro compound 5-[3-(4-Phenyl-1-piperidylcarbonyl)propoxy]-3,4-dihydrocarbostyril and its 3,4-dehydro compound 6-[3-(4-Cyclohexyl-1-piperidylcarbonyl)propoxy]-3,4-dihydrocarbostyril and its 3,4-dehydro compound 6-[3-(4-Benzyl-1-piperidylcarbonyl)propoxy]-3,4-dihydrocarbostyril and its 3,4-dehydro compound 6-[3-(4-β-Phenethyl-1-piperidylcarbonyl)propoxy]-3,4-dihydrocarbostyril and its 3,4-dehydro compound 4-Methyl-6-{3-[N-(2-hydroxyethyl)-N-cyclohexylaminocarbonyl]propoxy}-3,4-dihydrocarbostyril and its 3,4-dehydro compound 4-Methyl-6-{3-[N-(2-hydroxyethyl)-N-(2-tetrahydropyranylmethyl)aminocarbonyl]propoxy}-3,4-dihydrocarbostyril and its 3,4-dehydro compound 4-Methyl-6-{4-[N-(2-hydroxyethyl)-N-(β-3,4-dimethoxyphenethyl)aminocarbonyl]butoxy}-3,4-dihydrocarbostyril and its 3,4-dehydro compound 4-Methyl-6-{3-[N-(2-hydroxypropyl)-N-cyclohexylmethylaminocarbonyl]propoxy}-3,4-dihydrocarbostyril and its 3,4-dehydro compound 4-Methyl-5-{3-[N-(2-hydroxyethyl)-N-cyclohexylaminocarbonyl]propoxy}-3,4-dihydrocarbostyril and its 3,4-dehydro compound 4-Methyl-6-{4-[N-(3-hydroxypropyl)-N-phenylaminocarbonyl]butoxy}-3,4-dihydrocarbostyril and its 3,4-dehydro compound 4-Methyl-6-[3-(4-phenyl-1-piperazinylcarbonyl)propoxy]-3,4-dihydrocarbostyril and its 3,4-dehydro compound 4-Methyl-6-{3-[N-(2-methoxyethyl)-N-cyclohexylaminocarbonyl]propoxy}-3,4-dihydrocarbostyril and its 3,4-dehydro compound 4-Methyl-6-{4-[N-(2-acetyloxyethyl)-N-cyclohexylaminocarbonyl]butoxy}-3,4-dihydrocarbostyril and its 3,4-dehydro compound 4-Methyl-6-{3-[N-(2-benzoyloxyethyl)-N-cyclohexylaminocarbonyl]propoxy}-3,4-dihydrocarbostyril and its 3,4-dehydro compound 4-Methyl-6-{3-[N-(2-hydroxyethyl)-N-(3-hydroxycyclohexyl)aminocarbonyl]propoxy}-3,4-dihydrocarbostyril and its 3,4-dehydro compound 4-{3-[N-(2-Hydroxyethyl)-N-cyclohexylaminocarbonyl]propoxy}-3,4-dihydrocarbostyril and its 3,4-dehydro compound 4-{4-[N-(2-Hydroxyethyl)-N-(cyclohexylmethylaminocarbonyl]butoxy}-3,4-dihydrocarbostyril and its 3,4-dehydro compound 4-{3-[N-(2-Hydroxyethyl)-N-(3-hydroxycyclohexyl)aminocarbonyl]propoxy}-3,4-dihydrocarbostyril and its 3,4-dehydro compound 4-{4-[N-(2-hydroxyethyl)-N-(β-3,4-dimethoxyphenethyl)aminocarbonyl]butoxy}-3,4-dihydrocarbostyril and its 3,4-dehydro compound 4-{3-[N-(2-Hydroxyethyl)-N-(2-tetrahydropyranylmethyl)aminocarbonyl]propoxy}-3,4-dihydrocarbostyril and its 3,4-dehydro compound 4-{4-[N-(2-Hydroxyethyl)-N-phenylaminocarbonyl]butoxy}-3,4-dihydrocarbostyril and its 3,4-dehydro compound 4-{3-[N-(2-Methoxyethyl)-N-cyclohexylaminocarbonyl]propoxy}-3,4-dihydrocarbostyril and its 3,4-dehydro compound 4-{4-[N-(2-Methoxyethyl)-N-(2-tetrahydropyranylmethyl)aminocarbonyl]butoxy}-3,4-dihydrocarbostyril and its 3,4-dehydro compound 4-{3-[N-(2-Methoxyethyl)-N-cyclohexylmethylaminocarbonyl]propoxy}-3,4-dihydrocarbostyril and its 3,4-dehydro compound 4-{4-[N-(2-Methoxyethyl)-N-(3-hydroxycyclohexyl)aminocarbonyl]butoxy}-3,4-dihydrocarbostyril and its 3,4-dehydro compound 4-{3-[N-(2-Acetyloxyethyl)-N-cyclohexylaminocarbonyl]propoxy}-3,4-dihydrocarbostyril and its 3,4-dehydro compound 4-{4-[N-(2-Acetyloxyethyl)-N-(3-hydroxycyclohexyl)aminocarbonyl]butoxy}-3,4-dihydrocarbostyril and its 3,4-dehydro compound 4-{3-[N-(2-Acetyloxyethyl)-N-(2-tetrahydropyranylmethyl)aminocarbonyl]propoxy}-3,4-dihydrocarbostyril and its 3,4-dehydro compound 4-{4-[N-(2-Benzoyloxyethyl)-N-cyclohexylaminocarbonyl]butoxy}-3,4-dihydrocarbostyril and its 3,4-dehydro compound 4-{3-[N-(2-Hydroxyethyl)-N-(2-tetrahydropyranyl)aminocarbonyl]propoxy}-3,4-dihydrocarbostyril and its 3,4-dehydro compound 1-Methyl-6-{3-[N-(2-hydroxyethyl)-N-(2-tetrahydropyranylmethyl)aminocarbonyl]propoxy}-3,4-dihydrocarbostyril and its 3,4-dehydro compound 1-Methyl-6-{4-[N-(2-methoxyethyl)-N-cyclohexylaminocarbonyl]butoxy}-3,4-dihydrocarbostyril and its 3,4-dehydro compound 1-Methyl-6-{4-[N-(2-hydroxyethyl)-N-(3-hydroxycyclohexyl)aminocarbonyl]butoxy}-3,4-dihydrocarbostyril and its 3,4-dehydro compound 1-Benzyl-6-{4-[N-(2-acetyloxyethyl)-N-cyclohexylaminocarbonyl]butoxy}-3,4-dihydrocarbostyril and its 3,4-dehydro compound 1-Allyl-6-{3-[N-(2-hydroxyethyl)-N-(β-3,4-dimethoxyphenethyl)aminocarbonyl]propoxy}-3,4-dihydrocarbostyril and its 3,4-dehydro compound 1-Methyl-6-{3-[N-(2-hydroxypropyl)-N-cyclohexylmethylaminocarbonyl]propoxy}-3,4-dihydrocarbostyril and its 3,4-dehydro compound 1-Methyl-6-{4-[N-(2-hydroxyethyl)-N-phenylaminocarbonyl]butoxy}-3,4-dihydrocarbostyril and its 3,4-dehydro compound 1-Benzyl-6-{3-[N-(2-benzoyloxyethyl)-N-cyclohexylaminocarbonyl]propoxy}-3,4-dihydrocarbostyril and its 3,4-dehydro compound The compound (1) of the present invention can be produced according to various processes such as for example expressed by the following reaction process formulas.

Reaction process formula-1

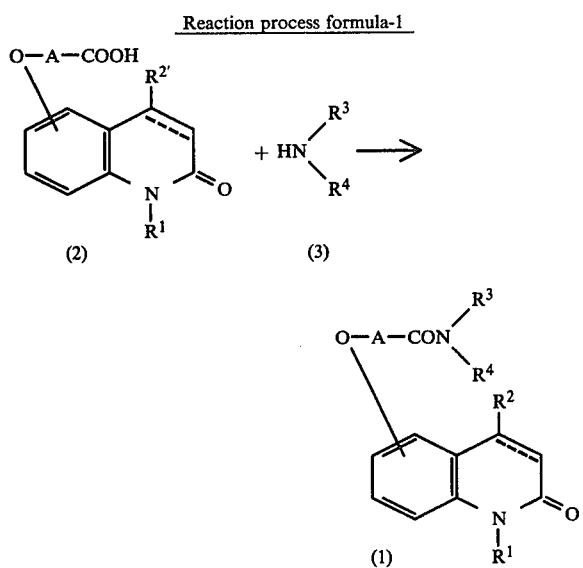

wherein $R^1$, $R^2$, $R^3$, $R^4$, A, the carbon-carbon bond between 3- and 4-positions in the carbostyril skeleton, and the substituted position of the group of the formula

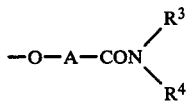

are the same as defined previously; $R^{2'}$ is a hydrogen atom, a lower alkyl group or a group of the formula —O—A—COOH (wherein A is the same as defined above); and the substituted position of the group of the formula —O—A—COOH is any one of 5-, 6-, 7- or 8-position in the carbostyril skeleton; when the group of the formula —O—A—COOH is substituted at 5-, 6-, 7- or 8-position in the carobstyril skeleton, then $R^{2'}$ is a hydrogen atom or a lower alkyl group; alternatively, when $R^{2'}$ is a group of the formula —O—A—COOH, then the 5-, 6-, 7- and 8-positions in the carbostyril skeleton are hydrogen atoms, and are not substituted with groups of the formula —O—A—COOH.

The process expressed by the reaction process formula-1 is a method for reacting a carobxyalkoxycarbostyril derivative represented by the general formula (2) with an amine represented by the general formula (3) according to an ordinary mode of amide bond forming reaction. The compound of the general formula (2) used in the invention may be substituted by a compound in which the carboxy groups were activated. The known amide bond forming reaction conditions may be easily applied to the practice of the amide bond forming reaction in the present invention. For instance, the following methods are available for said reaction: (a) mixed acid anhydride method, thus an alkylhalocarboxylic acid is reacted with a carboxylic acid (2) to form a mixed acid anhydride and the latter is further reacted with an amine (3); (b) active ester method, thus a carboxylic acid (2) is converted into an active ester such as p-nitrophenyl ester, N-hydroxysuccinic acid imidoester, 1-hydroxybenzotriazole ester or the like and then such active ester is reacted with an amine (3); (c) carbodiimide method, thus an amine (3) is reacted with a carboxylic acid (2) in the presence of an activating agent such as dicyclohexylcarbodiimide, carbonyldiimidazole or the like, to effect condensation reaction; (d) other methods, thus a carboxylic acid (2) is converted into a carboxylic acid anhydride with a dehydrating agent such as acetic acid anhydride and then thus formed carboxylic acid anhydride is reacted with an amine (3); high pressure and high temperature method, thus an amine (3) is reacted with an ester of a carboxylic acid (2) with a lower alcohol under a high pressure and high temperature condition; a method of reacting an amine (3) is reacted with an acid halide of a carboxylic acid (2), namely a carboxylic acid halide. Most preferable method among these methods is mixed acid anhydride method. The alkylhalocarboxylic acid used in the mixed acid anhydride method may be for example methyl chloroformate, methyl bromoformate, ethyl chloroformate, ethyl bromoformate, isobutyl chloroformate or the like. The mixed acid anhydride may be obtained by an usual Schotten-Baumann reaction, and this substance, usually without isolation, is reacted with an amine (3) to produce the compound of the present invention. The Schotten-Baumann reaction is carried out in the presence of a basic compound. Such basic compound may be commonly used for the Schotten-Baumann reactions and may be for example an organic base such as triethylamine, trimethylamine, pyridine, dimethylaniline, N-methylmorpholine, 1,5-diazabicyclo[4,3,0]nonene-5 (DBN), 1,5-diazabicyclo[5,4,0]undecene-5 (DBU), 1,4-diazabicyclo[2,2,2]octane (DABCO) or the like; or an inorganic base such as potassium carbonate, sodium carbonate, potassium hydrogencarbonate, sodium hydrogencarbonate or the like. Said reaction is usually carried out at a temperature within the range of −20° to 100° C., preferably at 0° to 50° C., for the period of 5 minutes to 10 hours, preferably 5 minutes to 2 hours. The reaction between the obtained mixed acid anhydride and an amine (3) is carried out at a temperature of −20° to 150° C., preferably at 10° to 50° C., for the period of 5 minutes to 10 hours, preferably for 5 minutes to 5 hours. The mixed acid anhydride method is usually carried out in a solvent. Any type of solvent commonly used in the mixed acid anhydride method may be employed, for example halogenated hydrocarbons such as methylene chloride, chloroform, dichloroethane or the like; aromatic hydrocarbons such as benzene, toluene, xylene or the like; ethers such as diethyl ether, tetrahydrofuran, dimethoxyethane or the like; esters such as methyl acetate, ethyl acetate or the like; and aprotic polar solvents such as N,N-dimethylformamide, dimethylsulfoxide, hexamethylphosphoric acid triamide or the like. In this method, the carboxylic acid (2), alkylhalocarboxylic acid and amine (3) are usually used in the equimolar ratio to each other, but the alkylhalocarboxylic acid and amine (3) may be used in 1 to 1.5 times the molar quantity of the carboxylic acid (2).

In the above reaction formula-1, the carboxylic acid (2) is a known compound, and the amine (3) is either a known compound or a novel compound. The amine (3) can be easily obtained by a method expressed by the following reaction process formula-2 or reaction process formula-3.

Reaction process formula-2

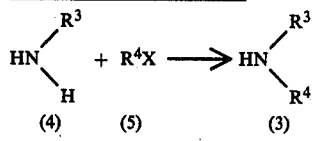

Reaction process formula-3

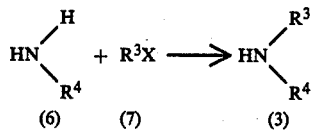

wherein $R^3$ and $R^4$ are the same as defined previously, and X is a halogen atom.

According to the reaction process formula-2, the amine represented by the general formula (3) can be easily obtained by reacting a known amine of the general formula (4) with a known halogen compound of the general formula (5) in the presence of a basic compound. According to the reaction process formula-3, the amine represented by the general formula (3) can be produced by reacting a known amine of the general formula (6) with a known halogen compound of the general formula (7) in the presence of a basic compound. These reactions are accomplished by using a basic compound as dehydrohalogenating agent. The basic compound used in said reaction may be selected from a wide variety of known basic compounds including inorganic bases such as sodium hydroxide, potassium hydroxide, sodium carbonate, potassium carbonate, sodium hydrogencarbonate, potassium hydrogencarbonate, silver carbonate, or the like; alkali metals such as sodium, potassium, or the like; alcoholates such as sodium methylate, sodium ethylate, or the like; and organic bases such as triethylamine, pyridine, N,N-dimethylaniline, or the like. The above reaction can be carried out in the absence or presence of a solvent. The solvent used in this reaction may be of any known inert type which gives no adverse effect to the reaction. Among the examples of such solvent are alcohols such as methanol, ethanol, propanol, butanol, ethylene glycol, or the like; ethers such as diethyl ether, tetrahydrofuran, dioxane, monoglyme, diglyme, or the like; ketones such as acetone, methyl ethyl ketone, or the like; aromatic hydrocarbons such as benzene, toluene, xylene, or the like; esters such as methyl acetate, ethyl acetate, or the like; and aprotic polar solvents such as N,N-dimethylformamide, dimethylsulfoxide, hexamethylphosphoric acid triamide. It is advantageous to carry out the said reactions in the presence of a metallic iodide such as sodium iodide or potassium iodide. The ratio of amount of the halogenide compound (5) or (7) to the amine (4) or (6) in the above method is not subject to any specific restriction and may be suitably selected from a wide range, and in the absence of a solvent the latter can be used in a large excess amount to the former, but usually it is desirable that the latter is used in equimolar to 5 times the molar quantity, preferably equimolar to double the molar quantity of the former. The reaction temperature is also not subject to any particular definiton, but the reaction is usually carried out at room temperature to 200° C., preferably at 50° to 160° C. The reaction time is usually 1 to 30 hours, preferably 5 to 15 hours.

The compound (1) of the present invention can also be prepared by a method according to reaction process formula-4.

Reaction process formula-4

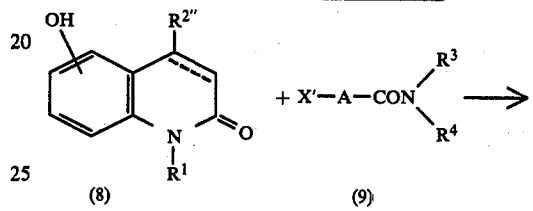

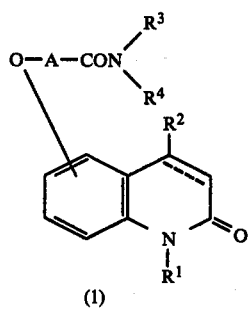

wherein $R^1$, $R^2$, $R^3$, $R^4$, A and the carbon-carbon bond between 3- and 4-positions in the carbostyril skeleton and the substituted position of the group of the formula

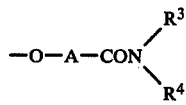

are the same as defined previously; X' is a halogen atom, an alkanesulfonyloxy group, an arylsulfonyloxy group or an aralkylsulfonyloxy group; $R^{2''}$ is a hydrogen atom, a lower alkyl group or a hydroxy group; and the substituted position of the hydroxy group is any one of 5-, 6-, 7- or 8-position in the carbostyril skeleton, when the hydroxy group is substituted at 5-, 6-, 7- or 8-position in the carbostyril skeleton, then $R^{2''}$ is a hydrogen atom or a lower alkyl group; alternatively, when $R^{2''}$ is a hydroxy group, then the 5-, 6-, 7- and 8-position in the carbostyril skeleton are hydrogen atoms, and are not substituted with the hydroxy groups.

According to reaction process formula-4, the objective compound (1) of the present invention can be obtained by reacting a hydroxycarbostyril derivative represented by the general formula (8) with an alkaneamide derivative represented by the general formula (9) in the presence of a basic compound.

In carrying out the reaction process formula-4, the reaction conditions used in the reaction process formula-2 or -3 can be applied. As to examples of the X' shown in the general formula (9), one may cite a substituted or unsubstituted arylsulfonyloxy group such as phenylsulfonyloxy, p-toluenesulfonyloxy, o-toluenesulfonyloxy, 4-nitrophenylsulfonyloxy, 4-methoxyphenylsulfonyloxy, 3-chlorophenylsulfonyloxy, α- or β-naphthylsulfonyloxy group or the like; a substituted or unsubstituted aralkyl sulfonyloxy group such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy, β-naphthylmethylsulfonyloxy group or the like.

The hydroxycarbostyril compound represented by the general formula (8) as used for a starting material is a known compound, and the alkaneamide compound represented by the general formula (9) as used for another starting material is a known or novel compound. The alkaneamide compound of represented by the general formula (9) can be easily prepared by a method expressed in the following reaction process formula-5.

Reaction process formula-5

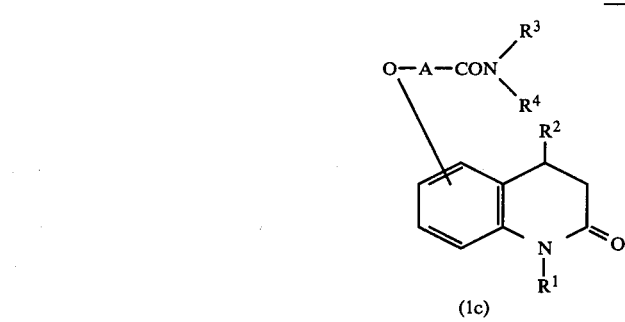

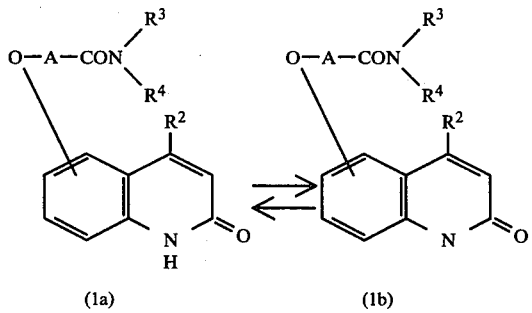

wherein $R^2$, $R^3$, $R^4$, A and the substituted position of the group of the formula

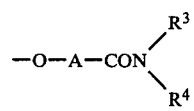

are the same as defined previously.

Next, as is shown in the following reaction process formula-7 among the compounds of the present invention, a compound (1c) of which the carbon-carbon bond between 3- and 4-positions in the carbostyril skeleton is a single bond and a comound (1a) can be converted into mutually by reduction and dehydrogenation.

Reaction process formula-7

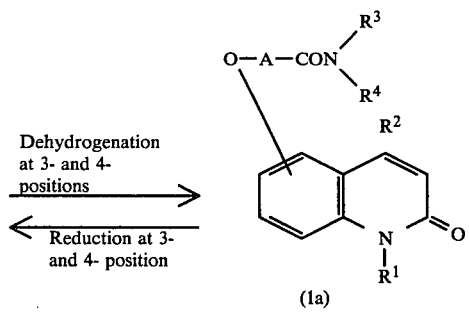

wherein $R^3$, $R^4$ A and X' are the same as defined previously. Thus the alkaneamide compound represented by the general formula (9) can be obtained by reacting a compound represented by the general formula (10) with an amine represented by the general formula (3) according to an ordinary mode of amide bond forming reaction. In carrying out said amide bond forming reaction, the reaction conditions used in the reaction process formula-1 can also be applied.

Among the objective compounds of the general formula (1) of the present invention, those having double bond of carbon-carbon linkage at the 3- and 4-positions in the carbostyril skeleton capable of existing in both the lactam-lactim forms [(1a) and (1b)] as shown in the reaction process formula-6 as follows.

Reaction process formula-6 wherein $R^1$, $R^2$, $R^3$, $R^4$, A and the substituted position of the group of the formula

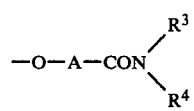

are the same as defined previously.

Further, the objective compound (1) of the present invention can also be prepared by a method according to reaction process formula-8 as follows:

Reaction process formula-8

-continued

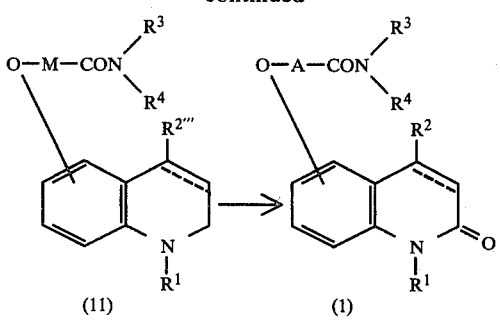

wherein $R^1$, $R^2$, $R^3$, $R^4$, A and the carbon-carbon bond between 3- and 4-positions in the carbostyril skeleton and the substituted position of the group of the formula

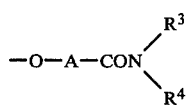

are the same as defined previously; $R^{2'''}$ is a hydrogen atom, a lower alkyl group or a group of the formula

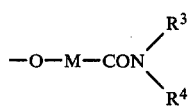

(wherein $R^3$ and $R^4$ are the same as defined above; M is an unsaturated lower alkylene group); and the substituted position of the group of the formula

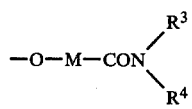

is any one of 5, 6-, 7- or 8-position in the carbostyril skeleton; when the group of the formula

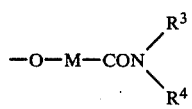

is substituted at 5-, 6-, 7- or 8-position in the carbostyril skeleton, then $R^{2'''}$ is a hydrogen atom or a lower alkyl group; alternatively, when $R^{2'''}$ is a group of the formula

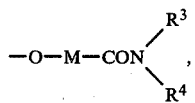

then the 5-, 6-, 7- and 8-positions in the carbostyril skeleton are hydrogen atoms, and are not substituted with groups of the formula

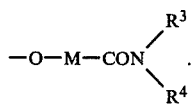

Thus according to a method of the reaction process formula-8, the objective compound (1) of the present invention can be prepared by reducing a carbostyril derivative represented by the general formula (11).

In carrying out the reduction of the compound (11), the conditions used in an ordinary mode of reduction of unsaturated alkane compound to obtain the corresponding saturated alkane compound can be applied. Among said conditions, those of used in catalytic reductions can specifically be employed advantageously. The catalytic reduction may be carried out by using a catalyst according to an usual way by hydrogenating the compound (11) in a suitable solvent. As examples of the catalysts, one may cite catalysts ordinary used in nuclear hydrogenation reaction, for example, platinum catalysts such as platinum black, platinum oxide, colloidal platinum or the like; palladium catalysts such as palladium black, palladium carbon, colloidal palladium or the like; rhodium catalysts such as asbestos-filled rhodium, rhodium alumina or the like; ruthenium catalysts; nickel catalysts such as Raney nickel, nickel oxide or the like; cobalt catalyst. As examples of the solvents used in said reduction, one may cite lower alcohols such as methanol, ethanol, isopropanol or the like; water; acetic acid; esters of acetates, ethylene glycol; ethers such as tetrahydrofuran, dioxane or the like; cycloalkanes such as cyclohexane, cyclopentane or the like. Said reduction can be carried out in a hydrogen gas stream under pressure or an atmospheric pressure, preferably it is carried out under atmospheric pressure. The reduction can usually be carried out at from a room temperature to about 100° C., preferably at from a room temperature to 50° C., and generally the reduction is completed within about 1 to 10 hours.

Under the above-mentioned conditions of the reduction according to reaction process formula-8, there are occurred that an unsaturated alkyl group among the groups defined in $R^1$, some of the groups defined in $R^3$ and $R^4$ and the double bond of the carbon-carbon linkage between 3- and 4-positions in the carbostyril skeleton may be reduced in certain extent.

Compounds of the general formula (11) used as the starting materials in the reaction process formula-8 are novel and can be prepared by a method according to reaction process formula-9 as follows:

Reaction process formula-9

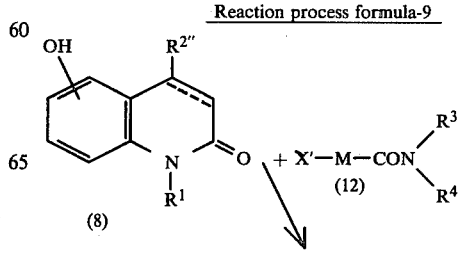

-continued
Reaction process formula-9

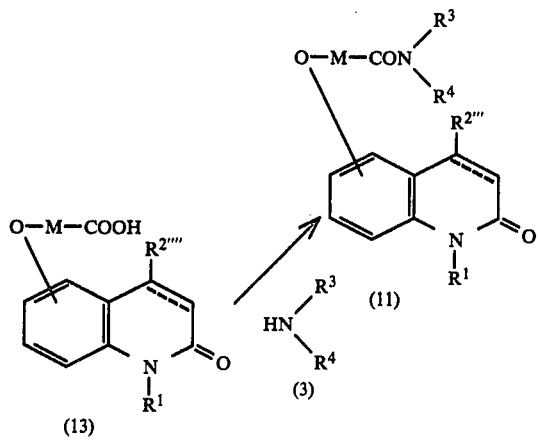

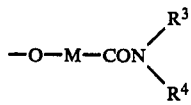

(13)

wherein $R^1$, $R^{2''}$, $R^{2'''}$, $R^3$, $R^4$, M, X' and the carbon-carbon bond between 3- and 4-positions in the carbostyril skeleton are the same as defined previously; the substituted position of the group of the formula $$-O-M-CON\begin{matrix}R^3\\R^4\end{matrix}$$

is any one of 5-, 6-, 7- or 8-position in the carbostyril skeleton; $R^{2''''}$ is a hydrogen atom, a lower alkyl group or a group of the formula —O—M—COOH (wherein M is the same as defined above); and the substituted position of the formula —O—M—COOH is any one of 5-, 6-, 7- or 8-position in the carbostyril skeleton; when the group of the formula —O—M—COOH is substituted at 5-, 6-, 7- or 8-position in carbostyril skeleton, then $R^{2''''}$ is a hydrogen atom or a lower alkyl group; alternatively, when $R^{2''''}$ is a group of the formula —O—M—COOH, then 5-, 6-, 7- and 8-positions in the carbostyril skeleton are hydrogen atoms, and are not substituted with groups of the formula —O—M—COOH.

The reaction of a hydroxy carbostyril of the formula (8) and a compound of the general formula (12) in the reaction process formula-9 can be carried out by a method similar to that described in reaction process formula-4, and the reaction of a compound of the general formula (13) and an amine of the formula (3) in the reaction process formula-9 can be carried out by a method similar to the reaction in the reaction process formula-1, respectively. Here, the compound of the general formula (12) can easily be prepared by reacting a compound of the general formula (14)

X'—M—COOH         (14)

wherein X' and M are the same as defined previously, with an amine of the general formula (3) according to a method similar to that in the reaction process formula-5.

Among the objective compounds of the general formula (1) in the present invention, an ester derivative of the general formula (1e) can be prepared from a hydroxy derivative of the general formula (1d) by a method according to reaction process formula-10 as follows.

Reaction process formula-10

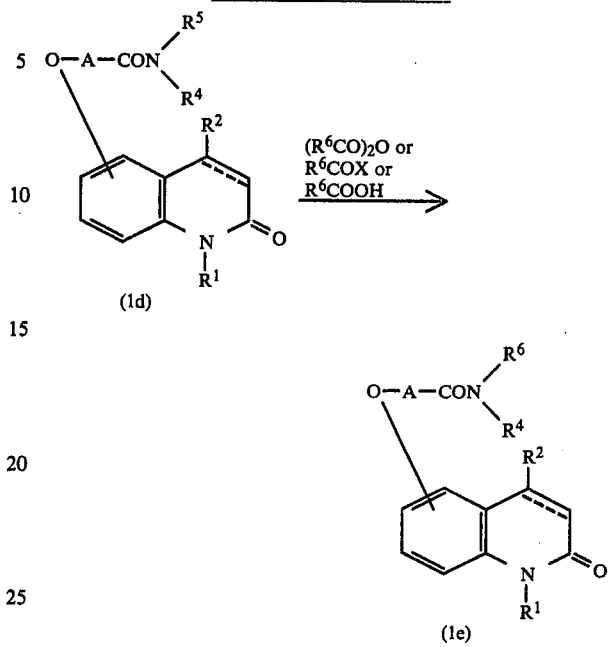

wherein $R^1$, $R^2$, $R^4$, A, and the carbon-carbon bond between 3- and 4-positions in the carbostyril skeleton are the same as defined above; $R^5$ is a lower alkyl group having a hydroxyl group as the substituted group; $R^6$ is a lower alkanoyloxy-lower alkyl group or a benzoyloxy-lower alkyl group; X is a halogen atom; the substituted position of the groups of the formulas

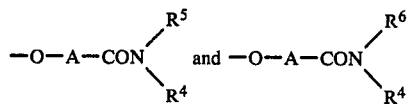

are respectively the same as defined in that of the group of the formula

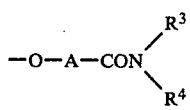

previously.

Thus, according to the reaction process formula-10, a reaction for preparing the ester derivative (1e) from the hydroxy derivative (1d) can be carried out by an ordinary mode of ester formation reaction. The ester derivative (1e) can be prepared by reacting a hydroxy derivative (1d) with a carboxylic acid of the formula $R^6COOH$ or with a compound of which carboxyl group being activated, for example, a carboxylic acid anhydride $(R^6CO)_2O$, carboxylic acid halogenide $R^6COX$ (wherein X is a halogen atom).

In using carboxylic acid anhydride $(R^6CO)_2O$ or carboxylic acid halogenide $R^6COX$ as an acylating agent, an usual Schötten-Baumann reaction condition can easily be applied to this reaction condition. The reaction is carried out in the absence or presence of a solvent. As to the solvent used in this reaction, solvents ordinary used in Schötten-Baumann reaction can be used. As examples thereof, one may cite halogenated hydrocarbons such as methylene chloride, chloroform or the like; ketones such as acetone, methyl ethyl ketone or the like; ethers such as diethyl ether, tetrahydrofuran or the like; fatty acids such as acetic acid, propionic acid or the like; aromatic hydrocarbons such as benzene, toluene or the like; aprotic polar solvent such as dimethylformamide, hexamethylphosphoric triamide, acetonitrile or the like. In carrying out this reaction, an inorganic basic compound such as sodium acetate, potassium carbonate, sodium hydrogencarbonate; an organic basic compound such as triethylamine, pyridine, N-methylmorphorine, 4-dimethylaminopyridine, diazabicycloundecene-7 (DBU) or the like; and a protonic acid such as p-toluenesulfonic acid, sulfuric acid or the like; a Lewis acid such as aluminium chloride, boron trifluoride, zinc chloride or the like can also be presented.

In this reaction, the ratio of the amount of the hydroxy compound (1d) to the amount of the carboxylic acid anhydride or the carboxylic acid halogenide may be in the range of 1 to 5 times the molar quantity of the latter to the former, preferably, equimolar to double the molar quantity of the latter. The reaction temperature is not subject to any particular definition, but the reaction is usually carried out at a temperature within a range of $-10°$ to $100°$ C., preferably at $0°$ to $50°$ C. The length of the reaction time is depend on the type of the starting material and, the reaction condition, and usually the reaction is completed in a period within about 10 minutes to 10 hours.

In case of using carboxylic acid as the acylating agent, a reaction condition used in an ordinary dehydration reaction of a hydroxy compound with a carboxylic acid can also be widely used.

This reaction is usually carried out in the presence of a catalyst. As to the catalyst, those used in usual esterification can be used. As typical examples thereof, one may cite inorganic acids such as gaseous hydrogen chloride, concentrated sulfuric acid, phosphoric acid, a polyphosphoric acid, boron trifluoride, perchloric acid or the like; organic acids such as trifluoracetic acid, trifluoromethanesulfonic acid, naphthalenesulfonic acid, p-toluenesulfonic acid, benzenesulfonic acid, ethanesulfonic acid or the like; thionyl chlorid; acetonedimethylacetal or the like. Further, an acidic ion-exchange resin can also be used as a catalyst in this reaction. The amount of these catalysts used in this reaction may be of an usual amount and is not subject to any particular restriction. This reaction can be carried out in the absence or presence of a solvent. As to the solvent to be used may be any solvent employed in an usual esterification reaction can advantageously be used. As examples thereof, one may cite aromatic hydrocarbons such as benzene, toluene, xylene or the like; halogenated hydrocarbons such as dichloromethane, dichloroethane, chloroform, carbon tetrachloride or the like; ethers such as diethyl ether, tetrahydrofuran, dioxane, ethylene glycol monomethyl ether or the like. The ratio of the amount of the hydroxy derivative (1d) to the amount of the carboxylic acid may be selected from a wide range, and usually the latter is used in equimolar to 5 times the molar quantity of the former. Additionally, in the present invention, the yield of the desired product can be increased by removing the water formed in the reaction by using a drying agent such as anhydrous calcium chloride, anhydrous cupper sulfate, anhydrous calcium sulfate, phosphorous pentaoxide or the like.

The reaction temperature in this reaction is not subject to any particular definition, but the reaction is usually carried out at a temperature within the range of $-20°$ to $200°$ C., preferably at $0°$ to $150°$ C. The length of the reaction time is depend on the type of the starting material and the reaction condition, and usually the reaction is completed in a period within about 10 minutes to 20 hours.

Among the compounds represented by the general formula (1), those compounds which have an acidic group can easily form salts with the pharmaceutically acceptable basic compounds include basic compounds, for example metallic hydroxides such as sodium hydroxide, potassium hydroxide, calcium hydroxide, aluminum hydroxide, etc.; alkali metal alcoholates such as sodium methlate, potassium ethylate, etc. represented by the general formula (1), those having a basic group can easily form salts with the usual pharmaceutically acceptable acids which include inorganic acids such as sulfuric acid, nitric acid, hydrochloric acid, hydrobromic acid, etc.

The thus obtained compounds of the present invention can be easily isolated and refined by the usual separation means such as precipitation, extraction, recrystallization, column chromatography and preparative thin layer chromatography.

The compounds of the present invention can be administered, either in the form as they are or together with a conventional pharmaceutically acceptable carrier, to animals as well as to human being. No particular restriction is placed on the administration unit forms and the compounds can be used in any desired unit form. Suitable administration unit forms include such oral administration forms as tablets, capsules, granules, and solutions etc.; and parenteral administration forms such as injections. The dosage of the active ingredient to be administered is not subject to any particular definition and admits of selection from a wide range, but in order to obtain a desired pharmacological effect, it is recommended to select said dosage from the range of 0.06 to 10 mg per kg body weight per day. It is also suggested to contain 1 to 500 mg of the active ingredient in each unit dose of the administration forms.

The compounds of the present invention can be formed into the desired peroral preparations such as tablets, capsules, solutions, etc., according to a common method. For preparation of tablets, a compound of the present invention is mixed with a pharmaceutically acceptable excipient such as gelatin, starch, lactose, magnesium stearate, talc, gum arabic or the like and shaped into tablets. Capsules can be obtained by mixing a compound of this invention with an inert pharmaceutically acceptable filler or diluent and filling the mixture into rigid gelatin capsules or soft capsules. Sirups or elixirs may be prepared by mixing a compound of the present invention with a sweetening such as sucrose, antiseptic such as methyl- and propyl-parabens, colorant, seasoning and/or other suitable additives.

Parenteral preparations can be also obtained according to a common method. In this case, the compound of the present invention is dissolved in a sterilized liquid vehicle. Preferred vehicle is water or saline water. Liquid preparations having desired transparency, stability and parenteral use adaptability can be obtained by dissolving approximately 1 to 500 mg of the active ingredient in a solution of polyethylene glycol, having molecular weight of 200–5000, which is soluble in both water and organic solvents. Desirably, such liquid preparations contain a lubricant such as sodium carboxymethyl cellulose, methyl cellulose, polyvinyl pyrrolidone, polyvinyl alcohol or the like. Said liquid preparations may also contain a bactericide and fungicide such as benzyl alcohol, phenol or thimerosal and, if necessary, an isotonic agent such as sucrose or sodium chloride, a local anesthetic, stabilizer, buffer, etc. For additional ensurance of stability, the parenteral compositions may be freezed after filling and dehydrated by the known freeze-drying techniques. The freeze-dried powder can be returned to the normal use form just before use.

Preparation of tablets 1,000 Tablets for peroral use, each containing 5 mg of 6-{4-[N-(2-hydroxyethyl)-N-cyclohexylaminocarbonyl]butoxy}-3,4-dihydrocarbostyril, are prepared from the following prescription.

| Ingredient | Amount (g) |
| --- | --- |
| 6-{4-[N—(2-Hydroxyethyl)-N—cyclohexylaminocarbonyl]butoxy}-3,4-dihydrocarbostyril | 5 |
| Lactose (J.P. = Japanese Pharmacopoeia) | 50 |
| Corn starch (J.P.) | 25 |
| Crystalline cellulose (J.P.) | 25 |
| Methyl cellulose (J.P.) | 1.5 |
| Magnesium stearate (J.P.) | 1 |

The above specified 6-{4-[N-(2-hydroxyethyl)-N-cyclohexylaminocarbonyl]butoxy}-3,4-dihydrocarbostyril, lactose, corn starch and crystalline cellulose are mixed well, and the mixture is added with a 5% aqueous solution of methyl cellulose and then granulated. The obtained granules are passed through a 200 mesh sieve and then dried carefully. The dried granules passed through the 200 mesh sieve are admixed with magnesium stearate, and then compressed into tablets.

Preparation of tablets 1,000 Tablets for peroral use, each containing 5 mg of 6-{3-[N-(2-hydroxyethyl)-N-cyclohexylaminocarbonyl]propoxy}carbostyril, are prepared in the similar way from the following prescription.

| Ingredient | Amount (g) |
| --- | --- |
| 6-{3-[N—(2-hydroxyethyl)-N—cyclohexylaminocarbonyl]propoxy}carbostyril | 5 |
| Lactose (J.P.) | 50 |
| Corn starch (J.P.) | 25 |
| Crystalline cellulose (J.P.) | 25 |
| Methyl cellulose (J.P.) | 1.5 |
| Magnesium stearate (J.P.) | 1 |

Preparation of capsules 1,000 Pieces of two-piece rigid gelation capsules for peroral use, each containing 10 mg of 6-{4-[N-(2-hydroxyethyl)-N-(2-tetrahydropyranylmethyl)aminocarbonyl]butoxy}-3,4-dihydrocarbostyril, are prepared from the following prescription.

| Ingredient | Amount (g) |
| --- | --- |
| 6-{4-[N—(2-Hydroxyethyl)-N—(2-tetrahydropyranylmethyl)aminocarbonyl]butoxy}-3,4-dihydrocarbostyril | 10 |
| Lactose (J.P.) | 80 |
| Starch (J.P.) | 30 |
| Talc (J.P.) | 5 |

-continued

| Ingredient | Amount (g) |
| --- | --- |
| Magnesium stearate (J.P.) | 1 |

The above components are finely ground, then stirred and mixed sufficiently to form a uniform mixture and then filled into the gelatin capsules with a size convenient for peroral administration.

Preparation of capsules 1,000 Pieces of two-piece rigid gelatin capsules for peroral use, each containing 10 mg of 6-[3-(4-phenyl-1-piperazinylcarbonyl)propoxy]carbostyril, are prepared in the similar way from the following prescription.

| Ingredient | Amount (g) |
| --- | --- |
| 6-[3-(4-phenyl-1-piperazinylcarbonyl)propoxy]carbostyril | 10 |
| Lactose (J.P.) | 80 |
| Starch (J.P.) | 30 |
| Talc (J.P.) | 5 |
| Magnesium stearate (J.P.) | 1 |

Preparation of capsules 1,000 Pieces of two-piece rigid gelatin capsules for peroral use, each containing 10 mg of 6-{3-[N-methyl-N-(3-pyridylmethyl)aminocarbonyl]propoxy}carbostyril, are prepared in the similar way from the following prescription.

| Ingredient | Amount (g) |
| --- | --- |
| 6-{3-[N—Methyl-N—(3-pyridylmethyl)aminocarbonyl]propoxy}carbostyril | 10 |
| Lactose (J.P.) | 80 |
| Starch (J.P.) | 30 |
| Talc (J.P.) | 5 |
| Magnesium stearate (J.P.) | 1 |

Preparation of capsules 1,000 Pieces of two-piece rigid gelatin capsules for peroral use, each containing 10 mg of 6-{3-[N-ethyl-N-(2-pyridyl)aminocarbonyl]propoxy}carbostyril, are prepared in the similar way from the following prescription.

| Ingredient | Amount (g) |
| --- | --- |
| 6-{3-[N—Ethyl-N—(2-pyridyl)aminocarbonyl]propoxy}carbostyril | 10 |
| Lactose (J.P.) | 80 |
| Starch (J.P.) | 30 |
| Talc (J.P.) | 5 |
| Magnesium stearate (J.P.) | 1 |

Preparation of injection

A sterile aqueous solution suitable for parenteral use is prepared from the following prescription.

| Ingredient | Amount (g) |
| --- | --- |
| 6-{3-[N—(2-Hydroxyethyl)-N—cyclohexylaminocarbonyl]propoxy}carbostyril | 1 |
| Polyethylene glycol (J.P.) [molecular weight: 4,000] | 0.3 |

-continued

| Ingredient | Amount (g) |
| --- | --- |
| Sodium chloride (J.P.) | 0.9 |
| Polyoxyethylene sorbitan monooleate (J.P.) | 0.4 |
| Sodium metabisulfite | 0.1 |
| Methyl p-hydroxybenzoate (J.P.) | 0.18 |
| Propyl p-hydroxybenzoate (J.P.) | 0.02 |
| Distilled water for injection | 100 ml |

A mixture of the above-prescribed methyl p-hydroxybenzoate, propyl p-hydroxybenzoate, sodium metabisulfite and sodium chloride, while stirred, is dissolved in about half the quantity of distilled water at 80° C. The obtained solution is cooled to 40° C., and then 6-{3-[N-(2-hydroxyethyl)-N-cyclohexylaminocarbonyl]propoxy}carbostyril, polyethylene glycol and polyoxyethylene sorbitan monooleate are dissolved in that order in said solution. This solution is further added with distilled water for injection to the final regulated volume and then sterilized by sterile filtration with a suitable filter paper.

The results of the pharmacological tests on the compounds of this invention are shown below.

Pharmacological Test 1

The platelet aggregation inhibitory effect is measured by using AG-II aggregometer (manufactured by Bryston Manufacturing Co.). The blood sample used for the test is a 1/9 (by volume) mixture of sodium citrate and whole blood collected from rabbit. Said sample is subjected to 10-minute centrifugal separation at 1,000 r.p.m. to obtain a platelet rich plasma (PRP). The thus obtained PRP is separated, and the remaining blood sample is further subjected to 15-minute centrifugal separation at 3,000 r.p.m. to obtain a platelet poor plasma (PPP).

The number of platelets in the PRP is counted by the Brecher-Clonkite Method, and the PRP is diluted with the PPP to prepare a PRP sample with platelet concentration of 300,000/mm$^3$ for the adenosine diphosphate (ADP)-induced aggregation test. There is also prepared a PRP sample with platelet concentration of 450,000/mm$^3$ for the collagen-induced aggregation test.

0.6 Milliliter of said PRP sample is added into 0.01 ml of a solution of a test compound of a predetermined concentration and the mixture is placed in a 37° C. thermostat for one minute. Then 0.07 ml of an ADP or collagen solution is added to the mixture. Transmittance of this mixture is determined and the change of transmittance is recorded by using the aggregometer at stirrer speed of 1,100 r.p.m. In this test, Auren Beronal buffer (pH 7.35) is used for the preparation of the ADP or collagen solution. The ADP solution is adjusted to a concentration of $7.5 \times 10^{-5}$ M, and the collagen solution is prepared by triturating 100 mg of collagen with 5 ml of said buffer and the supernatant is used as collagen inducer. Acetylsalicylic acid is used as control for the ADP-induced aggregation test and the collagen-induced aggregation test, respectively. The platelet aggregation inhibitory effect is measured in terms of percent inhibition with respect to the aggregation rate of the controls. The aggregation rate is calculated from the following formula:

Aggregation rate = [(c−a)/(b−a)] × 100 wherein a: transmittance of PRP
b: transmittance of PRP containing a test compound and an aggregation inducer
c: transmittance of PPP.

The inhibitory effect of the tested compounds on collagen-induced aggregation in rabbit platelets is shown in Table 1, and such effect on ADP-induced aggregation is shown in Table 2. The compounds tested are as follows:

| No. | Tested Compounds |
| --- | --- |
| | Compounds of the present invention (Nos. 1–23) |
| 1. | 6-{3-[N—(2-Hydroxyethyl)-N—cyclohexylaminocarbonyl]propoxy}carbostyril |
| 2. | 6-{3-[N—Ethyl-N—(3-pyridylmethyl)aminocarbonylamino]propoxy}carbostyril |
| 3. | 6-{3-[N—Ethyl-N—(2-pyridyl)aminocarbonyl]propoxy}carbostyril |
| 4. | 6-{3-[N—Methyl-N—(2-furylmethyl)aminocarbonyl]propoxy}carbostyril |
| 5. | 6-{3-[N—Methyl-N—(2-thienylmethyl)aminocarbonyl]propoxy}carbostyril |
| 6. | 6-{3-[N—Methyl-N—(2-tetrahydropyranylmethyl)aminocarbonyl]propoxy}carbostyril |
| 7. | 6-{4-[N—(2-Hydroxybutyl)-N—cyclohexylmethylaminocarbonyl]butoxy}-3,4-dihydrocarbostyril |
| 8. | 6-{4-[N—(4-Hydroxybutyl)-N—cyclohexylmethylaminocarbonyl]butoxy}-3,4-dihydrocarbostyril |
| 9. | 6-{4-[N—(2-Hydroxybutyl)-N—cyclooctylaminocarbonyl]butoxy}carbostyril |
| 10. | 6-{3-[N—(2-Benzoyloxyethyl)-N—cyclohexylaminocarbonyl]propoxy}carbostyril |
| 11. | 6-{4-[N—(2-Hydroxyethyl)-N—phenylaminocarbonyl]butoxy}-3,4-dihydrocarbostyril |
| 12. | 6-{4-[N—Butyl-N—(2-tetrahydropyranylmethyl)aminocarbonyl]butoxy}-3,4-dihydrocarbostyril |
| 13. | 6-{4-[N—(2-Hydroxyethyl)-N—(2-tetrahydropyranylmethyl)aminocarbonyl]butoxy}-3,4-dihydrocarbostyril |
| 14. | 6-[3-(4-Phenyl-1-piperazinylcarbonyl)propoxy]carbostyril |
| 15. | 6-[3-(4-Benzyl-1-piperazinylcarbonyl)propoxy]-3,4-dihydrocarbostyril |
| 16. | 6-[3-(4-Phenyl-1-piperidylcarbonyl)propoxy]carbostyril |
| 17. | 6-[3-(4-Phenyl-1-piperazinylcarbonyl)propoxy]-3,4-dihydrocarbostyril |
| 18. | 6-[3-(4-Cyclohexyl-1-piperazinylcarbonyl)propoxy]-3,4-dihydrocarbostyril |
| 19. | 6-{3-[N—(2-Hydroxyethyl)-N—(3-hydroxycyclohexyl)aminocarbonyl]propoxy} carbostyril |
| 20. | 6-{4-[N—(2-Hydroxyethyl)-N—(β-3,4-dimethoxyphenethyl)aminocarbonyl]butoxy}carbostyril |
| 21. | 6-{4-[N—(3-Acetyloxypropyl)-N—(2-tetrahydropyranylmethyl)aminocarbonyl]butoxy}-3,4-dihydrocarbostyril |
| 22. | 6-{4-[N—(2-Hydroxyethyl)-N—benzylaminocarbonyl]butoxy}-3,4-dihydrocarbostyril |
| 23. | 6-{4-[N—(2-Methoxyethyl)-N—cyclohexylaminocarbonyl]butoxy}carbostyril |
| | Known compounds (comparative compounds) Nos. 24–69 |
| 24. | 6-{3-[N—Methyl-N—(2-methylcyclohexyl)aminocarbonyl]propoxy}carbostyril |
| 25. | 6-{3-[N—Methyl-N—(4-hydroxycyclohexyl)aminocarbonyl]propoxy}carbostyril |
| 26. | 6-{3-[N—Methyl-N—(4-acetyloxycyclohexyl)aminocarbonyl]propoxy}carbostyril |
| 27. | 6-{3-[N—Methyl-N—(2-3',4'-dimethoxyphenylethyl)aminocarbonyl]propoxy}carbostyril |
| 28. | 6-[3-(N—Cyclohexyl-N—benzylaminocarbonyl)propoxy]carbostyril |
| 29. | 5-Chloro-6-[3-(N—methyl-N—cyclohexylaminocarbonyl)propoxy]carbostyril |
| 30. | 6-{3-[N—Cyclohexyl-N—(2-chlorocyclohexyl)aminocarbonyl]propoxy}-3,4-dihydrocarbostyril |
| 31. | 6-[2-Hydroxy-3-(N—methyl-N—cyclohexylaminocarbonyl)propoxy]carbostyril |
| 32. | 6-[3-(N—Methyl-N—cyclohexylaminocarbonyl)-2-methylpropoxy]carbostyril |
| 33. | 8-Hydroxy-5-[3-(N—Methyl-N—cyclohexylamino- |

-continued

| No. | Tested Compounds |
|---|---|
| | carbonyl)propoxy]-3,4-dihydrocarbostyril |
| 34. | 6-{3-[N—Benzyl-N—(2-3',4'-dimethyoxyphenylethyl)aminocarbonyl]]propoxy}-3,4-dihydrocarbostyril |
| 35. | 6,8-Dichloro-5-[3-(N—ethylanilinocarbonyl)-propoxy]-3,4-dihydrocarbostyril |
| 36. | 6-[3-(N—Cyclohexylaminocarbonyl)propoxy]-carbostyril |
| 37. | 6-[3-(N—Allyl-N—cyclohexylaminocarbonyl)-propoxy]-3,4-dihydrocarbostyril |
| 38. | 6-[3-(N—Methyl-N— cyclohexylaminocarbonyl)-propoxy]-3,4-dihydrocarbostyril |
| 39. | 6-[3-(N—Methyl-N—cyclohexylaminocarbonyl)-propoxy]carbostyril |
| 40. | 6-[3-(N—Cyclohexylanilinocarbonyl)propoxy]-carbostyril |
| 41. | 6-[3-(N,N—Dicyclohexylaminocarbonyl)propoxy]-3,4-dihydrocarbostyril |
| 42. | 6-[3-(Anilinocarbonyl)propoxy]-3,4-dihydro-carbostyril |
| 43. | 6-[3-(N—Ethylanilinocarbonyl)propoxy]-carbostyril |
| 44. | 6-[3-(o,o-Dichloroanilinocarbonyl)propoxy]-3,4-dihydrocarbostyril |
| 45. | 6-[4-(N—Butyl-N—cyclohexylaminocarbonyl)-butoxy]-3,4-dihydrocarbostyril |
| 46. | 5-[3-(N—Methyl-N—cyclohexylaminocarbonyl)-propoxy]-3,4-dihydrocarbostyril |
| 47. | 6-[3-(N,N—Diphenylaminocarbonyl)propoxy]-3,4-dihydrocarbostyril |
| 48. | 6-(1-Ethoxycarbonylethoxy)-3,4-dihydro-carbostyril |
| 49. | 6-(1-Ethoxycarbonylethoxy)carbostyril |
| 50. | 1-Methyl-6-(1-ethoxycarbonylethoxy)-3,4-dihydrocarbostyril |
| 51. | 7-(1-Ethoxycarbonylethoxy)-3,4-dihydrocarbostyril |
| 52. | 6-(3-Ethoxycarbonylpropoxy)-3,4-dihydrocarbostyril |
| 53. | 6-(1-Amyloxycarbonylethoxy)-3,4-dihydrocarbostyril |
| 54. | 6-(1-Isopropoxycarbonylethoxy)carbostyril |
| 55. | 5-(3-Ethoxycarbonylpropoxy)-3,4-dihydro-carbostyril |
| 56. | 6-(3-Amyloxycarbonylpropoxy)-3,4-dihydro-carbostyril |
| 57. | 6-(3-Ethoxycarbonylpropoxy)carbostyril |
| 58. | 6-(6-Ethoxycarbonylhexyloxy)-3,4-dihydro-carbostyril |
| 59. | 6-(6-Carboxyhexyloxy)-3,4-dihydrocarbostyril |
| 60. | 8-(1-Ethoxycarbonylethoxy)-3,4-dihydro-carbostyril |
| 61. | 6-(1-Methyl-1-carboxyethoxy)-3,4-dihydro-carbostyril |
| 62. | 6-(3-Carboxypropoxy)carbostyril |
| 63. | 6-(3-Cyclohexyloxycarbonylpropoxy)-3,4-dihydrocarbostyril |
| 64. | 6-(N—Isopropylaminocarbonylethoxy)-3,4-dihydrocarbostyril |
| 65. | 6-(Morpholinocarbonylmethoxy)-3,4-dihydro-carbostyril |
| 66. | 5-(N,N—Dimethylaminocarbonylmethoxy)-3,4-dihydrocarbostyril |
| 67. | 1-Ethyl-5-[3-(N—benzylaminocarbonyl)propoxy] -3,4-dihydrocarbostyril |
| 68. | 6-[3-(N—Propylaminocarbonyl)-2-methylpropoxy]-3,4-dihydrocarbostyril |
| 69. | Aspirin |

TABLE 1

Inhibition effect of carbostyril derivatives on collagen-induced aggregation in rabbit platelet

| Test compound No. | Concentration of the test compound solution | | | |
|---|---|---|---|---|
| | $10^{-4}$ mole | $10^{-5}$ mole | $10^{-6}$ mole | $10^{-7}$ mole |
| Compounds of the present invention | | | | |
| 1 | 100% | 100% | 100% | 60.1% |
| 2 | 100 | 82 | 7.2 | — |
| 3 | 100 | 100 | 14 | — |
| 4 | 92.5 | 35.8 | 4.0 | — |
| 5 | 85.7 | 30.7 | — | — |
| 6 | 100 | 48.1 | 3.8 | — |
| 7 | 100 | 100 | 13.3 | — |
| 8 | 100 | 100 | 10.2 | — |
| 9 | 100 | 100 | 100 | 43.2 |
| 10 | 100 | 100 | 100 | 56.7 |
| 11 | 100 | 100 | 33.9 | — |
| 12 | 100 | 100 | 10.3 | — |
| 13 | 100 | 81.7 | 5.2 | — |
| 14 | 100 | 100 | 31.0 | — |
| 15 | 100 | 98.8 | 24.6 | — |
| 16 | 100 | 40.8 | 7.7 | — |
| 17 | 100 | 37.8 | 3.4 | — |
| 18 | 100 | 45.6 | 15.2 | — |
| 19 | 100 | 95.3 | 47.5 | — |
| 20 | 100 | 82.6 | 29.2 | — |
| 21 | 100 | 82.9 | 34.2 | — |
| 22 | 100 | 49.2 | 16.1 | — |
| 23 | 100 | 100 | 90.5 | 67.0 |
| Known compounds (Reference compounds) | | | | |
| 24 | —% | 100.0% | 100.0% | 21.1% |
| 25 | — | 100.0 | 89.7 | — |
| 26 | 90.8 | 84.8 | 61.9 | — |
| 27 | 82.9 | 46.5 | 19.2 | — |
| 28 | — | 91.8 | 88.4 | 30.6 |
| 29 | 100.0 | 53.3 | 12.3 | — |
| 30 | 91.5 | 89.9 | 50.3 | — |
| 31 | 85.5 | 86.8 | 2.9 | — |
| 32 | 100.0 | 100.0 | 100.0 | 11.2 |
| 33 | 91.8 | 29.3 | — | — |
| 34 | 88.1 | 75.8 | 28.1 | — |
| 35 | 82.6 | 65.2 | 33.8 | — |
| 36 | 87.5 | 45.8 | 23.3 | — |
| 37 | 82.4 | 42.3 | 15.7 | — |
| 38 | 94.0 | 92.6 | 34.1 | — |
| 39 | — | 90.5 | 90.2 | 57.0 |
| 40 | 91.5 | 53.8 | 16.7 | — |
| 41 | 87.5 | 59.4 | 50.0 | — |
| 42 | 93.8 | 17.4 | — | — |
| 43 | 91.3 | 76.3 | 43.2 | — |
| 44 | 95.1 | 27.6 | — | — |
| 45 | 85.6 | 78.5 | 28.7 | — |
| 46 | 76.5 | 58.7 | 13.5 | — |
| 47 | 82.7 | 43.5 | 15.5 | — |
| 48 | 71 | 20 | 2 | — |
| 49 | 67 | 12 | −6 | — |
| 50 | 36 | — | 0 | — |
| 51 | 2 | — | 8 | — |
| 52 | 92 | 38 | 8 | — |
| 53 | 88 | 8 | 0 | — |
| 54 | 55 | 25 | 3 | — |
| 55 | 90 | 8 | 5 | — |
| 56 | 48 | 22 | 6 | — |
| 57 | 100 | 86 | 18 | — |
| 58 | 31 | 13 | 6 | — |
| 59 | 15 | 14 | 2 | — |
| 60 | 5 | — | 2 | — |
| 61 | 5 | 3 | 0 | — |
| 62 | 28 | 15 | 0 | — |
| 63 | 12 | 8 | 0 | — |
| 64 | 17 | — | 0 | 0 |
| 65 | 5 | 0 | 0 | — |
| 66 | 27 | 13 | 0 | — |
| 67 | 7 | 0 | 0 | — |
| 68 | 12 | 5 | 0 | — |

TABLE 1-continued

Inhibition effect of carbostyril derivatives on collagen-induced aggregation in rabbit platelet

| Test compound No. | Concentration of the test compound solution | | | |
|---|---|---|---|---|
| | $10^{-4}$ mole | $10^{-5}$ mole | $10^{-6}$ mole | $10^{-7}$ mole |
| 69 | 65 | 9 | 7 | — |

TABLE 2

Inhibition effect of carbostyril derivatives on ADP-induced aggregation in rabbit platelet

| Test compound No. | Concentration of the test compound solution | | | |
|---|---|---|---|---|
| | $10^{-4}$ mole | $10^{-5}$ mole | $10^{-6}$ mole | $10^{-7}$ mole |
| Compounds of the present invention | | | | |
| 1 | 100% | 86% | 45% | —% |
| 2 | 100 | 82 | 7.2 | — |
| 3 | 100 | 31 | 10 | — |
| 4 | 85.7 | 13.7 | — | — |
| 5 | 100 | 54.7 | 7.1 | — |
| 6 | 75 | 24.6 | 14.7 | — |
| 7 | 100 | 64.3 | 18.6 | — |
| 8 | 100 | 72.1 | 12.2 | — |
| 9 | 100 | 84.9 | 40.1 | 5.6 |
| 10 | 100 | 80.7 | 42.6 | 7.1 |
| 11 | 100 | 49.5 | 22.4 | — |
| 12 | 100 | 40.2 | 8.3 | — |
| 13 | 100 | 30.1 | 5.3 | — |
| 14 | 100 | 87.7 | 15.7 | — |
| 15 | 100 | 100 | 25.8 | — |
| 16 | 100 | 27.9 | 4.9 | — |
| 17 | 100 | 25.1 | 4.3 | — |
| 18 | 100 | 42.1 | 7.0 | — |
| 19 | 100 | 63.2 | 12.0 | — |
| 20 | 100 | 73.2 | 28.8 | — |
| 21 | 100 | 60.6 | 18.6 | — |
| 22 | 100 | 63.2 | 28.8 | — |
| 23 | 100 | 100 | 91.9 | 40.4 |
| Known compounds (Reference compounds) | | | | |
| 24 | 100.0% | 73.0% | 42.4% | 4.3% |
| 25 | — | 90.3 | 54.3 | — |
| 26 | 91.5 | 75.0 | 20.8 | — |
| 27 | 70.4 | 16.1 | 6.9 | — |
| 28 | — | 90.7 | 61.2 | 18.9 |
| 29 | 87.2 | 5.4 | — | — |
| 30 | 89.8 | 82.9 | 38.4 | — |
| 31 | 91.7 | 41.1 | — | — |
| 32 | 92.8 | 70.4 | 5.8 | — |
| 33 | 53.9 | 18.4 | — | — |
| 34 | 87.5 | 12.5 | 16.9 | — |
| 35 | 71.7 | 33.8 | 12.7 | — |
| 36 | 39.6 | 24.8 | 18.0 | — |
| 37 | 41.3 | 25.7 | 15.1 | — |
| 38 | 88.3 | 26.8 | 10.8 | — |
| 39 | — | 91.7 | 62.1 | 32.8 |
| 40 | 82.5 | 38.7 | 12.3 | — |
| 41 | 86.4 | 37.5 | 12.6 | — |
| 42 | 24.6 | 16.2 | — | — |
| 43 | 82.5 | 31.7 | 13.5 | — |
| 44 | 36.8 | 5.3 | — | — |
| 45 | 71.5 | 32.7 | 10.5 | — |
| 46 | 73.6 | 26.1 | 8.7 | — |
| 47 | 43.2 | 22.3 | 13.4 | — |
| 48 | 57 | 25 | 5 | — |
| 49 | 86 | 54 | −6 | — |
| 50 | 36 | — | 0 | — |
| 51 | −18 | — | 14 | — |
| 52 | 100 | 97 | 10 | — |
| 53 | 100 | 79 | 20 | — |

TABLE 2-continued

Inhibition effect of carbostyril derivatives on ADP-induced aggregation in rabbit platelet

| Test compound No. | Concentration of the test compound solution | | | |
|---|---|---|---|---|
| | $10^{-4}$ mole | $10^{-5}$ mole | $10^{-6}$ mole | $10^{-7}$ mole |
| 54 | 74 | 38 | 7 | — |
| 55 | 65 | 18 | 2 | — |
| 56 | 82 | 58 | 0 | — |
| 57 | 100 | 90 | 25 | — |
| 58 | 37 | 15 | 10 | — |
| 59 | 13 | 8 | 7 | — |
| 60 | 3 | — | 11 | — |
| 61 | 10 | 5 | 3 | — |
| 62 | 52 | 23 | 5 | — |
| 63 | 28 | 16 | 7 | — |
| 64 | 18 | 13 | 7 | — |
| 65 | 13 | 6 | 0 | — |
| 66 | 22 | 17 | 8 | — |
| 67 | 14 | 6 | 0 | — |
| 68 | 32 | 17 | 9 | — |
| 69 | 7 | 0 | — | — |

Pharmacological Test 2

The obstructive action against cyclic AMP phosphodiesterase was measured according to the activity measuring method described in "Biochimica et Biophysica Acta", Vol. 429, pp. 485–497 (1976) and "Biochemical Medicine", Vol. 10, pp. 301–311 (1974).

That is, for determining the obstructive activity against cyclic AMP phosphodiesterase, 10 ml of a solution obtained by adding 1 mmol of $MgCl_2$ into 50 mmol of tris-hydrochloric acid buffer with pH 7.4 was added to the platelets obtained by further centrifuging the above-said rabbit PRP at 3,000 r.p.m. for 10 minutes, and the suspended platelets were ground by a Teflon potter type homogenizer. This was followed by two times of freezing and thawing treatment and 300-second fracturing with 200 watt supersonic waves. After additional 60-minute centrifugation with 100,000 G, the supernatant was collected to use it as a crude enzyme solution.

10 Milliliters of this crude buffer solution was added to a 1.5×20 cm DEAE-cellulose column which has previously been buffered with 50 mM of tris-acetate buffer (pH 6.0), followed by washing and elution with 30 ml of 50 mM tris-acetate buffer, and this buffer solution was subjected to linear gradient elution with 0 to 0.5 moles of sodium acetate-tris-acetate buffer (total amount of elute was 300 ml.). The flow rate was 0.5 ml/min, and 5 ml of each fraction was batched out. This operation gave a fraction which has low activity of less than 2 n mole/ml/min with high (100 μmole) cyclic AMP substrate concentration and still has high activity of over 100 p mole/ml/min with low (0.4 μmole) cyclic AMP substrate concentration. This fraction was used as cyclic AMP phosphodiesterase.

0.1 Milliliter of an aqueous solution of each test compound of a specified concentration was mixed with 40 mmol of tris-hydrochloric acid buffer (pH 8.0, containing 50 μg of cow serum albumin and 4 mmol of $MgCl_2$) containing predetermined 1.0 μmol of cyclic AMP (tritium cyclic AMP), and 0.2 ml of this mixed solution was used as substrate solution.

0.2 Milliliter of the above-prepared cyclic AMP phosphodiesterase of a predetermined concentration was added to said substrate solution and the mixture was reacted at 30° C. for 20 minutes, producing tritium 5'-AMP from the tritium cyclic AMP.

The reaction system was then immersed in boiling water for 2 minutes to stop the reaction, and then this reaction solution was cooled in ice water and, for converting the produced tritium 5'-AMP into tritium adenosine, the solution was added with 0.05 ml (1 mg/ml) of snake poison as 5'-nucleotidase and reacted at 30° C. for 10 minutes. The whole amount of this reaction solution was then added to a cation exchange resin (AG 500 W×4, 200–400 meshes, manufactured by Bio-Rad Co., column size: 0.5×1.5 cm), and the produced tritium anodesine alone was allowed to combine, washed with 6 ml of distilled water and eluted with 1.5 ml of 3 N-ammonia water. The whole quantity of the elutant was added with 10 ml of a triton-toluene type scintillator and the produced tritium adenosine was measured by a liquid scintillation counter to determine the phosphodiesterase activity.

In this way, the phosphodiesterase activation value (Vs) of the test compounds of the respective concentrations was determined, and the phosphodiesterase obstruction rate (%) was determined from said activation value (Vs) and control value (Vc) (obtained from water not containing any test compound) from the following formula:

$$\text{Phosphodiesterase obstruction rate (\%)} = \frac{Vc - Vs}{Vc} \times 100$$

Known 1-methyl-3-isobutylxanthine was used as control. The results are shown in Table 3.

TABLE 3

| Compounds | IC$_{50}$ (mole) |
|---|---|
| Compounds of the present invention | |
| 1 | $1.5 \times 10^{-7}$ |
| 3 | $4.0 \times 10^{-7}$ |
| 4 | $6.0 \times 10^{-7}$ |
| 6 | $5.2 \times 10^{-8}$ |
| 10 | $1.2 \times 10^{-8}$ |
| 12 | $2.5 \times 10^{-8}$ |
| 14 | $5.2 \times 10^{-8}$ |
| 15 | $4.0 \times 10^{-8}$ |
| Known compounds | |
| 26 | $6.6 \times 10^{-9}$ |
| 39 | $1.6 \times 10^{-8}$ |
| 1-Methyl-3-isobutyl-xanthine | $5.4 \times 10^{-7}$ |

Pharmacological Test 3

Positive inotropic effects of the novel carbostyril derivatives of the present invention were tested according to a method described by M. Endoh and K. Hashimoto, in "American Journal of Physiology", Vol. 218, No. 5, May, 1970, pages 1459–1463 as follows:

Adult bastard dogs of both sexes, weighing 8–12 kg, were anesthetized with pentobarbital-Na at a rate of 30 mg/kg by intraveneous administration. After another intraveneous administration of sodium heparin, 1,000 μ/kg, the test dog was sacrificed by blood letting. The heart of the dog was excised and immediately plunged into Locke's solution, then the arterial papillary muscle was excised out with interventicular septum. The septal artery was carefully isolated and cannulated with a polyethylene cannula and was ligated with thread. Septal arteries those of connected to other than the arterial papillary muscle were ligated with thread. Next, the donor adult bastard dogs, weighing 18–27 kg, were anesthetized with pentabarbital-Na (30 mg/kg, intraveneous injection), and further treated with intravenous administration of sodium heparin (1,000 μ/kg). The arterial papillary muscle was perfused through the septal artery being cannulated with the polyethylene cannula with the blood conducted from the carotid artery of the donor dog by aid of Peristaric pump. The perfusion pressure was maintained at 100 mmHg constantly. Then the muscle was electrically stimulated by an electronic stimulator through bipolar electrodes in contact with the interventicular septum. The strength of stimulation was 2 X (the minimum value for appearing the action), frequency 2 Hz, pulse duration 2 msec.

The isometric contraction generated was measured through a force-displacement transducer. The amount of blood flow in the coronary arteries was measured by determining the amount of the blood flow conducted to the septal artery by electromagnetic flow meter. All the data were recorded on an ink-writing recorder.

A solution containing a compound to be tested was injected into the septal artery through the rubber tube connected close to the shunk of the polyethylene cannula, in an amount of 10–30 μl.

The results obtained is shown in Table 4, in which the increasement (%) of contraction is indicated as the ratio of the contractions before and after the administration (injection) of the solution containing the test compound.

TABLE 4

| Compound tested (Sample No.) | Dosage (n mol) | Increasing of inotropic (%) |
|---|---|---|
| 1 | 3 | 8.2 |
|  | 30 | 54.5 |
| 4 | 10 | 10 |
|  | 100 | 62.5 |
| 8 | 30 | 38.7 |
|  | 100 | 89.4 |
| 2 | 10 | 38.9 |
|  | 30 | 94.3 |
| 17 | 10 | 2.7 |
|  | 30 | 51.4 |

Pharmacological Test 4

Increasing effect of cerebral blood flow was measured by a procedure similar to that disclosed in Journal of Surgical Research Vol. 8, No. 10, pages 475–481 (1968). Thus, a bastard dog (male, 12–20 kg of body weight) was fixed in a prone (position) and was anesthetized with 20 mg/kg of pentobarbital sodium and made forced breathing to kept the frequency of respiration at 20 times/minutes. Then, the skull was bared and the surface bone was removed to expose the venous sinus by using grinder and the venous blood was took out from the venas which was cannulizated. The amount of venous blood flow was measured by using an electromagnetic blood flow meter and next measured by using drop-counter by measuring the number of drops of blood per 10 seconds.

The increasing effect of cerebral blood flow was calculated by comparing the number of blood drops in 30 seconds at the peak of increasement shown before and after the administration of compound to be tested. The each of compounds to be tested was dissolved in dimethylformamide and diluted with physiological saline solution and administered through a cannule being inserted into the profunda femoris vein.

As to the reference compound, papaverine was used. The results obtained were indicated in Table 5.

TABLE 5

| Compounds tested | Dosage (μg/kg) | Increasing effect of cerebral blood flow (%) |
|---|---|---|
| Compounds of the present invention | | |
| 1 | 100 | 89.8 |
| 4 | 300 | 64.2 |
| 5 | 100 | 43.5 |
| 7 | 300 | 80.2 |
| 9 | 100 | 85.3 |
| 12 | 300 | 73.5 |
| 13 | 30 | 98.9 |
| 14 | 100 | 51.6 |
| 16 | 100 | 63.2 |
| 17 | 100 | 34.4 |
| Papaverin | 1,000 | 86.0 |

(2) Deoxycorticosteroneacetate (DOCA)/saline hypertension rats (DHR)

Wistar strain male rats having 150–170 g of body weight, were anesthetized with ether and the left-side kidney was enucleated. One (1) week after the operation, 10 mg/kg of DOCA was injected subcutaneously once a week and 1% NaCl aqueous solution was given as drinking water. Five (5) weeks after the operation, rats having the maximum blood pressure over 150 mmHg were selected and used as test animals which were abstained from food for overnight.

Each of compounds to be tested were administered orally and the blood pressure was measured before the administration and 1, 2, 4, 6 and 8 hours after the administration. The results obtained were indicated in Table 6. The blood pressure was measured by using Recorder (Rectihoriz type 8S, San-ei Instrument) and Electrosthygmomanometer PE-300 (Macro Bio-systems, Houston, Tex.).

TABLE 6

| Compound tested (Sample No.) | Dosage (mg/kg) | Number of test runs | Type of rats | Blood pressure (mmHg) Before the administration* |
|---|---|---|---|---|
| 1 | 30 | 5 | RHR | 196.2 ± 8.2 |
| 1 | 30 | 5 | DHR | 176.6 ± 3.8 |
| 9 | 30 | 4 | RHR | 204.9 ± 10.5 |
| 9 | 30 | 4 | DHR | 172.8 ± 8.6 |
| 2 | 30 | 5 | RHR | 194.6 ± 4.2 |
| 2 | 30 | 5 | DHR | 173.0 ± 6.9 |
| 16 | 30 | 5 | RHR | 192.4 ± 10.3 |
| 16 | 30 | 5 | DHR | 203.4 ± 6.2 |
| 17 | 30 | 5 | RHR | 249.2 ± 5.5 |
| 17 | 30 | 5 | DHR | 205.4 ± 5.3 |

*Mean value ± standard deviation.

| Maximum blood pressure (mmHg) After the administration** | | | | |
|---|---|---|---|---|
| 1 hour | 2 hours | 4 hours | 6 hours | 8 hours |
| −27.0 ± 14.0 | −28.6 ± 16.4 | −32.4 ± 15.2 | −35.0 ± 11.5 | −41.3 ± 17.2 |
| −46.0 ± 11.7 | −42.6 ± 6.5 | −37.6 ± 5.2 | −34.4 ± 10.5 | −29.0 ± 10.5 |
| −10.1 ± 6.2 | −11.6 ± 9.6 | −14.2 ± 5.0 | −8.0 ± 2.6 | |
| −51.2 ± 14.0 | −44.6 ± 14.6 | −42.4 ± 13.9 | −34.0 ± 10.2 | |
| −4.8 ± 6.4 | −4.8 ± 3.7 | −3.2 ± 4.0 | | |
| −63.0 ± 9.1 | −30.4 ± 9.9 | −42.8 ± 5.5 | −24.1 ± 6.8 | |
| −27.0 ± 9.0 | −11.0 ± 5.6 | −10.8 ± 7.5 | −9.8 ± 3.8 | |
| −20.2 ± 8.0 | −21.2 ± 9.7 | −16.2 ± 6.8 | −6.5 ± 8.5 | |
| −25.5 ± 7.0 | −23.3 ± 9.6 | −27.0 ± 14.1 | −33.7 ± 10.2 | −29.8 ± 9.7 |
| −2.5 ± 4.0 | −8.7 ± 3.3 | −9.3 ± 8.6 | | |

**Difference (mean value ± standard deviation) of the value measured before the administration substracted the value measured after the administration at each hours.

Phamacological Test 5

Hypotensive effect of the compounds were measured by determining the maximum blood pressure of the test animals according to a procedure of Tail-cuff method.

Test animals used were the following two types.

(1) Gold blatt type renoprival hypertension rats (RHR)

Wistar strain male rats having, 160–180 g of body weight, were anesthetized with ether and the left-side renal artery was pluged with a silver clip having 0.2 mm inside diameter, while the right-side renal artery was kept as it was without operation. Four (4) weeks after the operation, rats having the maximum blood pressure over 150 mmHg were selected and used as test animals which were abstained from food for overnight.

Phamacological Test 6

Acute Toxicity Test

The test compounds were administered orally to the mice and $LD_{50}$ (mg/kg) of the compounds was determined. The results are shown in Table 7 below.

TABLE 7

| Test compound | $LD_{50}$ (mg/kg) Male mice Oral administration |
|---|---|
| Compounds of the present invention | |
| 1 | >1000 |
| 2 | >1000 |
| 3 | >1000 |
| 4 | >1000 |
| 5 | >1000 |
| 6 | >1000 |
| 7 | >1000 |
| 8 | >1000 |

TABLE 7-continued

| Test compound | LD$_{50}$ (mg/kg) Male mice Oral administration |
|---|---|
| 9 | >1000 |
| 10 | >1000 |
| 11 | >1000 |
| 12 | >1000 |
| 13 | >1000 |
| 14 | >1000 |
| 15 | >1000 |
| 16 | >1000 |
| 17 | >1000 |
| 18 | >1000 |
| 19 | >1000 |
| 20 | >1000 |
| 21 | >1000 |
| 22 | >1000 |
| 23 | >1000 |

Pharmacological Test 7

(Test of increasing effect of heart rate)

Wistar strain male rats, having 180-230 g of body weight, were abstained from food for 24 hours, the electrocardiograms introduced from the second induction period were recorded on oscillograph. The heart rate was calculated from the electrocardiograms by observing them for 10 seconds several times. After the heart rate showed a constant value when the rats became in sedative condition, then 30 mg/kg of each of the test compounds was orally administered, in the form of a suspension being added with gum arabic, in an amount of 5 ml/kg as the suspension. 60 Minutes after the administration, the heart rate was measured and increasing effect of the heart rate was calculated. The results obtained were indicated in Table 8. Generally, an average heart rate of an usual Wistar strain male rat is about 320 beat/minute.

TABLE 8

| Compounds tested (Sample No.) | Increasing effect of heart rate (Beat/min.) |
|---|---|
| Blank test (Compound tested was not used) | ±0 |
| Compounds of the present invention | |
| No. 1 | 42 |
| No. 6 | 40 |
| No. 14 | 32 |
| Known compound | |
| No. 39 | 104 |

The present invention will be illustrated more in specifically by way of the following examples, in which the preparation of the compounds to be used for the starting materials will be shown as Reference examples and the preparation of the objective compounds will be shown as Examples.

REFERENCE EXAMPLE 1

Into 100 g of cyclohexylamine was added 41 g of ethylene chloride and the mixture was stirred at about 160° C. for 10 hours. After cooling the reaction mixture to a room temperature, 100 ml of 10 N-NaOH aqueous solution was added to the reaction mixture and the organic layer was obtained by using a separating funnel and thus obtained organic layer was dried with KOH. KOH was removed by filtration and the mother liquor was distilled under a reduced pressure. 48 Grams of N-(2-hydroxyethyl)cyclohexylamine was obtained as an oily substance. Boiling point: 132°-135° C. (18 mmHg).

By a method similar to that described in Reference Example 1, there were obtained compounds in Reference Examples 2-19 as follows.

REFERENCE EXAMPLE 2

N-(3-Hydroxypropyl)-N-cyclohexylamine.
Colorless plate-like crystals.
Melting point: 68.5°-69.5° C.

REFERENCE EXAMPLE 3

N-(4-Hydroxybutyl)-N-cyclohexylamine.
Colorless crystals.
Boiling point: 158°-163° C./18 mmHg.

REFERENCE EXAMPLE 4

N-(2-Hydroxypropyl)-N-cyclohexylamine.
Colorless crystals.
Boiling point: 117°-119° C./17 mmHg.

REFERENCE EXAMPLE 5

N-(2-Hydroxyethyl)-N-cyclooctylamine.
Colorless liquid.
Boiling point: 98°-103° C./0.1 mmHg.

REFERENCE EXAMPLE 6

N-(2-Hydroxyethyl)-N-cyclohexylmethylamine.
Colorless crystals.
Boiling point: 131°-133° C./12 mmHg.

REFERENCE EXAMPLE 7

N-(3-Hydroxypropyl)-N-cyclohexylmethylamine.
Colorless liquid.
Boiling point: 135°-142° C./10 mmHg.

REFERENCE EXAMPLE 8

N-(4-Hydroxybutyl)-N-cyclohexylmethylamine.
Colorless liquid.
Boiling point: 158°-160° C./12 mmHg.

REFERENCE EXAMPLE 9

N-(2-Hydroxypropyl)-N-cyclohexylmethylamine.
Colorless liquid.
Boiling point: 138°-145° C./10 mmHg.

REFERENCE EXAMPLE 10

N-(1-Methyl-2-hydroxypropyl)-N-cyclohexylmethylamine.
Colorless crystals.
Boiling point: 120°-126° C./10 mmHg.

REFERENCE EXAMPLE 11

N-(5-Hydroxypentyl)-N-cyclohexylmethylamine.
Colorless liquid.
Boiling point: 139°-142° C./2 mmHg.

REFERENCE EXAMPLE 12

N-Ethyl-N-(2-tetrahydropyranylmethyl)amine.
Colorless liquid.
Boiling point: 69°-71° C./10 mmHg.

REFERENCE EXAMPLE 13

N-Propyl-N-(2-tetrahydropyranylmethyl)amine.
Colorless liquid.
Boiling point: 78°-80° C./9 mmHg.

REFERENCE EXAMPLE 14

N-Butyl-N-(2-tetrahydropyranylmethyl)amine.
Colorless liquid.
Boiling point: 96°–98° C./10 mmHg.

REFERENCE EXAMPLE 15

N-(2-Hydroxyethyl)-N-(2-tetrahydropyranylmethyl)amine.
Colorless crystals.
Boiling point: 136°–138° C./11 mmHg.

REFERENCE EXAMPLE 16

N-(3-Hydroxypropyl)-N-(2-tetrahydropyranylmethyl)amine.
Colorless liquid.
Boiling point: 150°–155° C./11 mmHg.

REFERENCE EXAMPLE 17

3-[N-(2-Hydroxyethyl)aminomethyl]pyridine.
Pale yellow liquid.
Boiling point: 134°–142° C./0.2 mmHg.

REFERENCE EXAMPLE 18

N-(2,3-Dihydroxypropyl)-N-cyclohexylamine.
Colorless liquid.
Boiling point: 114°–118° C./0.4 mmHg.

REFERENCE EXAMPLE 19

N-(2-Hydroxybutyl)-N-cyclohexylamine.
Colorless crystals.
Boiling point: 122°–125° C./12 mmHg.

REFERENCE EXAMPLE 20

Into 100 ml of diethylether was added 19 g of γ-bromocrotonylchloride, while the mixture was stirred at 0°–10° C., 25 g of N-(2-hydroxyethyl)cyclohexylamine was added dropwise. After the addition then the reaction mixture was stirred at the same temperature for 3 hours. The reaction mixture was extracted with ether and the ether extract was washed with 2 N-HCl, a diluted NaHCO₃ aqueous solution saturated with NaCl, and water in this order. The organic layer was dried with anhydrous Na₂SO₄ and the solvent was removed by distillation. 17.5 Grams of N-cyclohexyl-N-(2-hydroxyethyl)-γ-bromocrotonamide was obtained as an oil substance. The chemical structure of this substance was identified by the NMR spectrum and the data of elementary analysis.

REFERENCE EXAMPLE 21

Into 200 ml of N,N-dimethylformamide and 50 ml of water was added 16 g of 6-hydroxycarbostyril and 17 g of K₂CO₃, while the mixture was stirred at a room temperature, 31 g of N-cyclohexyl-N-(2-hydroxyethyl)-γ-bromocrotonamide was added dropwise. After the addition the reaction mixture was stirred for 3 hours and was concentrated. To the residue thus obtained 500 ml of chloroform was added and washed with water, a diluted NaOH aqueous solution and water. The organic layer was concentrated. The residue thus obtained was recrystallized from methanol-water to obtain 27 g of 6-{3-[N-(2-hydroxyethyl)-N-cyclohexylaminocarbonyl]-2-propenyloxy}-carbostyril as in the form of colorless needle-like crystals. The chemical structure of this substance was identified by the NMR spectrum and the data of elementary analysis.

EXAMPLE 1

Into 100 ml of dimethylformamide were added 2.5 g of 6-(3-carboxypropoxy)carbostyril and 1.7 ml of triethylamine. The outside of the reaction vessel containing the above mentioned mixture was ice-cooled and 1.4 ml of isobutyl chloroformate was added dropwise to the mixture under stirring condition. After the addition operation, stirring was continued for 30 minutes and 1.75 g of N-(2-hydroxyethyl)cyclohexylamine was added to the reaction mixture and further stirred at a room temperature for 3 hours.

After the reaction was completed, the solvent was removed by distillation and the residue thus obtained was extracted with about 300 ml of chloroform and washed with a diluted NaHCO₃ aqueous solution, water, a diluted hydrochloric acid and water in this order. The chloroform was removed by distillation to obtain a residue and the residue was recrystallized from chloroform-petroleum ether to obtain 1.9 g of 6-{3-[N-(2-hydroxyethyl)-N-cyclohexylaminocarbonyl]propoxy}-carbostyril in the form of colorless needle-like crystals. Melting point: 165°–166° C.

EXAMPLE 2

Into 100 ml of chloroform were added 2.5 g of 6-(3-carboxypropoxy)-3,4-dihydrocarbostyril and 1.65 g of 1,8-diazabicyclo[5,4,0]undecene-7. The outside of the reaction vessel containing the above mentioned mixture was ice-cooled and 1.5 ml of isobutyl chloroformate was added dropwise to the mixture under stirring condition. After the addition operation, stirring was continued for 30 minutes and 2.0 g of N-(2-hydroxyethyl)cyclohexylamine was added to the reaction mixture and further stirred at a room temperature for 2 hours. After the reaction was completed, the chloroform solution of the reaction product was washed with a diluted NaHCO₃ aqueous solution, a diluted hydrochloric acid and water in this order. The chloroform solution was dried with anhydrous Na₂SO₄, then the chloroform was removed by distillation and the residue thus obtained was recrystallized from chloroform-petroleum ether to obtain 2.1 g of 6-{3-[N-(2-hydroxyethyl)-N-cyclohexylaminocarbonyl]propoxy}-3,4-dihydrocarbostyril in the form of colorless needle-like crystals. Melting point: 139°–141.5° C.

By a method similar to that described in Example 2, there were obtained compounds in Examples 3–18 as follows.

EXAMPLE 3

5-{3-[N-(2-Hydroxyethyl)-N-cyclohexylaminocarbonyl]propoxy}-3,4-dihydrocarbostyril.
Colorless needle-like crystals.
Melting point: 130°–131.5° C.

EXAMPLE 4

6-{3-[N-(2-Hydroxybutyl)-N-cyclohexylaminocarbonyl]propoxy}-3,4-dihydrocarbostyril.
Colorless needle-like crystals.
Melting point: 132°–133° C.

EXAMPLE 5

6-{3-[N-(2-Hydroxyethyl)-N-cyclooctylaminocarbonyl]propoxy}-3,4-dihydrocarbostyril.
Colorless powdery crystals.
Melting point: 104°–107° C.

EXAMPLE 6

6-{3-[N-(2-Hydroxypropyl)-N-cyclohexylaminocarbonyl]propoxy}carbostyril.
Colorless needle-like crystals.
Melting point: 201°–203° C.

EXAMPLE 7

6-{3-[N-(4-Hydroxybutyl)-N-cyclohexylaminocarbonyl]propoxy}carbostyril.
Colorless powdery crystals.
Melting point: 153°–155° C.

EXAMPLE 8

6-{4-[N-(2-Hydroxypropyl)-N-cyclohexylaminocarbonyl]butoxy}-3,4-dihydrocarbostyril.
Colorless needle-like crystals.
Melting point: 120.5°–122.5° C.

EXAMPLE 9

6-{4-[N-(2-Hydroxyethyl)-N-cyclohexylaminocarbonyl]butoxy}-3,4-dihydrocarbostyril.
Colorless powdery crystals.
Melting point: 122°–123.5° C.

EXAMPLE 10

6-{4-[N-(2-Hydroxybutyl)-N-cyclohexylaminocarbonyl]butoxy}-3,4-dihydrocarbostyril.
Colorless needle-like crystals.
Melting point: 91°–93° C.

EXAMPLE 11

6-{4-[N-(2,3-Dihydroxypropyl)-N-cyclohexylaminocarbonyl]butoxy}-3,4-dihydrocarbostyril.
Colorless prism-like crystals.
Melting point: 112.5°–113.5° C.

EXAMPLE 12

6-{4-[N-(2-Hydroxybutyl)-N-cyclopentylaminocarbonyl]butoxy}-3,4-dihydrocarbostyril.
Colorless needle-like crystals.
Melting point: 102°–103° C.

EXAMPLE 13

6-{4-[N-(2-Hydroxybutyl)-N-cyclohexylaminocarbonyl]butoxy}carbostyril.
Colorless powdery crystals.
Melting point: 127°–128.5° C.

EXAMPLE 14

6-{4-[N-(2,3-Dihydroxypropyl)-N-cyclohexylaminocarbonyl]butoxy}carbostyril.
Colorless needle-like crystals.
Melting point: 138°–140° C.

EXAMPLE 15

6-{4-[N-(2-Hydroxybutyl)-N-cyclooctylaminocarbonyl]butoxy}carbostyril.
Colorless powdery crystals.
Melting point: 86°–89° C.

EXAMPLE 16

6-{5-[N-(2-Hydroxybutyl)-N-cyclohexylaminocarbonyl]pentyloxy}-3,4-dihydrocarbostyril.
Colorless powdery crystals.
Melting point: 98°–100° C.

EXAMPLE 17

7-{3-[N-(3-Hydroxypropyl)-N-cyclohexylaminocarbonyl]propoxy}-3,4-dihydrocarbostyril.
Colorless powdery crystals.
Melting point: 140°–142° C.

EXAMPLE 18

6-{4-[N-(2-Hydroxyethyl)-N-cyclohexylaminocarbonyl]butoxy}carbostyril.
Colorless granular crystals.
Melting point: 134°–135° C.

EXAMPLE 19

Into 300 ml of chloroform were added 9.9 g of 6-(3-carboxypropoxy)carbostyril and 6.5 ml of DBU. The outside of the reaction vessel containing the abovementioned mixture was ice-cooled and 5.7 ml of isobutyl chloroformate was added dropwise under stirring condition. After the addition operation, stirring was continued for 1 hour at a room temperature and 5.4 g of 2-ethylaminopyridine was added dropwise, then the reaction was continued for 5 hours under stirring condition. The reaction mixture was washed with a diluted NaHCO$_3$ aqueous solution and water, and was concentrated. The residue thus obtained was treated by a silica-gel column chromatography (solvent used was a mixture of chloroform:methanol=20:1) and the elute thus obtained was concentrated then was recrystallized from methanol, to obtain 4.5 g of 6-{3-[N-ethyl-N-(2-pyridyl)aminocarbonyl]propoxy}carbostyril in the form of colorless needle-like crystals. Melting point: 148°–149° C.

By a method similar to that described in Example 19, there were obtained compounds in Examples 20–40 as follows:

EXAMPLE 20

6-{3-[N-Ethyl-N-(3-pyridyl)aminocarbonyl]propoxy}carbostyril.
Colorless needle-like crystals.
Melting point: 148°–149° C.

EXAMPLE 21

6-{3-[N-Methyl-N-(3-pyridylmethyl)aminocarbonyl]propoxy}carbostyril.
Colorless needle-like crystals.
Melting point: 169.5°–171° C.

EXAMPLE 22

6-{3-[N-Ethyl-N-(3-pyridylmethyl)aminocarbonyl]propoxy}carbostyril.
Colorless needle-line crystals.
Melting point: 145°–147° C.

EXAMPLE 23

6-{3-[N-Methyl-N-(2-furylmethyl)aminocarbonyl]propoxy}carbostyril.
Colorless needle-like crystals.
Melting point: 125.5°–127.5° C.

EXAMPLE 24

6-{3-[N-Methyl-N-(2-tetrahydrofurylmethyl)aminocarbonyl]propoxy}carbostyril.
Colorless needle-like crystals.
Melting point: 123°–125° C.

EXAMPLE 25

6-{3-[N-Methyl-N-(2-thienylmethyl)aminocarbonyl]propoxy}carbostyril.
Colorless needle-like crystals.
Melting point: 133.5°–135° C.

EXAMPLE 26

6-{3-[N-Methyl-N-(2-3,4-dihydro-2H-pyranylmethyl)aminocarbonyl]propoxy}carbostyril.
Colorless needle-like crystals.
Melting point: 133.5°–135° C.

EXAMPLE 27

6-{3-[N-Methyl-N-(2-tetrahydropyranylmethyl)aminocarbonyl]propoxy}carbostyril.
Colorless granular crystals.
Melting point: 150°–151.5° C.

EXAMPLE 28

6-{3-[N-Methyl-N-(2-tetrahydropyranylmethyl)aminocarbonyl]propoxy}-3,4-dihydrocarbostyril.
Colorless prism-like crystals.
Melting point: 121.5°–123.5° C.

EXAMPLE 29

5-{3-[N-(2-Hydroxyethyl)-N-cyclohexylaminocarbonyl]propoxy}-3,4-dihydrocarbostyril.
Colorless needle-like crystals.
Melting point: 130°–131.5° C.

EXAMPLE 30

6-[N-Ethyl-N-(3-pyridylmethyl)aminocarbonylmethoxy]-3,4-dihydrocarbostyril.
Colorless needle-like crystals.
Melting point: 82°–84° C.

EXAMPLE 31

6-{5-[N-Methyl-N-(2-tetrahydropyranylmethyl)aminocarbonyl]pentyloxy}carbostyril.
Colorless needle-like crystals.
Melting point: 81°–83° C.

EXAMPLE 32

8-{3-[N-Methyl-N-(2-tetrahydropyranylmethyl)aminocarbonyl]propoxy}carbostyril.
Colorless needle-like crystals.
Melting point: 115.5°–117° C.

EXAMPLE 33

6-{4-[N-Ethyl-N-(2-tetrahydropyranylmethyl)aminocarbonyl]butoxy}-3,4-dihydrocarbostyril.
Colorless needle-like crystals.
Melting point: 87°–88.5° C.

EXAMPLE 34

6-{4-[N-Propyl-N-(2-tetrahydropyranylmethyl)aminocarbonyl]butoxy}-3,4-dihydrocarbostyril.
Colorless needle-like crystals.
Melting point: 77°–79.5° C.

EXAMPLE 35

6-{4-[N-Butyl-N-(2-tetrahydropyranylmethyl)aminocarbonyl]butoxy}-3,4-dihydrocarbostyril.
Colorless needle-like crystals.
Melting point: 93.5°–95.5° C.

EXAMPLE 36

6-{3-[N-(2-Hydroxyethyl)-N-(2-tetrahydropyranylmethylaminocarbonyl]propoxy}carbostyril.
Colorless needle-like crystals.
Melting point: 175.5°–177° C.

EXAMPLE 37

6-{4-[N-(2-Hydroxyethyl)-N-(3-pyridylmethyl)aminocarbonyl]butoxy}-3,4-dihydrocarbostyril.
Colorless needle-like crystals.
Melting point: 80°–82.5° C.

EXAMPLE 38

6-{4-[N-(2-Hydroxyethyl)-N-(2-tetrahydropyranylmethyl)aminocarbonyl]butoxy}-3,4-dihydrocarbostyril.
Colorless needle-like crystals.
Melting point: 117°–118.5° C.

EXAMPLE 39

6-{4-[N-(3-Hydroxypropyl)-N-(2-tetrahydropyranylmethyl)aminocarbonyl]butoxy}-3,4-dihydrocarbostyril.
Colorless needle-like crystals.
Melting point: 98.5°–100° C.

EXAMPLE 40

6-{4-[N-(4-Hydroxybutyl)-N-(2-tetrahydropyranylmethyl)aminocarbonyl]butoxy}-3,4-dihydrocarbostyril.
Colorless needle-like crystals.
Melting point: 114°–116° C.

EXAMPLE 41

Into 100 ml of dimethylformamide were added 3.1 g of 1-benzyl-6-(4-carboxybutoxy)-3,4-dihydrocarbostyril and 1.7 ml of triethylamine. The outside of the reaction vessel containing the above mentioned mixture was ice-cooled and 1.4 ml of isobutyl chloroformate was added dropwise to the mixture under stirring condition. After the addition operation, stirring was continued for 30 minutes and 1.75 g of N-ethyl-N-(2-tetrahydropyranylmethyl)amine was added to the reaction mixture and further stirred at a room temperature for 3 hours. After the reaction was completed, the solvent was removed by distillation and the residue thus obtained was extracted with about 300 ml of chloroform and washed with a diluted NaHCO$_3$ aqueous solution, water, a diluted hydrochloric acid and water in this order. The residue thus obtained was treated by silica-gel column chromatography (solvent used was a mixture of chloroform:methanol=20:1) and the elue thus obtained was concentrated to obtain 2.3 g of 1-benzyl-6-{4-[N-(2-tetrahydropyranylmethyl)-N-ethylaminocarbonyl]butoxy}-3,4-dihydrocarbostyril in the form of a colorless syrupy substance.

IR absorption spectrum: $\nu$ cm$^{-1}$ (neat): 1620, 1690.
Elemental analysis (%): Calculated: C; 75.29, H; 8.28, N; 6.06. Found: C; 75.36, H; 8.13, N; 5.84.

EXAMPLE 42

Into 400 ml of chloroform, were added 5 g of 6-(4-carboxybutoxy)-3,4-dihydrocarbostyril and 3.2 g of DBU. The outside of the reaction vessel containing the above mentioned mixture was ice-cooled and 2.8 g of isobutyl chloroformate was added dropwise to the mixture under stirring condition. After the addition operation, stirring was continued at a room temperature for 30 minutes and 3.9 g of N-(3-hydroxypropyl)-N-cyclohexylmethylamine was added to the reaction mixture and the reaction was continued for 3 hours. After the reaction was completed, the reaction mixture was washed with 1 N-NaOH aqueous solution, 10% HCl and water in this order and was dried with anhydrous Na$_2$SO$_4$. The drying agent was removed by filtration and the thus obtained dried product was concentrated to obtain a residue. The residue was treated by a silica-gel column chromatography (solvent used was a mixture of chloroform:methanol=40:1). The elute obtained was concentrated and was recrystallized from ethyl acetate-petroleum ether. 4.0 Grams of 6-{4-[N-cyclohexylmethyl-N-(3-hydroxypropyl)aminocarbonyl]butoxy}-3,4-dihydrocarbostyril was obtained in the form of colorless needle-like crystals. Melting point: 95°–97° C.

By a method similar to that described in Example 42, there were obtained compounds in Examples 43–67 as follows:

EXAMPLE 43

6-[N-(2-Hydroxyethyl)-N-phenylaminocarbonylmethoxy]carbostyril.
Colorless powdery crystals.
Melting point: 162°–165° C.

EXAMPLE 44

6-{3-[N-(2-Methoxyethyl)-N-cyclohexylaminocarbonyl]propoxy}carbostyril.
Colorless granular crystals.
Melting point: 142.5°–143.5° C.

EXAMPLE 45

6-{3-[N-(2-Hydroxy-1-methylpropyl)-N-cyclohexylmethylaminocarbonyl]propoxy}carbostyril.
Colorless needle-like crystals.
Melting point: 179.5°–181.5° C.

EXAMPLE 46

6-{3-[N-(2-Hydroxyethyl)-N-butylaminocarbonyl]propoxy}carbostyril.
Colorless needle-like crystals.
Melting point: 153°–154° C.

EXAMPLE 47

6-{3-[N-Di-(2-hydroxyethyl)aminocarbonyl]propoxy}carbostyril.
Colorless needle-like crystals.
Melting point: 122°–123.5° C.

EXAMPLE 48

6-{4-[N-(2-Hydroxyethyl)-N-phenylaminocarbonyl]butoxy}-3,4-dihydrocarbostyril.
Colorless needle-like crystals.
Melting point: 113°–116° C.

EXAMPLE 49

6-{4-[N-(2-Hydroxyethyl)-N-benzylaminocarbonyl]butoxy}-3,4-dihydrocarbostyril.
Colorless powdery crystals.
Melting point: 91.5°–93° C.

EXAMPLE 50

6-{4-[N-(2-Hydroxyethyl)-N-cyclohexylmethylaminocarbonyl]butoxy}-3,4-dihydrocarbostyril.
Colorless plate-like crystals.
Melting point: 123°–125° C.

EXAMPLE 51

6-{4-[N-(4-Hydroxybutyl)-N-cyclohexylmethylaminocarbonyl]butoxy}-3,4-dihydrocarbostyril.
Colorless needle-like crystals.
Melting point: 119°–120.5° C.

EXAMPLE 52

6-{4-[N-(2-Hydroxybutyl)-N-cyclohexylmethylaminocarbonyl]butoxy}-3,4-dihydrocarbostyril.
Colorless needle-like crystals.
Melting point: 123°–125° C.

EXAMPLE 53

6-{4-[N-(2-Methoxyethyl)-N-cyclohexylaminocarbonyl]butoxy}carbostyril.
Colorless needle-like crystals.
Melting point: 107°–109° C.

EXAMPLE 54

6-{5-[N-(2-Hydroxyethyl)-N-benzylaminocarbonyl]pentyloxy}-3,4-dihydrocarbostyril.
Colorless powdery crystals.
Melting point: 93.5°–95.5° C.

EXAMPLE 55

6-{3-[N-(2-Benzoyloxyethyl)-N-cyclohexylaminocarbonyl]propoxy}carbostyril.
Colorless needle-like crystals.
Melting point: 94°–97° C.

EXAMPLE 56

6-{4-[N-(5-Hydroxypentyl)-N-cyclohexylmethylaminocarbonyl]butoxy}-3,4-dihydrocarbostyril.
Colorless needle-like crystals.
Melting point: 113.5°–115° C.

EXAMPLE 57

6-{3-[N-(4-Hydroxybutyl)-N-cyclohexylmethylaminocarbonyl]propoxy}-3,4-dihydrocarbostyril.
Colorless needle-like crystals.
Melting point: 109°–111° C.

EXAMPLE 58

6-{4-[N-(5-Propionyloxypentyl)-N-cyclohexylmethylaminocarbonyl]butoxy}-3,4-dihydrocarbostyril.
Colorless needle-like crystals.
Melting point: 60°–62° C.

EXAMPLE 59

6-{4-[N-(2-Hydroxyethyl)-N-(β-3,4-dimethoxyphenethyl)aminocarbonyl]butoxy}carbostyril.
Colorless needle-like crystals.
Melting point: 78°–81° C.

EXAMPLE 60

6-{4-[N-(3-Acetyloxypropyl)-N-(2-tetrahydropyranylmethyl)aminocarbonyl]butoxy}-3,4-dihydrocarbostyril.
Colorless needle-like crystals.
Melting point: 64.5°–66.5° C.

EXAMPLE 61

6-{4-[N-(2,3-Dihydroxypropyl)-N-cyclohexylmethylaminocarbonyl]butoxy}-3,4-dihydrocarbostyril.
Colorless powdery crystals.
Melting point: 112°–114° C.

EXAMPLE 62

6-{4-[N-(2,3-Dihydroxypropyl)-N-cyclohexylmethylaminocarbonyl]butoxy}carbostyril.
Colorless powdery crystals.
Melting point: 125°–128° C.

EXAMPLE 63

6-{3-[N-(2-Hydroxyethyl)-N-(3-hydroxyhexyl)aminocarbonyl]propoxy}carbostyril.
Colorless powdery crystals.
Melting point: 220°–224° C.

EXAMPLE 64

4-{3-[N-(2-Hydroxyethyl)-N-cyclohexylaminocarbonyl]propoxy}carbostyril.
Colorless needle-like crystals.
Melting point: 176°–178° C.

EXAMPLE 65

4-Methyl-6-{3-[N-(2-hydroxyethyl)-N-cyclohexylaminocarbonyl]propoxy}carbostyril.
Colorless needle-like crystals.
Melting point: 171°–173° C.

EXAMPLE 66

1-Ethyl-6-{4-[N-(4-hydroxybutyl)-N-cyclohexylmethylaminocarbonyl]butoxy}-3,4-dihydrocarbostyril.
Colorless syrupy substance.
Physical properties: IR absorption spectrum: $\nu$ cm$^{-1}$ (neat): 1620, 1670.
Elemental analysis (%): Calculated: C; 73.26, H; 9.56, N; 6.33. Found: C; 73.41, H; 9.38, N; 6.10.

EXAMPLE 67

Into 200 ml of chloroform were added 5.9 g of 1-allyl-6-(3-carboxypropoxy)carbostyril and 3.2 g of DBU. The outside of the reaction vessel containing the above mentioned mixture was ice-cooled and 2.8 g of isobutyl chloroformate was added dropwise to the mixture under stirring condition. After the addition operation the reaction mixture was stirred for 1 hour, then 3.7 g of N-cyclohexylpiperazine was added dropwise to the reaction mixture and the reaction was continued for 5 hours. After the reaction was compleated, the reaction mixture was washed with a 1% NaOH aqueous solution and water, then the organic layer was dried with anhydrous Na$_2$SO$_4$. The drying agent was removed by filtration and the mother liquor was concentrated. The residue thus obtained was treated by a silica-gel column chromatography (solvent used was a mixture of chloroform:methanol=30:1) to obtain elute. 4.2 Grams of 1-allyl-6-[3-(4-cyclohexyl-1-piperazinylcarbonyl)propoxy]carbostyril was obtained from the elute, in the form of a colorless oily substance.
IR absorption spectrum: $\nu$ cm$^{-1}$ (neat): 1645, 1680.
Elementary analysis (%): Calculated: C; 71.04, H; 8.48, N; 9.56. Found: C; 70.95, H; 8.61, N; 9.72.

EXAMPLE 68

Into 200 ml of chloroform were added 5 g of 6-(3-carboxypropoxy)carbostyril and 3.2 g DBU. The outside of the reaction vessel containing the above mentioned mixture was ice-cooled and 2.8 g of isobutyl chloroformate was added dropwise to the mixture under stirring condition. After the addition operation, the reaction mixture was further stirred for 1 hour, then 3.7 g of N-cyclohexylpiperazine was added dropwise at a room temperature, and the reaction was continued for 5 hours. After the reaction was completed, the reaction mixture was washed with 1% NaOH aqueous solution and water, then dried with anhydrous sodium sulfate. The drying agent was removed by filtration and the mother liquor was concentrated. The residue thus obtained was treated by a silica-gel column chromatography (solvent used was a mixture of chloroform:methanol=30:1) to obtain elute. The elute was concentrated and the residue was recrystallized from water-containing methanol to obtain 4 g of 6-[3-(4-cyclohexyl-1-piperazylcarbonyl)propoxy]carbostyril in the form of colorless needle-like crystals. Melting point: 184.5°–186° C.

By a method similar to that described in Example 68, there were obtained compounds in Examples 69–74 as follows.

EXAMPLE 69

6-[3-(4-Phenyl-1-piperazinylcarbonyl)propoxy]carbostyril.
Colorless needle-like crystals.
Melting point: 202.5°–203.5° C.

EXAMPLE 70

6-[3-(4-Phenyl-1-piperazinylcarbonyl)propoxy]-3,4-dihydrocarbostyril.
Colorless needle-like crystals.
Melting point: 182.5°–183.5° C.

EXAMPLE 71

6-[3-(4-Phenyl-1-piperidylcarbonyl)propoxy]carbostyril.
Colorless needle-like crystals.
Melting point: 190°–191° C.

EXAMPLE 72

6-[3-(4-Benzyl-1-piperazinylcarbonyl)propoxy]carbostyril.
Colorless prism-like crystals.
Melting point: 174.5°–175.5° C.

EXAMPLE 73

6-[3-(4-Cyclohexyl-1-piperazinylcarbonyl)propoxy]-3,4-dihydrocarbostyril.
Colorless needle-like crystals.
Melting point: 133°–134° C.

EXAMPLE 74

6-[3-(4-Benzyl-1-piperidylcarbonyl)propoxy]carbostyril.
Colorless needle-like crystals.
Melting point: 145°–146° C.

EXAMPLE 75

Into a mixed solvent of 20 ml of dioxane with 20 ml of methylene chloride were added 2.5 g of 6-(3-carboxy)propoxycarbostyril and 1.3 g of N-(2-hydroxyethyl)cycloexylamine and the outside of the reaction vessel containing said mixture was ice-cooled. Then a solution of 2.1 g of N,N'-dicyclohexylcarbodiimide dissolved in 5 ml of methylene chloride was added dropwise to the mixture in keeping a temperature within the range of 10°–20° C. under stirring condition. After the addition operation, the reaction mixture was stirred for 3.5 hours at the same temperature. The crystals precipitated were removed by filtration and the filtrate was concentrated under reduced pressure to dryness. The residue thus obtained was dissolved in 100 ml of methylene chloride and the organic layer was washed with 5% hydrochloric acid aqueous solution, 5% sodium hydrogencarbonate aqueous solution and water in this order then was dried with anhydrous sodium sulfate. The solvent was removed by distillation and the residue thus obtained was recrystallized from chloroform-petroleum ether to obtain 1.1 g of 6-{3-[N-(2-hydroxyethyl)-N-cyclohexylaminocarbonyl]propoxy}carbostyril in the form of colorless needle-like crystals. Melting point: 165°–166° C.

By a method similar to that described in Example 75, there were obtained compounds in Examples 76–98 as follows:

EXAMPLE 76

6-{3-[N-Ethyl-N-(2-pyridyl)aminocarbonyl]propoxy}carbostyril.
Colorless needle-like crystals.
Melting point: 148°–149° C.

EXAMPLE 77

6-{3-[N-Methyl-N-(3-pyridylmethyl)aminocarbonyl]propoxy}-carbostyril.
Colorless needle-like crystals.
Melting point: 169.5°–171° C.

EXAMPLE 78

6-{3-[N-Methyl-N-(2-furylmethyl)aminocarbonyl]-propoxy}-carbostyril.
Colorless needle-like crystals.
Melting point: 125.5°–127.5° C.

EXAMPLE 79

6-{3-[N-Methyl-N-(2-tetrahydropyranylmethyl)aminocarbonyl]propoxy}carbostyril.
Colorless granular crystals.
Melting point: 150°–151.5° C.

EXAMPLE 80

6-{3-[N-Methyl-N-(2-thienylmethyl)aminocarbonyl]-propoxy}-carbostyril.
Colorless needle-like crystals.
Melting point: 133.5°–135° C.

EXAMPLE 81

5-{3-[N-(2-Hydroxyethyl)-N-cyclohexylaminocarbonyl]propoxy}-3,4-dihydrocarbostyril.
Colorless needle-like crystals.
Melting point: 130°–131.5° C.

EXAMPLE 82

6-{5-[N-Methyl-N-(2-tetrahydropyranylmethyl)aminocarbonyl]pentyloxy}carbostyril.
Colorless needle-like crystals.
Melting point: 81°–83° C.

EXAMPLE 83

6-{3-[N-(2-Hydroxybutyl)-N-cyclohexylaminocarbonyl]propoxy}-3,4-dihydrocarbostyril.
Colorless needle-like crystals.
Melting point: 132°–133° C.

EXAMPLE 84

6-{4-[N-(2-Hydroxypropyl)-N-cyclohexylaminocarbonyl]butoxy}-3,4-dihydrocarbostyril.
Colorless needle-like crystals.
Melting point 120.5°–122.5° C.

EXAMPLE 85

6-{4-[N-(2-Hydroxyethyl)-N-cyclohexylaminocarbonyl]butoxy}-3,4-dihydrocarbostyril.
Colorless powdery crystals.
Melting point 122°–123.5° C.

EXAMPLE 86

6-{4-[N-(2-Hydroxybutyl)-N-cyclohexylaminocarbonyl]butoxy}-3,4-dihydrocarbostyril.
Colorless needle-like crystals.
Melting point: 91°–93° C.

EXAMPLE 87

6-{4-[N-(2,3-Dihydroxypropyl)-N-cyclohexylaminocarbonyl]butoxy}-3,4-dihydrocarbostyril.
Colorless prism-like crystals.
Melting point: 112.5°–113.5° C.

EXAMPLE 88

6-{4-[N-(2-Hydroxybutyl)-N-cyclohexylaminocarbonyl]butoxy}-carbostyril.
Colorless powdery crystals.
Melting point: 127°–128.5° C.

EXAMPLE 89

6-{4-[N-(2,3-Dihydroxypropyl)-N-cyclohexylaminocarbonyl]butoxy}-carbostyril.
Colorless needle-like crystals.
Melting point: 138°–140° C.

EXAMPLE 90

6-{4-[N-(2-Hydroxyethyl)-N-cyclohexylaminocarbonyl]butoxy}-carbostyril.
Colorless powdery crystals.
Melting point: 134°–135° C.

EXAMPLE 91

6-{3-[N-(2-hydroxyethyl)-N-(2-tetrahydropyranylmethyl)aminocarbonyl]propoxy}-carbostyril.
Colorless needle-like crystals.
Melting point: 175.5°–177° C.

EXAMPLE 92

6-{4-[N-(2-Hydroxyethyl)-N-(2-tetrahydropyranylmethyl)aminocarbonyl]butoxy}-3,4-dihydrocarbostyril.
Colorless needle-like crystals.
Melting point: 117°–118.5° C.

EXAMPLE 93

6-{4-[N-(4-Hydroxybutyl)-N-(2-tetrahydropyranylmethyl)aminocarbonyl]butoxy}-3,4-dihydrocarbostyril.
Colorless needle-like crystals.
Melting point: 114°–116° C.

EXAMPLE 94

6-{3-[N-(2-Methoxyethyl)-N-cyclohexylaminocarbonyl]propoxy}-carbostyril.
Colorless needle-like crystals.
Melting point: 142.5°–143.5° C.

EXAMPLE 95

6-{4-[N-(2,3-Dihydroxypropyl)-N-cyclohexylmethylaminocarbonyl]butoxy}-3,4-dihydrocarbostyril.
Colorless powdery crystals.
Melting point: 112°–114° C.

EXAMPLE 96

6-[3-(4-Phenyl-1-piperazinylcarbonyl)propoxy]carbostyril.
Colorless needle-like crystals.
Melting point: 202.5°–203.5° C.

EXAMPLE 97

6-{3-[N-(2-Hydroxyethyl)-N-(3-hydroxycyclohexyl)aminocarbonyl]propoxy}-carbostyril.
Colorless powdery crystals.
Melting point: 220°–224° C.

EXAMPLE 98

6-{4-[N-(2-Hydroxyethyl)-N-cyclohexylmethylaminocarbonyl]butoxy}-3,4-dihydrocarbostyril
Colorless plate-like crystals.
Melting point: 123°–125° C.

EXAMPLE 99

Into 200 ml of methylene chloride was suspended 2.4 g of 6-(3-carboxypropoxy)carbostyril, and 2 ml of pyridine was added to the suspension. Then 1.4 g of thionyl chloride was added dropwise thereinto under stirring condition while the inside of the reaction vessel was kept at a temperature within the range from 0° to 20° C. After the addition operation, the reaction was continued at the same temperature for 1 hour under stirring condition. Then 2 ml of N-(2-hydroxyethyl)cyclohexylamine was added dropwise to the reaction mixture, then the reaction was continued at a room temperature for 4 hours under stirring. The reaction mixture was washed thoroughly with a $K_2CO_3$ aqueous solution, then further washed with water and a diluted hydrochloride acid, then dried with anhydrous sodium sulfate. The solvent was removed by distillation and the residue thus obtained was purified and isolated by a silica-gel column chromatography [the silica-gel used was "Wako C-200" and the solvent used was a mixture of chloroform:methanol=20:1 (V/V)] and was recrystallized from chloroform-petroleum ether. 1.2 Grams of 6-{3-[N-(2-hydroxyethyl)-N-cyclohexylaminocarbonyl]propoxy}carbostyril was obtained as in the form of colorless needle-like crystals. Melting point: 165°–166° C.

By a method similar to that described in Example 99, there were obtained compounds in Examples 100–119 as follows:

EXAMPLE 100

6-{3-[N-Ethyl-N-(2-pyridyl)aminocarbonyl]propoxy}carbostyril.
Colorless needle-like crystals.
Melting point: 148°–149° C.

EXAMPLE 101

6-{3-[N-Methyl-N-(3-pyridylmethyl)aminocarbonyl]propoxy}carbostyril.
Colorless needle-like crystals.
Melting point: 169.5°–171° C.

EXAMPLE 102

6-{3-[N-Methyl-N-(2-tetrahydrofurylmethyl)aminocarbonyl]propoxy}carbostyril.
Colorless needle-like crystals.
Melting point: 123°–125° C.

EXAMPLE 103

6-{3-[N-Methyl-N-(2-thienylmethyl)aminocarbonyl]propoxy}carbostyril.
Colorless needle-like crystals.
Melting point: 133.5°–135° C.

EXAMPLE 104

6-{3-[N-(Methyl-N-(2-furylmethyl)aminocarbonyl]propoxy}carbostyril.
Colorless needle-like crystals.
Melting point: 125.5°–127.5° C.

EXAMPLE 105

6-{3-[N-Methyl-N-(2-tetrahydropyranylmethyl)aminocarbonyl]propoxy}-3,4-dihydrocarbostyril.
Colorless prism-like crystals.
Melting point: 121.5°–123.5° C.

EXAMPLE 106

6-{3-[N-(2-Hydroxybutyl)-N-cyclohexylaminocarbonyl]propoxy}-3,4-dihydrocarbostyril.
Colorless needle-like crystals.
Melting point: 132°–133° C.

EXAMPLE 107

6-{4-[N-(2-Hydroxyethyl)-N-cyclohexylaminocarbonyl]butoxy}-3,4-dihydrocarbostyril.
Colorless powdery crystals.
Melting point: 122°–123.5° C.

EXAMPLE 108

6-{4-[N-(2-Hydroxybutyl)-N-cyclohexylaminocarbonyl]butoxy}-3,4-dihydrocarbostyril.
Colorless needle-like crystals.
Melting point: 91°–93° C.

EXAMPLE 109

6-{4-[N-(2,3-Dihydroxypropyl)-N-cyclohexylaminocarbonyl]butoxy}-3,4-dihydrocarbostyril.
Colorless prism-like crystals.
Melting point: 112.5°–113.5° C.

EXAMPLE 110

6-{4-[N-(2-Hydroxybutyl)-N-cyclohexylaminocarbonyl]butoxy}carbostyril.
Colorless powdery crystals.
Melting point: 127°–128.5° C.

EXAMPLE 111

6-{4-[N-(2-Hydroxyethyl)-N-cyclohexylaminocarbonyl]butoxy}carbostyril.
Colorless granular crystals.
Melting point: 134°–135° C.

EXAMPLE 112

6-{3-[N-(2-Hydroxyethyl)-N-(2-tetrahydropyranylmethyl)aminocarbonyl]propoxy}carbostyril.
Colorless needle-like crystals.
Melting point: 175.5°–177° C.

EXAMPLE 113

6-{4-[N-(2-Hydroxyethyl)-N-(2-tetrahydropyranylmethyl)aminocarbonyl]butoxy}-3,4-dihydrocarbostyril.
Colorless needle-like crystals.
Melting point: 117°–118.5° C.

EXAMPLE 114

6-{4-[N-(4-Hydroxybutyl)-N-(2-tetrahydropyranylmethyl)aminocarbonyl]butoxy}-3,4-dihydroxycarbostyril.
Colorless needle-like crystals.
Melting point: 114°–116° C.

EXAMPLE 115

6-{3-[N-(2-Methoxyethyl)-N-cyclohexylaminocarbonyl]propoxy}carbostyril.
Colorless granular crystals.
Melting point: 142.5°–143.5° C.

EXAMPLE 116

6-{4-[N-(2,3-Dihydroxypropyl)-N-cyclohexylmethylaminocarbonyl]butoxy}-3,4-dihydrocarbostyril.
Colorless powdery crystals.
Melting point: 112°–114° C.

EXAMPLE 117

6-[3-(4-Phenyl-1-piperazinylcarbonyl)propoxy]carbostyril.
Colorless needle-like crystals.
Melting point: 202.5°–203.5° C.

EXAMPLE 118

6-{3-[N-(2-Hydroxyethyl)-N-(3-hydroxycyclohexyl)aminocarbonyl]propoxy}carbostyril.
Colorless powdery crystals.
Melting point: 220°–224° C.

EXAMPLE 119

6-{4-[N-(2-Hydroxyethyl)-N-cyclohexylmethylaminocarbonyl]butoxy}-3,4-dihydrocarbostyril.
Colorless plate-like crystals.
Melting point: 123°–125° C.

EXAMPLE 120

3.8 Grams of 6-[3-(p-nitrophenoxycarbonyl)propoxy]carbostyril was dissolved in 40 ml of dimethylformamide, then 1.6 ml of N-(2-hydroxyethyl)cyclohexylamine was added thereto and the reaction mixture was stirred at 60°–70° C. for 12 hours. After the reaction was completed, the solvent was removed by distillation and the residue thus obtained was purified by a silica-gel column chromatography [Silica-gel used was "Wako C-200" and the solvent used was a mixture of chloroform:methanol=20:1 (vol/vol)]. The crude crystals thus obtained was recrystallized from chloroform-petroleum ether to obtain 1.3 g of 6-{3-[N-(2-hydroxyethyl)-N-cyclohexylaminocarbonyl]propoxy}carbostyril as in the form of colorless needle-like crystals. Melting point: 165°–166° C.

By a method similar to that described in Example 120, there were obtained compounds in Examples 121–134 as follows.

EXAMPLE 121

6-{3-[N-Ethyl-N-(2-pyridyl)aminocarbonyl]propoxy}carbostyril.
Colorless needle-like crystals.
Melting point: 148°–149° C.

EXAMPLE 122

6-{3-[N-Methyl-N-(2-tetrahydropyranylmethyl)aminocarbonyl]propoxy}carbostyril.
Colorless granular crystals.
Melting point: 150°–151.5° C.

EXAMPLE 123

6-{4-[N-(2,3-Dihydroxypropyl)-N-cyclohexylaminocarbonyl]butoxy}-3,4-dihydrocarbostyril.
Colorless prism-like crystals.
Melting point: 112.5°–113.5° C.

EXAMPLE 124

6-{4-[N-(2-Hydroxybutyl)-N-cyclohexylaminocarbonyl]butoxy}carbostryil.
Colorless powdery crystals.
Melting point: 127°–128.5° C.

EXAMPLE 125

6-{4-[N-(2-Hydroxyethyl)-N-cyclohexylaminocarbonyl]butoxy}carbostyril.
Colorless granular crystals.
Melting point: 134°–135° C.

EXAMPLE 126

6-{3-[N-(2-Hydroxybutyl)-N-cyclohexylaminocarbonyl]propoxy}-3,4-dihydrocarbostyril.
Colorless needle-like crystals.
Melting point: 132°–133° C.

EXAMPLE 127

6-{4-[N-(2-Hydroxyethyl)-N-cyclohexylaminocarbonyl]butoxy}-3,4-dihydrocarbostyril.
Colorless powdery crystals.
Melting point: 122°–123.5° C.

EXAMPLE 128

6-{4-[N-(2-Hydroxybutyl)-N-cyclohexylaminocarbonyl]butoxy}-3,4-dihydrocarbostyril.
Colorless needle-like crystals.
Melting point: 91°–93° C.

EXAMPLE 129

6-[3-(4-Phenyl-1-piperazinylcarbonyl)propoxy]carbostyril.
Colorless needle-like crystals.
Melting point: 202.5°–203.5° C.

EXAMPLE 130

6-{4-[N-(2-Hydroxyethyl)-N-cyclohexylmethylaminocarbonyl]butoxy}-3,4-dihydrocarbostyril.
Colorless plate-like crystals.
Melting point: 123°–125° C.

EXAMPLE 131

6-{3-[N-(2-Hydroxyethyl)-N-(2-tetrahydropyranylmethyl)aminocarbonyl]propoxy}carbostyril.
Colorless needle-like crystals.
Melting point: 175.5°–177° C.

EXAMPLE 132

6-{4-[N-(2-Hydroxyethyl)-N-(2-tetrahydropyranylmethyl)aminocarbonyl]butoxy}-3,4-dihydrocarbostyril.
Colorless needle-like crystals.
Melting point: 117°–118.5° C.

EXAMPLE 133

6-{4-[N-(4-Hydroxybutyl)-N-(2-tetrahydropyranylmethyl)aminocarbonyl]butoxy}-3,4-dihydrocarbostyril.
Colorless needle-like crystals.
Melting point: 114°–116° C.

EXAMPLE 134

6-{3-[N-(2-Methoxyethyl)-N-cyclohexylaminocarbonyl]propoxy}carbostyril.
Colorless granular crystals.
Melting point: 142.5°–143.5° C.

EXAMPLE 135

Into 100 ml of ethanol were added 2.7 g of 6-(3-ethoxycarbonylpropoxy)carbostyril, 0.5 g of sodium ethylate and 5 ml of N-(2-hydroxyethyl)cyclohexylamine and reacted in an autoclave under a pressure of 110 atomospher at 140°–150° C. for 6 hours. After the reaction was completed, the reaction mixture was cooled and was concentrated under a reduced pressure. The residue thus obtained was dissolved in 200 ml of chloroform and washed with 1% $K_2CO_3$ aqueous solution, a diluted hydrochloric acid and water in this order, then dried with anhydrous sodium sulfate. Then the solvent was removed by distillation and the residue thus obtained was purified by a silica-gel column chromatography [the silica-gel used as Wako C-200, and the solvent used was a mixture of chloroform:methanol=20:1 (V/V)]. The crude crystals thus obtained was recrystallized from chloroform-petroleum ether to obtain 0.9 g of 6-{3-[N-(2-hydroxyethyl)-N-cyclohexylaminocarbonyl]propoxy}carbostyril as in the form colorless needle-like crystals. Melting point: 165°–166° C.

By a method similar to that described in Example 135 there were obtained compounds in Examples 136–143 as follows.

EXAMPLE 136

6-{3-[N-Methyl-N-(3-pyridylmethyl)aminocarbonyl]propoxy}carbostyril.
Colorless needle-like crystals.
Melting point: 169.5°–171° C.

EXAMPLE 137

6-{3-[N-(2-Hydroxybutyl)-N-cyclohexylaminocarbonyl]propoxy}-3,4-dihydrocarbostyril.
Colorless needle-like crystals.
Melting point: 132°–133° C.

EXAMPLE 138

6-{4-[N-(2-Hydroxyethyl)-N-cyclohexylaminocarbonyl]butoxy}-3,4-dihydrocarbostyril.
Colorless powdery crystals.
Melting point: 122°–123.5° C.

EXAMPLE 139

6-{4-[N-(2-Hydroxybutyl)-N-cyclohexylaminocarbonyl]butoxy}-3,4-dihydrocarbostyril.
Colorless needle-like crystals.
Melting point: 91°–93° C.

EXAMPLE 140

6-{4-[N-(2-Hydroxybutyl)-N-cyclohexylaminocarbonyl]butoxy}carbostyril.
Colorless powdery crystals.
Melting point: 127°–128.5° C.

EXAMPLE 141

6-{4-[N-(2-Hydroxyethyl)-N-cyclohexylaminocarbonyl]butoxy}carbostyril.
Colorless granular crystals.
Melting point: 134°–135° C.

EXAMPLE 142

6-{4-[N-(2-Hydroxyethyl)-N-(2-tetrahydropyranylmethyl)aminocarbonyl]butoxy}-3,4-dihydrocarbostyril.
Colorless needle-like crystals.
Melting point: 117°–118.5° C.

EXAMPLE 143

6-[3-(4-Phenyl-1-piperazinylcarbonyl)propoxy]-carbostyril.
Colorless needle-like crystals.
Melting point: 202.5°–203.5° C.

EXAMPLE 144

Into 100 ml of chloroform were added 3.7 g of 6-{3-[N-(2-hydroxyethyl)-N-cyclohexylaminocarbonyl]propoxy}carbostyril and 1.8 ml of triethylamine and the outside of the reaction vessel containing said mixture was ice-cooled. Then 1.4 ml of benzoyl chloride was added dropwise to the mixture under stirring condition. After the addition operation the reaction mixture was further stirred at room temperature for 1 hour. Then the reaction mixture was washed with 5% $NaHCO_3$ aqueous solution, diluted hydrochloric acid and water in this order, then dried with anhydrous sodium sulfate. The drying agent was removed by filtration and the mother liquor is concentrated. The residue thus obtained is treated by a silica-gel column chromatography [the solvent used was a mixture of chloroform:methanol 30:1 (v/v)] and the elute was recrystallized from chloroform-petroleum ether to obtain 3.0 g of 6-{3-[N-(2-benzoyloxyethyl)-N-cyclohexylaminocarbonyl]propoxy}-carbostyril as in the form of colorless needle-like crystals. Melting point: 94°–96° C.

By a method similar to that described in Example 144, there were obtained compounds in Examples 145–146.

EXAMPLE 145

6-{4-[N-(5-Propionyloxypentyl)-N-cyclohexylmethylaminocarbonyl]butoxy}-3,4-dihydrocarbostril.
Colorless needle-like crystals.
Melting point: 60°–62° C.

EXAMPLE 146

6-{4-[N-(3-Acetyloxypropyl)-N-(2-tetrahydropyranylmethyl)aminocarbonyl]butoxy}-3,4-dihydrocarbostyril.
Colorless needle-like crystals.
Melting point: 64.5°–66.5° C.

EXAMPLE 147

Into 50 ml of dimethylformamide were added 1.73 g of 6-hydroxycarbostyril, 1.8 g of $K_2CO_3$ and 0.5 g of KI. The mixture was heating at 60°–70° C. under stirring, then 3.2 g of N-(2-hydroxyethyl)-N-(4-chlorobutyryl)cyclohexylamine was added dropwise gradually thereto. After the addition operation, the reaction mixture was further stirred at the same temperature for 4 hours. Then the solvent was removed by distillation and the residue thus obtained was dissolved in 200 ml of chloroform and the chloroform layer was washed with a diluted hydrochloric acid, 1% Na OH aqueous solution and water in this order, then dried with anhydrous sodium sulfate. The drying agent was removed by filtration, and the mother liquid was concentrated, then the residue thus obtained was crystallized with petroleum ether. The crystals thus obtained was recrystallized from chloroform-petroleum ether to obtain 0.5 g of 6-{3-[N-(2-hydroxyethyl)-N-cyclohexylaminocarbonyl]propoxy}carbostyril. Melting point: 165°–166° C.

By a method similar to that described in Example 147, there were obtained compounds in Examples 148–185 as follows.

EXAMPLE 148

6-{3-[N-(2-Hydroxyethyl)-N-cyclohexylaminocarbonyl]propoxy}-3,4-dihydrocarbostyril.
Colorless needle-like crystals.
Melting point: 139°–141.5° C.

EXAMPLE 149

6-{3-[N-Methyl-N-(3-pyridylmethyl)aminocarbonyl]propoxy}carbostyril.
Colorless needle-like crystals.
Melting point: 169.5°–171° C.

EXAMPLE 150

6-{3-[N-Ethyl-N-(3-pyridyl)aminocarbonyl]propoxy}carbostyril.
Colorless needle-like crystals.
Melting point: 148°–149° C.

EXAMPLE 151

6-{3-[N-Methyl-N-(2-tetrahydropyranylmethyl)aminocarbonyl]propoxy}-3,4-dihydrocarbostyril.
Colorless prism-like crystals.
Melting point: 121.5°–123.5° C.

EXAMPLE 152

6-{3-[N-Ethyl-N-(2-pyridyl)aminocarbonyl]propoxy}carbostyril.
Colorless needle-like crystals.
Melting point: 123°–125° C.

EXAMPLE 153

6-{3-[N-Methyl-N-(2-thienylmethyl)aminocarbonyl]propoxy}carbostyril.
Colorless needle-like crystals.
Melting point: 133.5°–135° C.

EXAMPLE 154

6-{3-[N-Methyl-N-(2-3,4-dihydro-2H-pyranylmethyl)aminocarbonyl]propoxy}carbostyril.
Colorless needle-like crystals.
Melting point: 133.5°–135° C.

EXAMPLE 155

6-{3-[N-Methyl-N-(2-tetrahydropyranylmethyl)aminocarbonyl]propoxy}carbostyril.
Colorless granular crystals.
Melting point: 150°–151.5° C.

EXAMPLE 156

6-{3-[N-Ethyl-N-(3-pyridylmethyl)aminocarbonyl]propoxy}carbostyril.
Colorless needle-like crystals.
Melting point: 145°–147° C.

EXAMPLE 157

6-{3-[N-Methyl-N-(2-furylmethyl)aminocarbonyl]propoxy}carbostyril.
Colorless needle-like crystals.
Melting point: 125.5°–127.5° C.

EXAMPLE 158

6-{3-[N-Methyl-N-(2-tetrahydrofurylmethyl)aminocarbonyl]propoxy}carbostyril.
Colorless needle-like crystals.
Melting point: 123°–125° C.

EXAMPLE 159

5-{3-[N-(2-Hydroxyethyl)-N-cyclohexylaminocarbonyl]propoxy}-3,4-dihydrocarbostyril.
Colorless needle-like crystals.
Melting point: 130°–131.5° C.

EXAMPLE 160

6-[N-Ethyl-N-(3-pyridylmethyl)aminocarbonylmethoxy]-3,4-dihydrocarbostyril.
Colorless needle-like crystals.
Melting point: 82°–84° C.

EXAMPLE 161

6-{5-[N-Methyl-N-(2-tetrahydropyranylmethyl)aminocarbonyl]pentyloxy}carbostyril.
Colorless needle-like crystals.
Melting point: 81°–83° C.

EXAMPLE 162

8-{3-[N-Methyl-N-(2-tetrahydropyranylmethyl)aminocarbonyl]propoxy}carbostyril.
Colorless needle-like crystals.
Melting point: 115.5°–117° C.

EXAMPLE 163

6-{3-[N-(2-Hydroxybutyl)-N-cyclohexylaminocarbonyl]propoxy}-3,4-dihydrocarbostyril.
Colorless needle-like crystals.
Melting point: 132°–133° C.

EXAMPLE 164

6-{3-[N-(2-Hydroxyethyl)-N-cyclooctylaminocarbonyl]propoxy}-3,4-dihydrocarbostyril.
Colorless powdery crystals.
Melting point: 104°–107° C.

EXAMPLE 165

6-{3-[N-(2-Hydroxypropyl)-N-cyclohexylaminocarbonyl]propoxy}carbostyril.
Colorless needle-like crystals.
Melting point: 201°–203° C.

EXAMPLE 166

6-{3-[N-(4-Hydroxybutyl)-N-cyclohexylaminocarbonyl]propoxy}carbostyril.
Colorless powdery crystals.
Melting point: 153°–155° C.

EXAMPLE 167

6-{4-[N-(2-Hydroxypropyl)-N-cyclohexylaminocarbonyl]butoxy}-3,4-dihydrocarbostyril.
Colorless needle-like crystals.
Melting point: 120.5°–122.5° C.

EXAMPLE 168

6-{4-[N-(2-Hydroxyethyl)-N-cyclohexylaminocarbonyl]butoxy}-3,4-dihydrocarbostyril.
Colorless powdery crystals.
Melting point: 122°–123.5° C.

EXAMPLE 169

6-{4-[N-(2-Hydroxybutyl)-N-cyclohexylaminocarbonyl]butoxy}-3,4-dihydrocarbostyril.
Colorless needle-like crystals.
Melting point: 91°–93° C.

EXAMPLE 170

6-{4-[N-(2,3-Dihydroxypropyl)-N-cyclohexylaminocarbonyl]butoxy}-3,4-dihydrocarbostyril.
Colorless prism-like crystals.
Melting point: 112.5°–113.5° C.

EXAMPLE 171

6-{4-[N-(2-Hydroxybutyl)-N-cyclopentylaminocarbonyl]butoxy}-3,4-dihydrocarbostyril.
Colorless needle-like crystals.
Melting point: 102°–103° C.

EXAMPLE 172

6-{4-[N-(2-Hydroxybutyl)-N-cyclohexylaminocarbonyl]butoxy}carbostyril.
Colorless powdery crystals.
Melting point: 127°–128.5° C.

EXAMPLE 173

6-{-[N-(2,3-Dihydroxypropyl)-N-cyclohexylaminocarbonyl]butoxy}carbostyril.
Colorless needle-like crystals.
Melting point: 138°–140° C.

EXAMPLE 174

6-{4-[N-(2-Hydroxybutyl)-N-cyclooctylaminocarbonyl]butoxy}carbostyril.
Colorless powdery crystals.
Melting point: 86°–89° C.

EXAMPLE 175

6-{5-[N-(2-Hydroxybutyl)-N-cyclohexylaminocarbonyl]pentyloxy}-3,4-dihydrocarbostyril.
Colorless powdery crystals.
Melting point: 98°–100° C.

EXAMPLE 176

7-{3-[N-3-Hydroxypropyl)-N-cyclohexylaminocarbonyl]propoxy}-3,4-dihydrocarbostyril.
Colorless powdery crystals.
Melting point: 140°–142° C.

EXAMPLE 177

6-{4-[N-(2-Hydroxyethyl)-N-cyclohexylaminocarbonyl]butoxy}carbostyril.
Colorless granular crystals.
Melting point: 134°–135° C.

EXAMPLE 178

6-{4-[N-Ethyl-N-(2-tetrahydropyranylmethyl)aminocarbonyl]butoxy}-3,4-dihydrocarbostyril.
Colorless needle-like crystals.
Melting point: 87°–88.5° C.

EXAMPLE 179

6-{4-[N-Propyl-N-(2-tetrahydropyranylmethyl)aminocarbonyl]butoxy}-3,4-dihydrocarbostyril.
Colorless needle-like crystals.
Melting point: 77°–79.5° C.

EXAMPLE 180

6-{4-[N-Butyl-N-(2-tetrahydropyranylmethyl)aminocarbonyl]butoxy}-3,4-dihydrocarbostyril.
Colorless needle-like crystals.
Melting point: 93.5°–95.5° C.

EXAMPLE 181

6-{3-[N-(2-Hydroxyethyl)-N-(2-tetrahydropyranylmethyl)aminocarbonyl]propoxy}carbostyril.
Colorless needle-like crystals.
Melting point: 175.5°–177° C.

EXAMPLE 182

6-{4-[N-(2-Hydroxyethyl)-N-(3-pyridylmethyl)aminocarbonyl]butoxy}-3,4-dihydrocarbostyril.
Colorless needle-like crystals.
Melting point: 80°–82.5° C.

EXAMPLE 183

6-{4-[N-(2-Hydroxyethyl)-N-(2-tetrahydropyranylmethyl)aminocarbonyl]butoxy}-3,4-dihydrocarbostyril.
Colorless needle-like crystals.
Melting point: 117°–118.5° C.

EXAMPLE 184

6-{4-[N-(3-Hydroxypropyl)-N-(2-tetrahydropyranylmethyl)aminocarbonyl]butoxy}-3,4-dihydrocarbostyril.
Colorless needle-like crystals.
Melting point: 98.5°–100° C.

EXAMPLE 185

6-{4-[N-(4-Hydroxybutyl)-N-(2-tetrahydropyranylmethyl)aminocarbonyl]butoxy}-3,4-dihydrocarbostyril.
Colorless needle-like crystals.
Melting point: 114°–116° C.

EXAMPLE 186

Into 50 ml of dimethylformamide were added 1.9 g of 1-benzyl-6-hydroxy-3,4-dihydrocarbostyril, 1.8 g of $K_2CO_3$ and 0.5 g of KI. The mixture was heated at 60°–70° C. under stirring, then 3.4 g of N-ethyl-N-(2-tetrahydropyranylmethyl)-5-chloropentanic acid amide was added dropwise gradually thereto. After the addition operation, the reaction mixture was further stirred at the same temperature for 4 hours. Then the solvent was removed by distillation and the residue thus obtained was dissolved in 200 ml of chloroform and the chloroform layer was washed with a diluted hydrochloric acid, 1% NaOH aqueous solution and water in this order, then dried with anhydrous sodium sulfate. The drying agent was removed by filtratoon, and the mother liquor was concentrated, then the residue thus obtained was treated by a silica-gel column chromatography [solvent used was a mixture of chloroform:methanol=20:1 (v/v)]. 0.6 Grams of 1-benzyl-6-{4-[N-(2-tetrahydropyranylmethyl)-N-ethylaminocarbonyl]butoxy}-3,4-dihydrocarbostyril was obtained as in the form of a colorless syrupy substance.

IR absorption spectrum: $\nu$ cm$^{-1}$ (neat): 1620, 1690.
Elemental analysis: Calculated: C; 75.29, H; 8.23, N; 6.06. Found: C; 75.41, H; 8.33, N; 6.21.

EXAMPLE 187

Into 50 ml of dimethylformamide were added 1.6 g of 6-hydroxy-3,4-dihydrocarbostyril, 1.4 g of $K_2CO_3$ and 0.5 g of KI. The mixture was heated at 60°–70° C. under stirring, then 3.6 g of N-(3-hydroxypropyl)-N-(5- chlorovaleryl)-N-cyclohexylemethylamine was added dropwise gradually thereto. After the addition operation, the reaction mixture was further stirred at the same temperature for 5 hours. The solvent was removed by distillation and the residue thus obtained was extrated with 100 ml of chloroform and the chloroform layer was washed with 1% NaOH aqueous solution, a diluted hydrochloric acid and water in this order, then dried with sodium sulfate. The drying agent was removed by filtration and the mother liquor was concentrated, then the residue thus obtained was treated by a silica-gel column chromatography [the solvent used was a mixture of chloroform:methanol=40:1 (vol/vol)]. The elute was concentreated and the residue thus obtained was recrystallized from ethyl acetate-petroleum ether to obtain 1.1 g of 6-{4-[N-cyclohexylmethyl-N-(3-hydroxypropyl)aminocarbonyl]butoxy}-3,4-dihydrocarbostyril as in the form of colorless needle-like crystals. Melting point: 95°-97° C.

By a method similar to that described in Example 187, there were obtained compounds in Examples 188–208 as follows:

EXAMPLE 188

6-[N-(2-Hydroxyethyl)-N-phenylaminocarbonylmethoxy]carbostyril.
Colorless powdery crystals.
Melting point: 162°-165° C.

EXAMPLE 189

6-{3-[N-(2-Methoxyethyl)-N-cyclohexylaminocarbonyl]propoxy}carbostyril.
Colorless needle-like crystals.
Melting point: 142.5°-143.5° C.

EXAMPLE 190

6-{3-[N-(2-Hydroxyl-1-methylpropyl)-N-cyclohexylmethylaminocarbonyl]propoxy}-carbostyril.
Colorless needle-like crystals.
Melting point: 179.5°-181.5° C.

EXAMPLE 191

6-{3-[N-(2-Hydroxyethyl)-N-butylaminocarbonyl]propoxy}-carbostyril.
Colorless needle-like crystals.
Melting point: 153°-154° C.

EXAMPLE 192

6-{3-[N-Di-(2-hydroxyethyl)aminocarbonyl]propoxy}-carbostyril.
Colorless needle-like crystals.
Melting point: 122°-123.5° C.

EXAMPLE 193

6-{4-[N-2-Hydroxyethyl)-N-phenylaminocarbonyl]-butoxy}-3,4-dihydrocarbostyril.
Colorless needle-like crystals.
Melting point: 113°-116° C.

EXAMPLE 194

6-{4-[N-(2-Hydroxyethyl)-N-benzylaminocarbonyl]-butoxy}-3,4-dihydrocarbostyril.
Colorless powdery crystals.
Melting point: 91.5°-93° C.

EXAMPLE 195

6-{4-[N-(2-Hydroxyethyl)-N-cyclohexylmethylaminocarbonyl]-butoxy}-3,4-dihydrocarbosyril.
Colorless plate-like crystals.
Melting point: 123°-125° C.

EXAMPLE 196

6-{4-[N-(4-Hydroxybutyl)-N-cyclohexylmethylaminocarbonyl]butoxy}-3,4-dihydrocarbostyril.
Colorless needle-like crystals.
Melting point: 119°-120.5° C.

EXAMPLE 197

6-{4-[N-(2-Hydroxybutyl)-N-cyclohexylaminocarbonyl]butoxy}-3,4-dihydrocarbostyril.
Colorless needle-like crystals.
Melting point: 123°-125° C.

EXAMPLE 198

6-{4-[N-(5-Hydroxypentyl)-N-cyclohexymethylaminocarbonyl]butoxy}-3,4-dihydrocarbostyril.
Colorless needle-like crystals.
Melting point: 113.5°-115° C.

EXAMPLE 199

6-{3-[N-(4-Hydroxybutyl)-N-cyclohexylmethylaminocarbonyl]propoxy}-3,4-dihydrocarbostyril.
Colorless needle-like crystals.
Melting point: 109°-111° C.

EXAMPLE 200

6-{4-[N-(5-Propionyloxypentyl)-N-cyclohexylmethylaminocarbonyl]butoxy}-3,4-dihydrocarbostyril.
Colorless needle-like crystals.
Melting point: 60°-62° C.

EXAMPLE 201

6-{4-[N-(2-Hydroxyethyl)-N-(β-3,4-dimethoxyphenethyl)aminocarbonyl]butoxy}carbostyril.
Colorless needle-like crystals.
Melting point: 78°-81° C.

EXAMPLE 202

6-{4-[N-(3-Acetyloxypropyl)-N-(2-tetrahydropyranylmethyl)aminocarbonyl]butoxy}-3,4-dihydrocarbostyril.
Colorless needle-like crystals.
Melting point: 64.5°-66.5° C.

EXAMPLE 203

6-{4-[N-(2,3-Dihydroxyporpyl)-N-cyclohexylmethylaminocarbonyl]butoxy}-3,4-dihydrocarbostyril.
Colorless powdery crystals.
Melting point: 112°-114° C.

EXAMPLE 204

6-{4-[N-(2,3-Dihydroxypropyl)-N-cyclohexylmethylaminocarbonyl]butoxy}carbostyril.
Colorless powdery crystals.
Melting point: 125°-128° C.

EXAMPLE 205

6-{3-[N-(2-Hydroxyethyl)-N-(3-hydroxycyclohexyl)aminocarbonyl]propoxy}carbostyril.
Colorless powdery crystals.
Melting point: 220°-224° C.

EXAMPLE 206

4-{3-[N-(2-Hydroxyethyl)-N-cyclohexylaminocarbonyl]propoxy}carbostyril.
Colorless needle-like crystals.

Melting point: 176°–178° C.

EXAMPLE 207

4-Methyl-6-{5 3-[N-(2-hydroxyethyl)-N-cyclohexylaminocarbonyl]propoxy}carbostyril.
Colorless needle-like crystals.
Melting point: 171°–173° C.

EXAMPLE 208

1-Ethyl-6-{4-[N-(4-hydroxybutyl)-N-cyclohexylmethylaminocarbonyl]butoxy}-3,4-dihydrocarbostyril.
Colorless syrupy substance.
Melting point:
IR absorption spectrum: $\nu\,cm^{-1}$ (neat) 1620, 1670.
Elemental analysis (%): Calculated: C; 73.26, H; 9.56, N; 6.33. Found: C; 73.42, H; 9.41, N; 6.21.

EXAMPLE 209

Into 100 ml isopropanol were added 2.0 g of 1-allyl-6-hydroxy-3,4-dihydrocarbostyril and 1.8 ml of DBU. The mixture was refluxed under stirring and 4.2 g of 4-cyclohexyl-1-γ-bromobutylpiperazine was added thereto. After the addition operation, the reaction mixture was further refluxed under stirring for 8 hours, then concentrated. The residue thus obtained was extracted with chloroform and the chloroform layer was washed with 1N-NaOH aqueous solution and water, then dried with anhydrous sodium sulfate. The drying agent was removed by filtration and the mother liquor was concentrated. The residue thus obtained was treated by a silica-gel column chromatography [the solvent used was a mixture of chloroform:methanol=20:1 (vol/vol)]. 3.5 Grams of 1-allyl-6-[3-(4-cyclohexyl-1-piperazinylcarbonyl)propoxy]-3,4-dihydrocarbostyril was obtained as in the form of a colorless syrupy substance.
IR absorption spectrum: $\nu\,cm^{-1}$ (neat): 1645, 1680.
Elemental analysis (%): Calculated: C; 71.04, H; 8.84, N: 9.56. Found: C; 70.95, H, 8.61, N; 9.72.

EXAMPLE 210

Into 100 ml of isopropanol were added 1.6 g of 6-hydroxy-3,4-dihydrocarbostyril and 1.8 ml of DBU. The mixture was refluxed under stirring and 4.2 g of 4-cyclohexyl-1-γ-bromobutylpiperazine was added thereto. After the addition operation, the reaction mixture was further refluxed under stirring for 8 hours, then concentrated. The residue thus obtained was extracted with chloroform and the chloroform layer was washed with 1N-NaOH aqueous solution and water, then dried with anhydrous sodium sulfate. The drying agent was removed by filtration and the mother liquor was concentrated. The residue thus obtained was treated by a silica-gel column chromatography [the solvent used was a mixture of chloroform:methanol=20:1 (vol/vol)]. 2.8 Grams of 6-[3-(4-cyclohexyl-1-piperazinylcarbonyl)propoxy]-3,4-dihydrocarbostyril was obtained as in the form of colorless needle-like substance. Melting point: 133°–134° C.

By a method similar to that described in Example 210, there are obtained compounds in Examples 211–216 as follows:

EXAMPLE 211

6-[3-(4-Phenyl-1-piperazinylcarbonyl)propoxy]carbostyril.
Colorless needle-like crystals.
Melting point: 202.5°–203.5° C.

EXAMPLE 212

6-[3-(4-Phenyl-1-piperazinylcarbonyl)propoxy]-3,4-dihydrocarbostyril.
Colorless needle-like crystals.
Melting point: 182.5°–183.5° C.

EXAMPLE 213

6-[3-(4-Phenyl-1-piperidylcarbonyl)propoxy]carbostyril.
Colorless needle-like crystals.
Melting point: 190°–191° C.

EXAMPLE 214

6-[3-(4-Benzyl-1-piperazinylcarbonyl)propoxy]carbostyril.
Colorless prism-like crystals.
Melting point: 174.5°–175.5° C.

EXAMPLE 215

6-[3-(4-Cyclohexyl-1-piperazinylcarbonyl)propoxy]carbostyril.
Colorless needle-like crystals.
Melting point: 184.5°–186.0° C.

EXAMPLE 216

6-[3-(4-Benzyl-1-piperidylcarbonyl)propoxy]carbostyril.
Colorless needle-like crystals.
Melting point: 145°–146° C.

EXAMPLE 217

1.0 Gram of 6-{3-[N-(2-hydroxyethyl)-N-cyclohexylaminocarbonyl]-2-propenyloxy}carbostyril was dissolved in 50 ml of methanol and 0.1 g of 5% palladium-carbon was added. The mixture was catalytically hydrogenated at a room temperature under an atmospheric pressure for 5 hours. After the reaction was completed, the catalyst was removed by filtration and the filtrate was concentrated by distillation under a reduced pressure to dryness. The residue thus obtained was recrystallized from chloroform-petroleum ether. 0.8 Gram of 6-{3-[N-(2-hydroxyethyl)-N-cyclohexylaminocarbonyl]propoxy}carbostyril was obtained as in the form of colorless needle-like crystals. Melting point: 165°–166° C.

By a method similar to that described in Example 217, there were obtained compounds in Examples 218–253 as follows.

EXAMPLE 218

6-{3-[N-Ethyl-N-(3-pyridyl)aminocarbonyl]-propoxy}carbostyril.
Colorless needle-like crystals.
Melting point: 148°–149° C.

EXAMPLE 219

6-{3-[N-Ethyl-N-(2-pyridyl)aminocarbonyl]-propoxy}carbostyril.
Colorless needle-like crystals.
Melting point: 148°–149° C.

EXAMPLE 220

6-{3-[N-Methyl-N-(3-pyridylmethyl)aminocarbonyl]propoxy}carbostyril.
Colorless needle-like crystals.
Melting point: 169.5°–171° C.

EXAMPLE 221

6-{3-[N-Methyl-N-(2-tetrahydropyranylmethyl)aminocarbonyl]propoxy}carbostyril.
Colorless granular crystals.
Melting point: 150°–151.5° C.

EXAMPLE 222

8-{3-[N-Methyl-N-(2-tetrahydropyranylmethyl)aminocarbonyl]propoxy}carbostyril.
Colorless needle-like crystals.
Melting point: 115.5°–117° C.

EXAMPLE 223

6-{3-[N-Methyl-N-(2-tetrahydropyranylmethyl)aminocarbonyl]propoxy}-3,4-dihydrocarbostyril.
Colorless prism-like crystals.
Melting point: 121.5°–123.5° C.

EXAMPLE 224

5-{3-[N-(2-Hydroxyethyl)-N-cyclohexylaminocarbonyl]propoxy}-3,4-dihydrocarbostyril.
Colorless needle-like crystals.
Melting point: 130°–131.5° C.

EXAMPLE 225

6-[N-Ethyl-N-(3-pyridylmethyl)aminocarbonylmethoxy]-3,4-dihydrocarbostyril.
Colorless needle-like crystals.
Melting point: 82°–84° C.

EXAMPLE 226

6-{5-[N-Methyl-N-(2-tetrahydropyranylmethyl)aminocarbonyl]-pentyloxy}carbostyril.
Colorless needle-like crystals.
Melting point: 81°–83° C.

EXAMPLE 227

6-{3-[N-Ethyl-N-(3-pyridylmethyl)aminocarbonyl]propoxy}carbostyril.
Colorless needle-like crystals.
Melting point: 145°–147° C.

EXAMPLE 228

6-{3-[N-Methyl-N-(2-tetrahydrofurylmethyl)aminocarbonyl]propoxy}carbostyril.
Colorless needle-like crystals.
Melting point: 123°–125° C.

EXAMPLE 229

6-{3-[N-(2-Hydroxyethyl)-N-cyclohexylaminocarbonyl]propoxy}-3,4-dihydrocarbostyril.
Colorless needle-like crystals.
Melting point: 139°–141.5° C.

EXAMPLE 230

5-{3-[N-(2-Hydroxyethyl)-N-cyclohexylaminocarbonyl]propoxy}-3,4-dihydrocarbostyril.
Colorless needle-like crystals.
Melting point: 130°–131.5° C.

EXAMPLE 231

6-{3-[N-(2-Hydroxybutyl)-N-cyclohexylaminocarbonyl]propoxy}-3,4-dihydrocarbostyril.
Colorless needle-like crystals.
Melting point: 132°–133° C.

EXAMPLE 232

6-{3-[N-(2-Hydroxyethyl)-N-cyclooctylaminocarbonyl]propoxy}-3,4-dihydrocarbostyril.
Colorless powdery crystals.
Melting point: 104°–107° C.

EXAMPLE 233

6-{3-[N-(2-Hydroxypropyl)-N-cyclohexylaminocarbonyl]propoxy}carbostyril.
Colorless needle-like crystals.
Melting point: 201°–203° C.

EXAMPLE 234

6-{3-[N-(4-Hydroxybutyl)-N-cyclohexylaminocarbonyl]propoxy}carbostyril.
Colorless powdery crystals.
Melting point: 153°–155° C.

EXAMPLE 235

6-{4-[N-(2-Hydroxypropyl)-N-cyclohexylaminocarbonyl]butoxy}-3,4-dihydrocarbostyril.
Colorless needle-like crystals.
Melting point: 120.5°–122.5° C.

EXAMPLE 236

6-{4-[N-(2-Hydroxyethyl)-N-cyclohexylaminocarbonyl]butoxy}-3,4-dihydrocarbostyril.
Colorless powdery crystals.
Melting point: 122°–123.5° C.

EXAMPLE 237

6-{4-[N-(2-Hydroxybutyl)-N-cyclohexylaminocarbonyl]butoxy}-3,4-dihydrocarbostyril.
Colorless needle-like crystals.
Melting point: 91°–93° C.

EXAMPLE 238

6-{4-[N-(2,3-Dihydroxypropyl)-N-cyclohexylaminocarbonyl]butoxy}-3,4-dihydrocarbostyril.
Colorless prism-like crystals.
Melting point: 112.5°–113.5° C.

EXAMPLE 239

6-{4-[N-(2-Hydroxybutyl)-N-cyclopentylaminocarbonyl]butoxy}-3,4-dihydrocarbostyril.
Colorless needle-like crystals.
Melting point: 102°–103° C.

EXAMPLE 240

6-{4-[N-(2-Hydroxybutyl)-N-cyclohexylaminocarbonyl]butoxy}carbostyril.
Colorless powdery crystals.
Melting point: 127°–128.5° C.

EXAMPLE 241

6-{4-[N-(2,3-Dihydroxypropyl)-N-cyclohexylaminocarbonyl]butoxy}carbostyril.
Colorless needle-like crystals.
Melting point: 138°–140° C.

EXAMPLE 242

6-{4-[N-(2-Hydroxybutyl)-N-cyclooctylaminocarbonyl]butoxy}carbostyril.
Colorless powdery crystals.
Melting point: 86°–89° C.

EXAMPLE 243

6-{5-[N-(2-Hydroxybutyl)-N-cyclohexylaminocarbonyl]pentyloxy}-3,4-dihydrocarbostyril.
Colorless powdery crystals.
Melting point: 98°–100° C.

EXAMPLE 244

7-{3-[N-(3-Hydroxypropyl)-N-cyclohexylaminocarbonyl]propoxy}-3,4-dihydrocarbostyril.
Colorless powdery crystals.
Melting point: 140°–142° C.

EXAMPLE 245

6-{4-[N-(2-Hydroxyethyl)-N-cyclohexylaminocarbonyl]butoxy}carbostyril.
Colorless granular crystals.
Melting point: 134°–135° C.

EXAMPLE 246

6-{4-[N-Ethyl-N-(2-tetrahydropyranylmethyl)aminocarbonyl]butoxy}-3,4-dihydrocarbostyril.
Colorless needle-like crystals.
Melting point: 87°–88.5° C.

EXAMPLE 247

6-{4-[N-Propyl-N-(2-tetrahydropyranylmethyl)aminocarbonyl]butoxy}-3,4-dihydrocarbostyril.
Colorless needle-like crystals.
Melting point: 77°–79.5° C.

EXAMPLE 248

6-{4-[N-Butyl-N-(2-tetrahydropyranylmethyl)aminocarbonyl]butoxy}-3,4-dihydrocarbostyril.
Colorless needle-like crystals.
Melting point: 93.5°–95.5° C.

EXAMPLE 249

6-{3-[N-(2-Hydroxyethyl)-N-(2-tetrahydropyranylmethyl)aminocarbonyl]propoxy}carbostyril.
Colorless needle-like crystals.
Melting point: 175.5°–177° C.

EXAMPLE 250

6-{4-[N-(2-Hydroxyethyl)-N-(pyridylmethyl)aminocarbonyl]butoxy}-3,4-dihydrocarbostyril.
Colorless needle-like crystals.
Melting point: 80°–82.5° C.

EXAMPLE 251

6-{4-[N-(2-Hydroxyethyl)-N-(2-tetrahydropyranylmethyl)aminocarbonyl]butoxy}-3,4-dihydrocarbostyril.
Colorless needle-like crystals.
Melting point: 117°–118.5° C.

EXAMPLE 252

6-{4-[N-(3-Hydroxypropyl)-N-(2-tetrahydropyranylmethyl)aminocarbonyl]butoxy}-3,4-dihydrocarbostyril.
Colorless needle-like crystals.
Melting point: 98.5°–100° C.

EXAMPLE 253

6-{4-[N-(4-Hydroxybutyl)-N-(2-tetrahydropyranylmethyl)aminocarbonyl]butoxy}-3,4-dihydrocarbostyril.
Colorless needle-like crystals.
Melting point: 114°–116° C.

EXAMPLE 254

Into 100 ml of ethanol were added 5 g of 6-{4-[N-(2-hydroxyethyl)-N-cyclohexylmethylaminocarbonyl]-2-butenyloxy}-3,4-dihydrocarbostyril and 1 g of 1% palladium-carbon. The mixture was catalytically hydrogenized under an atmospheric pressure at a room temperature for 5 hours. After the reaction was completed, the catalyst was removed by filtration and the filtrate was concentrated. The residue thus obtained was recrystalized from ethyl acetate-petraleum ether to obtain 4.2 g of 6-{4-[N-(2-hydroxyethyl)-N-cyclohexylmethylaminocarbonyl]butoxy}-3,4-dihydrocarbostyril as in the form of colorless plate-like crystals. Melting point: 123°–125° C.

By a method similar to that described in Example 254, there were obtained compounds in Examples 255–273 as follows:

EXAMPLE 255

6-[N-(2-Hydroxyethyl)-N-phenylaminocarbonylmethyl]carbostyril.
Colorless powdery crystals.
Melting point: 162°–165° C.

EXAMPLE 256

6-{3-[N-(2-Methoxyethyl)-N-cyclohexylaminocarbonyl]propoxy}carbostyril.
Colorless powdery crystals.
Melting point: 142.5°–143.5° C.

EXAMPLE 257

6-{3-[N-(2-Hydroxy-1-methylpropyl)-N-cyclohexylaminomethylcarbonyl]propoxy}carbostyril.
Colorless needle-like crystals.
Melting point: 179.5°–181.5° C.

EXAMPLE 258

6-{3-[N-(2-Hydroxyethyl)-N-butylaminocarbonyl]propoxy}carbostyril.
Colorless needle-like crystals.
Melting point: 153°–154° C.

EXAMPLE 259

6-{3-[N-Di-(2-hydroxyethyl)aminocarbonyl]propoxy}carbostyril.
Colorless needle-like crystals.
Melting point: 122°–123.5° C.

EXAMPLE 260

6-{4-[N-(2-Hydroxyethyl)-N-phenylaminocarbonyl]butoxy}-3,4-dihydrocarbostyril.
Colorless needle-like crystals.
Melting point: 113°–116° C.

EXAMPLE 261

6-{4-[N-(2-Hydroxyethyl)-N-benzylaminocarbonyl]butoxy}-3,4-dihydrocarbostyril.
Colorless powdery crystals.
Melting point: 91.5°–93° C.

EXAMPLE 262

6-{4-[N-(2-Hydroxyethyl)-N-cyclohexylmethylaminocarbonyl]butoxy}-3,4-dihydrocarbostyril.
Colorless plate-like crystals.
Melting point: 123°–125° C.

EXAMPLE 263

6-{4-[N-(4-Hydroxybutyl)-N-cyclohexylmethylaminocarbonyl]butoxy}-3,4-dihydrocarbostyril.
Colorless needle-like crystals.
Melting point: 119°–120.5° C.

EXAMPLE 264

6-{4-[N-(2-Hydroxybutyl)-N-cyclohexylaminocarbonyl]butoxy}-3,4-dihydrocarbostyril.
Colorless needle-like crystals.
Melting point: 123°–125° C.

EXAMPLE 265

6-{4-[N-(2-Methoxyethyl)-N-cyclohexylaminocarbonyl]butoxy}carbostyril.
Colorless needle-like crystals.
Melting point: 107°–109° C.

EXAMPLE 266

6-{5-[N-(2-Hydroxyethyl)-N-benzylaminocarbonyl]pentyloxy}-3,4-dihydrocarbostyril.
Colorless powdery crystals.
Melting point 93.5°–95.5° C.

EXAMPLE 267

6-{3-[N-(2-Benzoyloxyethyl)-N-cyclohexylaminocarbonyl]propoxy}carbostyril.
Colorless needle-like crystals.
Melting point: 94°–97° C.

EXAMPLE 268

6-{4-[N-(3-Acetyloxypropyl)-N-(2-tetrahydropyranylmethyl)aminocarbonyl]butoxy}-3,4-dihydrocarbostyril.
Colorless needle-like crystals.
Melting point: 64.5°–66.5° C.

EXAMPLE 269

6-{4-[N-(2,3-Dihydroxypropyl)-N-cyclohexylmethylaminocarbonyl]butoxy}-3,4-dihydrocarbostyril.
Colorless powdery crystals.
Melting point: 112°–114° C.

EXAMPLE 270

6-{4-[N-(2,3-Dihydroxypropyl)-N-cyclohexylmethylaminocarbonyl]butoxy}carbostyril.
Colorless powdery crystals.
Melting point: 125°–128° C.

EXAMPLE 271

6-{3-[N-(2-Hydroxyethyl)-N-(3-hydroxycyclohexyl)aminocarbonyl]propoxy}carbostyril.
Colorless powdery crystals.
Melting point: 220°–224° C.

EXAMPLE 272

4-{3-[N-(2-Hydroxyethyl)-N-cyclohexylaminocarbonyl]propoxy}carbostyril.
Colorless needle-like crystals.
Melting point: 176°–178° C.

EXAMPLE 273

4-Methyl-6-{3-[N-(2-hydroxyethyl)-N-cyclohexylcarbonyl]propoxy}carbostyril.
Colorless needle-like crystals.
Melting point: 171°–173° C.

EXAMPLE 274

1.0 Gram of 6-[3-(4-phenyl-1-piperazinylcarbonyl)-2-propenyloxy]carbostyril was dissolved in 50 ml of methanol, then 0.1 g of 5% palladium-carbon was added thereto. The mixture was catalytically hydrogenated at a room temperature under an atmospheric pressure for 5 hours. After the reaction was completed, the catalyst was removed by filtration and the filtrate was concentrated by distillation under a reduced pressure to dryness. The residue thus obtained was recrystallized from chloroform-petroleum ether to obtain 0.75 g of 6-[3-(4-phenyl-1-piperazinylcarbonyl)propoxy]carbostyril as in the form of colorless needle-like crystals. Melting point 202.5°–203.5° C.

By a method similar to that described in Example 274, there were obtained compounds in Examples 275–280 as follows.

EXAMPLE 275

6-[3-(4-Cyclohexyl-1-piperazinylcarbonyl)propoxy]carbostyril.
Colorless needle-like crystals.
Melting point: 184.5°–186° C.

EXAMPLE 276

6-[3-(4-Phenyl-1-piperazinylcarbonyl)propoxy]-3,4-dihydrocarbostyril.
Colorless needle-like crystals.
Melting point: 182.5°–183.5° C.

EXAMPLE 277

6-[3-(4-Phenyl-1-piperidylcarbonyl)propoxy]carbostyril.
Colorless needle-like crystals.
Melting point: 190°–191° C.

EXAMPLE 278

6-[3-(4-Benzyl-1-piperazinylcarbonyl)propoxy]carbostyril.
Colorless prism-like crystals.
Melting point: 174.5°–175.5° C.

EXAMPLE 279

6-[3-(4-Cyclohexyl-1-piperazinylcarbonyl)propoxy]-3,4-dihydrocarbostyril.
Colorless needle-like crystals.
Melting point: 133°–134° C.

EXAMPLE 280

6-[3-(4-Benzyl-1-piperidylcarbonyl)propoxy]carbostyril.
Colorless needle-like crystals.
Melting point: 145°–146° C.

What is claimed is:

1. A carbostyril derivative or its salt represented by the general formula (1),

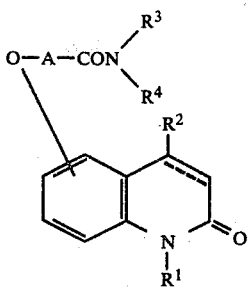

wherein R¹ is a hydrogen atom; R² is a hydrogen atom or a $C_{1-6}$-alkyl group; A is a $C_{1-6}$-alkylene group; R³ is a hydroxy $C_{1-6}$-alkyl group having one to three hydroxy groups as the substituent, a $C_{1-6}$-alkoxy-$C_{1-6}$-alkyl group, a $C_{1-6}$-alkanoyloxy-$C_{1-6}$-alkyl group, or a benzoyloxy-$C_{1-6}$-alkyl group; R⁴ is a $C_{3-10}$-cycloalkyl group which may have 1 to 3 hydroxy groups as the subsitituent in the cycloalkyl ring, or a $C_{3-10}$-cycloalkyl-$C_{1-6}$-alkyl group; further R³, R⁴ and the adjacent nitrogen atom, as well as with another nitrogen atom, may form a group of the formula

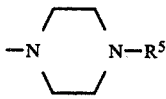

wherein R⁵ is a phenyl group, a $C_{3-10}$-cycloalkyl group or a phenyl-$C_{1-6}$-alkyl group; the carbon-carbon bond between the three and four positions in the carbostyril skeleton is a single or double bond; and the substituted position of the group of the formula

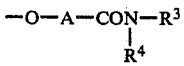

is either the 5- or 6-position in the carbostyril skeleton.

2. The carbostyril derivative according to claim 1 wherein A is a trimethylene or tetramethylene group.

3. The carbostyril derivative according to claim 2, wherein the carbon-carbon bond between the 3- and 4-positions in the carbostyril skeleton is a double bond.

4. The carbostyril derivative according to claim 2, wherein the carbon-carbon bond between the 3- and 4-positions in the carbostyril skeleton is a single bond.

5. The carbostyril derivative according to claim 3 or 30, wherein R³ is a hydroxy-$C_{1-6}$-alkyl group having 1 to 3 hydroxy group(s) as the substituent(s).

6. The carbostyril derivative according to claim 5, wherein R³ is a hydroxy-$C_{1-6}$-alkyl group having one hydroxy group as the substituent.

7. The carbostyril derivative according to claim 3 or 30, wherein R³ is a $C_{1-6}$-alkoxy-$C_{1-6}$-alkyl group.

8. The carbostyril derivative according to claim 3 or 30, wherein R³ is a $C_{1-6}$-alkanoyloxy-$C_{1-6}$-alkyl or a benzoyloxy-$C_{1-6}$-alkyl group.

9. The carbostyril derivative according to claim 6, wherein R² is a hydrogen atom.

10. The carbostyril derivative according to claim 1, wherein R³, R⁴ and the adjacent nitrogen atom, as well as with another nitrogen atom, form a group of the formula,

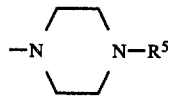

wherein R⁵ is a phenyl group, a $C_{3-10}$-cycloalkyl group or a phenyl-$C_{1-6}$-alkyl group.

11. 6-{3-[N-(2-Hydroxyethyl)-N-cyclohexylaminocarbonyl]propoxy}carbostyril.

12. 6-{3-[N-(2-Hydroxyethyl)-N-cyclohexylaminocarbonyl]propoxy}-3,4-dihydrocarbostyril.

13. 6-{3-[N-(2-Hydroxyethyl)-N-(3-hydroxycyclohexyl)aminocarbonyl]propoxy}carbostyril.

14. 6-{4-[N-(2-Methoxyethyl)-N-cyclohexylaminocarbonyl]butoxy}carbostyril.

15. 6-{4-[N-(2-Hydroxybutyl)-N-cyclohexylmethylaminocarbonyl]butoxy}-3,4-dihydrocarbostyril.

16. 6-{3-[N-(2-Benzoyloxyethyl)-N-cyclohexylaminocarbonyl]propoxy}carbostyril.

17. 6-[3-(4-Phenyl-1-piperazinylcarbonyl)propoxy]carbostyril.

18. 6-[3-(4-Cyclohexyl-1-piperazinylcarbonyl)propoxy]carbostyril.

19. 6-{3-[N-(2-Hydroxybutyl)-N-cyclohexylaminocarbonyl]propoxy}-3,4-dihydrocarbostyril.

20. 6-{4-[N-(2,3-Dihydroxypropyl)-N-cyclohexylaminocarbonyl]butoxy}-3,4-dihydrocarbostyril.

21. 6-[4-{N-(2-Hydroxybutyl)-N-cyclohexylaminocarbonyl}butoxy]-3,4-dihydrocarbostyril.

22. 6-[3-{N-(4-Hydroxybutyl)-N-cyclohexylaminocarbonyl}propoxy]-3,4-dihydrocarbostyril.

23. 6-{3-[N-(4-Hydroxybutyl)-N-cyclohexylmethylaminocarbonyl]-propoxy}-3,4-dihydrocarbostyril.

24. 6-{4-[N-(5-Propionyloxypentyl)-N-cyclohexylmethylaminocarbonyl]butoxy}-3,4-dihydrocarbostyril.

25. 6-{4-[N-(2-Hydroxypropyl)-N-cyclohexylaminocarbonyl]butoxy}-3,4-dihydrocarbostyril.

26. 5-{3-[N-(2-Hydroxyethyl)-N-cyclohexylaminocarbonyl]propoxy}-3,4-dihydrocarbostyril.

27. A pharmaceutical composition used for the prevention and treatment of thrombosis containing an effective amount of the carbostyril derivative represented by the general formula (1) or its salt of claim 1.

* * * * *

UNITED STATES PATENT AND TRADEMARK OFFICE
CERTIFICATE OF CORRECTION

PATENT NO. : 4,435,404
DATED : March 6, 1984
INVENTOR(S) : Takao NISHI, Tatsuyoshi TANAKA, and Kazuyuki NAKAGAWA It is certified that error appears in the above—identified patent and that said Letters Patent is hereby corrected as shown below:

Claims 5, 7, and 8, lines 1 and 2, change "3 or 30" to --3 or 4--.

Claim 1, in the seventh and eighth lines following the structural formula, change "subsitituent" to --substituent--.

Signed and Sealed this

Twenty-eighth Day of August 1984

[SEAL]

Attest:

Attesting Officer

GERALD J. MOSSINGHOFF

Commissioner of Patents and Trademarks